(12) United States Patent
Webber

(10) Patent No.: US 7,198,904 B1
(45) Date of Patent: *Apr. 3, 2007

(54) IMMUNOASSAY METHOD EMPLOYING MONOCLONAL ANTIBODY REACTIVE TO HUMAN INOS

(76) Inventor: Robert Webber, 4175 Lakeside Dr., Suite 140, Richmond, CA (US) 94806

( * ) Notice: Subject to any disclaimer, the term of this patent is extended or adjusted under 35 U.S.C. 154(b) by 0 days.

This patent is subject to a terminal disclaimer.

(21) Appl. No.: 08/833,506

(22) Filed: Apr. 7, 1997

Related U.S. Application Data

(63) Continuation-in-part of application No. 08/634,332, filed on Apr. 12, 1996, now Pat. No. 6,531,578.

(51) Int. Cl.
*G01N 33/53* (2006.01)
*G01N 33/537* (2006.01)

(52) U.S. Cl. .............. 435/7.9; 435/7.91; 435/7.92; 435/7.93; 435/7.94; 435/7.95

(58) Field of Classification Search .......... 530/387.9, 530/388.76, 387.1, 864; 435/7.2, 7.9–7.95, 435/6, 331, 338; 436/518
See application file for complete search history.

(56) References Cited

U.S. PATENT DOCUMENTS 5,468,630 A * 11/1995 Billiar et al. ............... 435/189
5,658,565 A * 8/1997 Billiar et al. ............... 424/93.21
6,531,578 B1 * 3/2003 Webber .................. 530/387.1

FOREIGN PATENT DOCUMENTS

WO 23038 * 10/1994

OTHER PUBLICATIONS

Fujisawa et al J. Neurochemistry vol. 64 p. 85, 1995.*
Kobzik et al. Am. J. Respir. Cell Mol. Biol. vol. 9 p. 371, 1993.*
Ikeda, Tojo Medical journal vol. 65 p. 433 and translation, Jun. 1995.*
Chartrain et al, J. Biol. Chem. vol. 269 p. 6765, Mar. 1994.*
Skolnick et al. (Trends in Biotech., 18(1):34-39, 2000).*
Maier, Biochem. Biophys. Acta vol. 1208 p. 145 (Sep. 21, 1994).*
Harlow and Lane, antibodies (1988) p. 72-76.*
Marsden et al FEBS Letts vol. 307 p. 287 (Aug. 1992).*
Nakane et al FEBS Letts vol. 316 p. 175 (1993).*
Geller et al PNAS vol. 90 p. 3491 (Apr. 1993).*

* cited by examiner

*Primary Examiner*—Sheela J. Huff
(74) *Attorney, Agent, or Firm*—Theodore J. Bielen, Jr.

(57) ABSTRACT

A panel of monoclonal antibodies recognizing and binding to human inducible nitric oxide synthase (iNOS or type II iNOS) enzyme have been developed. The monoclonal antibodies may also be employed in an assay to detect the presence and/or quantitate the amount of human iNOS.

6 Claims, 30 Drawing Sheets

FIG. 1

Seq. 1:

| Gly | Ile | Val | Pro | Phe | Arg | Ser | Phe | Trp | Gln | Gln | Arg | Leu |
|-----|-----|-----|-----|-----|-----|-----|-----|-----|-----|-----|-----|-----|
|     |     |     |     | 5   |     |     |     |     | 10  |     |     |     |
| His | Asp | Ser | Gln | His |     |     |     |     |     |     |     |     |
| 15  |     |     |     |     |     |     |     |     |     |     |     |     |

Seq. 2:

| Pro | Ala | Leu | Val | Gln | Gly | Ile | Leu | Glu | Arg | Val | Val | Asp |
|-----|-----|-----|-----|-----|-----|-----|-----|-----|-----|-----|-----|-----|
|     |     |     |     | 5   |     |     |     |     | 10  |     |     |     |
| Gly | Pro | Thr | Pro | His |     |     |     |     |     |     |     |     |
| 15  |     |     |     |     |     |     |     |     |     |     |     |     |

Seq. 3:

| Asn | Asn | Asn | Val | Glu | Lys | Ala | Pro | Ser | Ala | Thr | Ser | Ser |
|-----|-----|-----|-----|-----|-----|-----|-----|-----|-----|-----|-----|-----|
|     |     |     |     | 5   |     |     |     |     | 10  |     |     |     |
| Pro | Val | Thr | Gln | Asp |     |     |     |     |     |     |     |     |
| 15  |     |     |     |     |     |     |     |     |     |     |     |     |

Seq. 4:

| Ser | Pro | Val | Thr | Gln | Asp | Asp | Leu | Gln | Tyr | His | Asn | Leu |
|-----|-----|-----|-----|-----|-----|-----|-----|-----|-----|-----|-----|-----|
|     |     |     |     | 5   |     |     |     |     | 10  |     |     |     |
| Ser | Lys | Gln | Gln | Asn |     |     |     |     |     |     |     |     |
| 15  |     |     |     |     |     |     |     |     |     |     |     |     |

Seq 5:

| Arg | Met | Thr | Leu | Val | Phe | Gly | Ser | Arg | Arg | Pro | Asp | Glu |
|-----|-----|-----|-----|-----|-----|-----|-----|-----|-----|-----|-----|-----|
|     |     |     |     | 5   |     |     |     |     | 10  |     |     |     |
| Asp | His | Ile | Tyr | Gln |     |     |     |     |     |     |     |     |
| 15  |     |     |     |     |     |     |     |     |     |     |     |     |

FIG. 7A

Seq. 6:

Val Glu Lys Ala Pro Ser Ala Thr Ser Ser Pro Val Thr
                    5                   10
Gln Asp
    15

Seq. 7:

Ala Pro Ser Ala Thr Ser Ser Pro Val Thr Gln Asp
                5                   10

Seq. 8:

Ala Thr Ser Ser Pro Val Thr Gln Asp
            5

Seq. 9:

Ser Pro Val Thr Gln Asp
            5

Seq. 10:

Asn Asn Asn Val Glu Lys Ala Pro Ser Ala Thr Ser Ser
                5                   10
Pro Val
    15

Seq. 11:

Asn Asn Asn Val Glu Lys Ala Pro Ser Ala Thr Ser
                5                   10

Seq. 12:

Asn Asn Asn Val Glu Lys Ala Pro Ser
                5

Seq. 13:

Asn Asn Asn Val Glu Lys
                5

Seq. 14:

Thr Gln Asp Asp Leu Gln Tyr His Asn Leu Ser Lys Gln
                5                   10
Gln Asn
    15

Seq. 15:

Asp Leu Gln Tyr His Asn Leu Ser Lys Gln Gln Asn
                5                   10

FIG. 7B

Seq. 16:

| Tyr | His | Asn | Leu | Ser | Lys | Gln | Gln | Asn |
|-----|-----|-----|-----|-----|-----|-----|-----|-----|
|     |     |     |     | 5   |     |     |     |     |

Seq. 17:

Leu Ser Lys Gln Gln Asn
              5

Seq. 18:

Ser Pro Val Thr Gln Asp Asp Leu Gln Tyr His Asn Leu
                 5                    10
Ser Lys
    15

Seq. 19:

Ser Pro Val Thr Gln Asp Asp Leu Gln Tyr His Asn
                 5                    10

Seq. 20:

Ser Pro Val Thr Gln Asp Asp Leu Gln
                 5

Seq. 21:

Ser Pro Val Thr Gln Asp
                 5

Seq. 22:

Val Gln Gly Ile Leu Glu Arg Val Val Asp Gly Pro Thr
                 5                    10
Pro His
    15

Seq. 23:

Ile Lue Glu Arg Val Val Asp Gly Pro Thr Pro His
                 5                    10

Seq. 24:

Arg Val Val Asp Gly Pro Thr Pro His
                 5

Seq. 25:

Asp Gly Pro Thr Pro His
                 5

FIG. 7C

Seq. 26:

Pro Ala Leu Val Gln Gly Ile Leu Glu Arg Val Val Asp
                    5                   10
Gly

Seq. 27:

Pro Ala Leu Val Gln Gly Ile Leu Glu Arg Val Val
                    5                   10

Seq. 28:

Pro Ala Leu Val Gln Gly Ile Leu Glu
                    5

Seq. 29:

Pro Ala Leu Val Gln Gly
                    5

Seq. 30:

Pro Phe Arg Ser Phe Trp Gln Gln Arg Leu His Asp Ser
                    5                   10
Gln His
    15

Seq. 31:

Ser Phe Trp Gln Gln Arg Leu His Asp Ser Gln His
                    5                   10

Seq. 32:

Gln Gln Arg Leu His Asp Ser Gln His
                    5

Seq. 33:

His Asp Ser Gln His
              5

Seq. 34:

Gly Ile Val Pro Phe Arg Ser Phe Trp Gln Gln Arg Leu
                    5                   10
His Asp
    15

Seq. 35:

Gly Ile Val Pro Phe Arg Ser Phe Trp Gln Gln Arg
                    5                   10

FIG. 7D

Seq. 36:

Gly Ile Val Pro Phe Arg Ser Phe Trp
                  5

Seq. 37:

Gly Ile Val Pro Phe Arg
                  5

Seq. 38:

Leu Val Phe Gly Ser Arg Arg Pro Asp Glu Asp His Ile
                  5                       10
Tyr Gln
    15

Seq. 39:

Gly Ser Arg Arg Pro Asp Glu Asp His Ile Tyr Gln
                  5                  10

Seq. 40:

Arg Pro Asp Glu Asp His Ile Tyr Gln
                  5

Seq. 41:

Glu Asp His Ile Tyr Gln
                  5

Seq. 42:

Arg Met Thr Leu Val Phe Gly Ser Arg Arg Pro Asp Glu
                  5                       10
Asp His
    15

Seq. 43:

Arg Met Thr Leu Val Phe Gly Ser Arg Arg Pro
                  5                  10

Seq. 44:

Arg Met Thr Leu Val Phe Gly Ser Arg
                  5

Seq. 45:

Arg Met Thr Leu Val Phe
                  5

FIG. 8

Seq. 46:

| Asn | Asn | Asn | Val | Lys | Lys | Thr | Pro | Ser | Ala | Val | Leu | Ser |
|-----|-----|-----|-----|-----|-----|-----|-----|-----|-----|-----|-----|-----|
|     |     |     |     | 5   |     |     |     |     | 10  |     |     |     |

Pro Thr Ile Gln Asp
    15

Seq. 47:

Asn Asn Asn Val Glu Lys Thr Pro Gly Ala Ile Pro Ser
            5                   10
Pro Thr Thr Gln Asp
    15

Seq. 48:

Pro Gly Leu Val Glu Ala Leu Leu Ser Arg Val Glu Asp
            5                   10
Pro Pro Ala Pro Thr Glu
    15

Seq. 49:

Gly Ile Ala Pro Phe Arg Ser Phe Trp Gln Gln Arg Gln
            5                   10
Phe Asp Ile Gln His
    15

Seq. 51:

Gly Ile Ala Pro Phe Arg Gly Phe Trp Gln Glu Arg Leu
            5                   10
His Asp
    15

Seq. 52:

Met Thr Leu Val Phe Gly Ser Arg Ser Ser Gln Leu Asp
            5                   10
His Leu Tyr Arg
    15

Seq. 53:

Met Val Leu Val Phe Gly Ser Arg Gln Ser Lys Ile Asp
            5                   10
His Ile Tyr Arg
    15

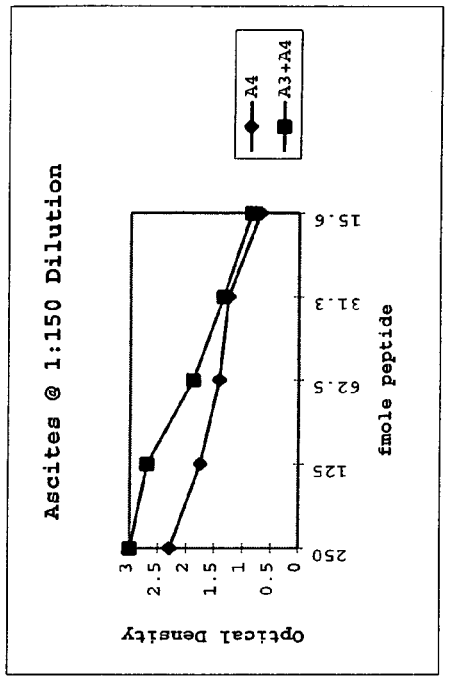
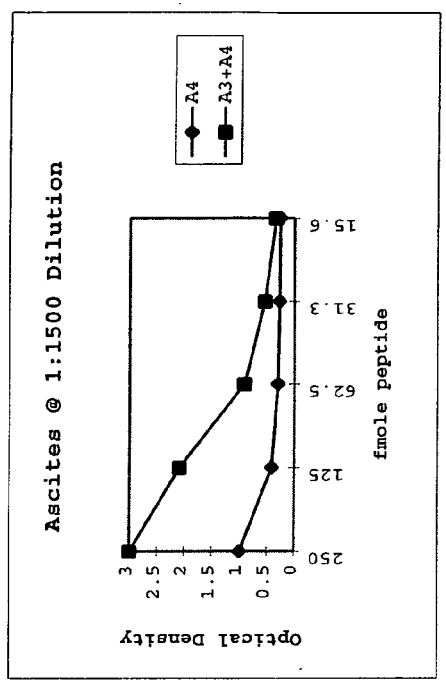
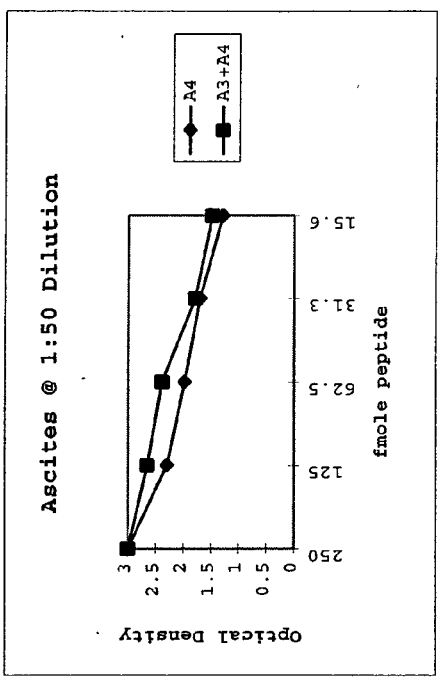
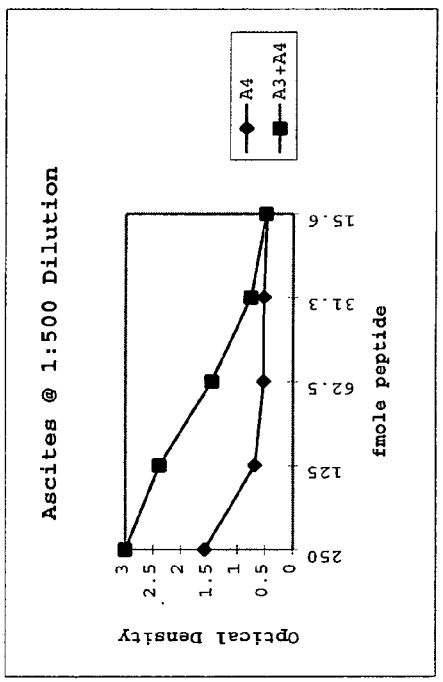
FIG. 32

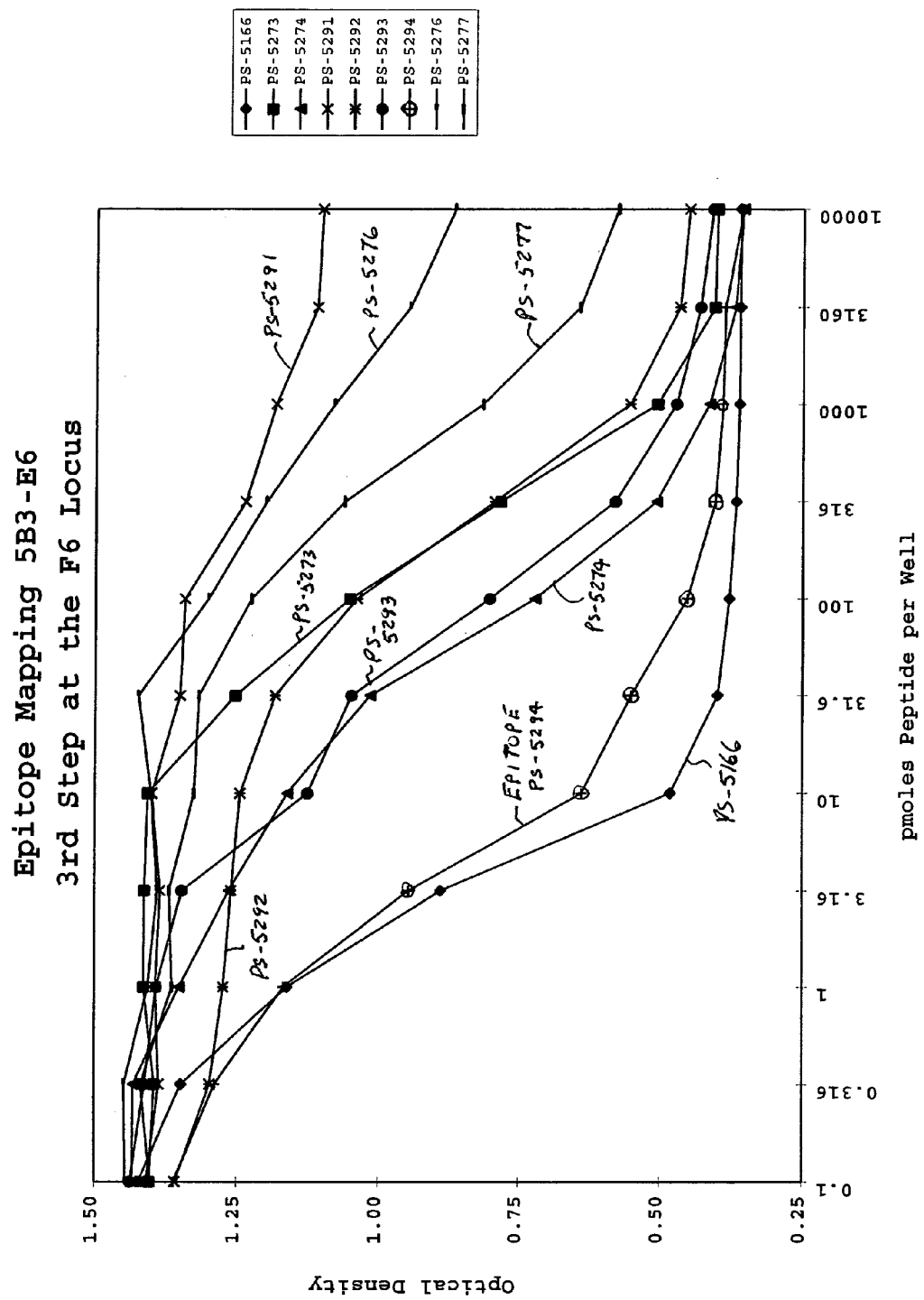

IMMUNOASSAY METHOD EMPLOYING MONOCLONAL ANTIBODY REACTIVE TO HUMAN INOS

CROSS-REFERENCES TO RELATED APPLICATIONS

The present application is a continuation-in-part of my prior application Ser. No. 08/634,332, filed 12 Apr. 1996.

BACKGROUND OF THE INVENTION

The present invention relates to a novel and useful panel of monoclonal antibodies which may be employed in immunoassays and other procedures for detection and/or quantitation of human iNOS.

Nitric oxide (NO) has recently been recognized as an effector and/or regulator molecule. For example, a recent field of investigation focused on the activity of NO upon the activation of soluble guanylate cyclase, which is responsible for endothelial dependent relaxation in the vasculature. An article entitled "Immunohistochemical Demonstration of a Paracrine Role of Nitric Oxide in Bronchial Function" by Rangassmy et al., American Physiological Society (1994) recognizes this effect with respect to bronchial blood vessels.

Concurrently, investigators have discovered that NO acts as a new neurotransmitter in the central and peripheral nervous system. In addition, activated macrophage cytotoxicity was found to be activated in host defense mechanisms based on the presence of NO. NO is now considered the smallest biosynthetically derived effector molecule secreted in mammalian systems. Reference is made to an article entitled "The Molecule of the Year", Science Magazine, Volume 258 (December 1992), by Koshland, which elaborates on the physiological importance of NO.

An article entitled "Increased Production of Nitric Oxide By Neutrophils and Monocytes From Cirrhotic Patients With Ascites and Hyperdynamic Circulation", by Laffi et. al., Hepatology, Volume 22, No. 6, (1995) and an article entitled "Molecular Cloning and Expression of Inducible Nitric Oxide Synthase from Human Hepatocytes" by Geller et al., Proc. Natl. Acad. Sci. USA, Volume 90 (April 1993) describes activity of nitric oxide synthase (NOS) and of nitric oxide in the liver. The latter reference includes an amino acid sequence describing human inducible NOS. In general, these articles associate cirrhosis with its concomitant activation of hepatocytes due to the inflammation and destruction of the liver, with the induction of iNOS and the subsequent overproduction of NO.

Rejection of transplanted organs is proposed to be mediated by host defense mechanisms in which activated monocytes, macrophages, and/or neutrophils are active, and through the actions of iNOS leads to the inevitable production of NO. Others have attempted to develop drugs which specifically inhibit iNOS, thus stopping the production of NO, without simultaneously inhibiting either neuronal NOS (nNOS) or endothelial (eNOS), the other two isofroms of this enzyme.

An article entitled "Increased Nitric Oxide Synthase Activity Despite Lack of Response to Endothelium-dependent Vasodilators in Postischemic Acute Renal Failure in Rats", by Conger et al., The Journal of Clinical Investigations, Inc., Volume 96 (July 1995) recognizes nitric oxide activity in the failure of rat kidneys.

An article entitled "Immunohistochemistry in the Identification of Nitric Oxide Synthase Isoenzymes in Myocardial Infarction", by Wildhirt et al., Cardiovascular Research, Volume 29 (1995) recognizes the conversion of L-arginine to citrulline and nitric oxide in infarcted rabbit myocardium, which leads to damage of the heart.

The NO biosynthetic pathway has been extensively examined recently. It is now recognized that there is a family of isozymes which produce NO. An article entitled "The Nitric Oxide Synthase Family of Proteins", by Sessa, J. Vasc. Res. (1994) recognizes the trio of NOS isozymes. All three NOS isozymes catalyze the conversion of L-arginine and oxygen to citrulline and NO. In addition, five co-factors have also been found to be required for this catalytic conversion. These are calmodulin, NADPH, FAD, FMN, and tetrahydrobiopterin. Generally, the three isoforms of NO synthase (NOS) have been labeled type 1 (nNOS), the neuronal isoform; type 2 (iNOS), the inducible isoform; and type 3 (eNOS), the endothelial isoform. nNOS and eNOS are constitutively expressed in the cells in which they are found. iNOS is not constitutively expressed, but rather is induced by a number of cytokines and lypopolysaccarides (LPS). It has been further discovered that nNOS serves as a neurotransmitter. iNOS, further, concerns host defense and cellular immunity. Also, vascular tone and hemodynamic control has been linked to eNOS. The three (3) isoforms of the NOS enzyme fall in the category of true isozymes since they share approximately 60% sequence homology. iNOS has been specifically implicated in certain pathological diseased states. An article entitled "Expression and Preferential Inhibition of Inducible Nitric Oxide Synthase in Aortas of Endotoxemic Rats", by Weigert et al., Journal of the American Society of Nephrology, Volume 5, No. 12 (1995) discusses the functional importance of iNOS with respect to septic shock. Specifically, where sepsis and septic shock occurs, numerous cytokines and LPS from gram negative bacteria potentially can induce the expression of iNOS in monocytes, macrophages, neutrophils, hepatocytes, or other cell types, which leads to the overproduction of NO. This in turn leads to the deleterious effects associated with sepsis and septic shock due to extensive systemic vasodilation.

Various groups of researchers have reported on the development of monoclonal antibodies to NOS and on the utilization of such antibodies for biomedical experimentation. An article entitled "Stabilization of Inducible Nitric Oxide Synthase by Monoclonal Antibodies" by Hattori et al., Hybridoma, Volume 12, No. 6 (1993) states that a panel of monoclonal antibodies to rat iNOS was derived from activated rat peritoneal macrophages. It was reported therein that none of the monoclonal antibodies neutralized the enzymatic activity of rat iNOS, but some of the monoclonal antibodies stabilized the enzyme.

An article entitled "Transient Expression of Calcium-Independent Nitric Oxide Synthase in Blood Vessels During Brain Development" by Galea et al., FASEB Journal, Volume 9, (December 1995), describes a protein band which was detected with a monoclonal antibody raised against rat iNOS. Moreover, the Rengasamy article, prior identified, describes the development and characterization of a monoclonal antibody developed to bovine nNOS. Through western immunoblots, this monoclonal antibody was found to recognize bovine nNOS, bovine eNOS, and mouse iNOS. The same monoclonal antibody was found to recognize rat nNOS, rat eNOS, and rat iNOS, by immunohistochemical techniques.

An article entitled "Inducible Nitric Oxide Synthase In A Human Glioblastoma Cell Line" by Fujisawa et al., Journal of Neurochemistry, Vol. 64 (1995) describes iNOS induction in A-172 cells, which is a human glioblastoma cell line.

An article entitled "Immunochemical Detection of Inducible NO Synthase in Human Lung" by Tracey et al., American Physiological Society, Rapid Communication (1994) describes iNOS induction in RAW 264.7 macrophages. Polyclonal antibodies raised against mouse iNOS derived from induced RAW 264.7 cells and were used to investigate the expression of iNOS in human lung tissue.

An article entitled "Characterization and Localization of Endothelial Nitric Oxide Synthase Using Specific Monoclonal Antibodies" by Pollock et al., American Physiological Society (1993) describes the development and characterization of a panel of monoclonal antibodies developed to bovine eNOS, which do not cross react with either nNOS or iNOS.

U.S. Pat. Nos. 4,376,110 and 4,879,219 describe immunoassays utilizing monoclonal antibodies to detect antigenic substances.

A brochure from Transduction Laboratories, Lexington, Ky., offers a number of mouse monoclonal antibodies raised to recombinant fragments of various rat isoforms of NOS.

A company called Santa Cruz Biotechnology in a brochure entitled "Signaling Intermediates—NOS" offers a number of polyclonal anti-peptide antibodies specific for the various isoforms of NOS.

A brochure entitled "Isostrip" by Boehringer Mannheim Corporation illustrates a simplified mouse monoclonal antibody isotyping kit which uses treated strips to detect mouse immunoglobulin subclasses, and kappa or lambda light chains.

The development of a panel of monoclonal antibodies to human iNOS for immunoassays specific for human iNOS would be a notable advance in the bio-medical field.

SUMMARY OF THE INVENTION

In accordance with the present invention a novel and useful panel of monoclonal antibodies specific to human iNOS have been developed and have been demonstrated to be useful in immunoassays that are specific for human iNOS. These monoclonal antibodies have been characterized by a number of different standard techniques.

In addition, a number of assays have been developed using the monoclonal antibodies which are reactive to human iNOS, that also bind to specific linear synthetic peptide analogues of the protein. For example, assays of the competitive binding ELISA, immunofluorescent assay (IFA) types have been developed. In addition, Western blot, dip stick, fluorescent polarization, enzyme capture, and radioimmunoassay (RIA) may also be employed in this regard. The assays were employed with mouse models of human septic shock and human samples of septic shock, and validated under controlled circumstances.

A number of specific regions of human iNOS were employed in the present invention. Namely, the A3, A4, A3+A4, F6, G11 and/or the H1 loci of human iNOS were targeted. Specific binding pairs and specific binding reagent molecules were also developed in conjunction with these loci. For example, the monoclonal antibodies, above mentioned, served as specific binding entities. Of course, polyclonal antibodies, oligonucleotides, polymers imprinted as artificial antibodies, phage display binding sites, and the like may also be used in this regard. Further, combinations of peptides may be incorporated into the assays of the present invention.

Peptide and peptide analogues at the iNOS regions above identified, can be used with specific binding pair partners or with specific binding reagent molecules for direct, indirect, captured, competitive binding, displacement, and other types of assays and assay kits. Any one of such assays or assay kits may be used to detect or measure iNOS quantitatively or qualitatively. Such assays may be of the clinical diagnostic type.

Further, the peptide and peptide analogues, identified hereinafter, also include an active region or active portion which will produce satisfactory results. Specifically, epitope mapping was performed for the clones identified as 21C10-1D10, 2D2-B2, and 5B3-E6. It should be noted however, that synthetic peptides, recombinant peptides, recombinant proteins, fusion proteins, fusion peptides, phage displayed proteins, phage displayed peptides, peptide libraries, peptide analog libraries, and the like may be employed, where the active component is a mimic to A3, A4, A3+A4, F6, G11, and/or H1 loci of human iNOS. In addition, regions of human iNOS may be combined in whole or in part in the present assay. For example, region F6 may be combined with a small portion of region H1 of human iNOS in an assay regent.

The assays of the present invention may detect or measure human iNOS in cells and tissues for various pathophysiological conditions such as sepsis, septic shock in humans and in mouse models, myocardial infarction, rejection of tissue in organs following transplantation, monitoring "flare ups" in certain autoimmune diseases such as lupus, psoriasis, multiple sclerosis, and the like. Specifically, IFA and competitive binding ELISA assays tested several of such tissues. However, as noted above, other assay methods may also be employed using the binding entities of the present invention. In addition, the sensitivity of certain assays, such as competitive binding ELISA, were increased by using combination of peptides. For example, the peptide to A3+A4 was deemed to increase the sensitivity of the assay to A4 alone, by 4 times. Amplification with avidin-biotin complex increased the assay sensitivity 12 to 15 times. The two combined increased sensitivity 48 to 60 times.

It may be apparent that a novel and useful method for immunoassay and immunoassay components have been described.

An object of the present invention is the development of immunoassays which can be used as clinical tests for hiNOS utilizing monoclonal antibodies specific to hiNOS.

Another object of the present invention is to develop a separate panel of polyclonal rabbit anti-peptide antibodies, which are specific for the three (3) isoforms of hiNOS.

Yet another object of the present invention is to produce peptide sequences which mimic regions of hiNOS, and that bind to the monoclonal antibodies of the present invention.

A further object of the present invention is to provide a method to carry out immunoassays which utilize specific binding entities which are reactive to human iNOS protein and which reveal the presence of the same by any number of immunoassay formats.

Another object of the present invention is to provide immunoassay method which utilizes a specific binding entity reactive to mimics of human iNOS protein to reveal the presence of human iNOS protein in a sample.

A further object of the present invention is to provide truncated peptide sequences which mimic regions of hiNOS and that bind to the monoclonal antibodies of the present invention.

Another object of the present invention is to provide homolog peptides from proteins other than human iNOS to test the specificity characteristics of the monoclonal antibodies.

Yet another object of the present invention is to characterize the panel of monoclonal antibodies of the present invention to ascertain their individual utility in various assays and procedures.

The invention possesses other objects and advantages especially as concerns particular characteristics and features thereof which will become apparent as the specification continues.

BRIEF DESCRIPTION OF THE DRAWINGS

FIG. 1 is a listing of five amino acid sequences representing regions of hiNOS to which various monoclonal antibodies, from the overall panel of monoclonal antibodies, of the present invention have bound.

FIGS. 7A–D are a listing of the peptide sequences usable for epitope mapping of the monoclonal antibodies of the present invention.

FIG. 8 is a listing of the peptide sequences usable to determine specificity characterization of the monoclonal antibodies of the present invention.

FIG. 32 is a panel of four graphs depicting the increased sensitivity in the competitive binding ELISA for hiNOS using mouse $IgG_1$ monoclonal antibody 21C10-1D10 and the 30 amino acid long A3+A4 peptide, PS-5251, as compared to the 18 amino acid A4 peptide, PS-5104, at four different dilutions of ascites fluid.

FIG. 36 is a graph depicting the competitive binding ELISA using mouse monoclonal antibody 5B3-E6, the standard F6 peptide (PS-5166), and peptides from the three mid-region elongation series of Table X which locates the antibody's epitope to PS-5294, VQGILERV (SEQ ID NO: 121).

DESCRIPTION OF THE PREFERRED EMBODIMENTS

Figure 2:
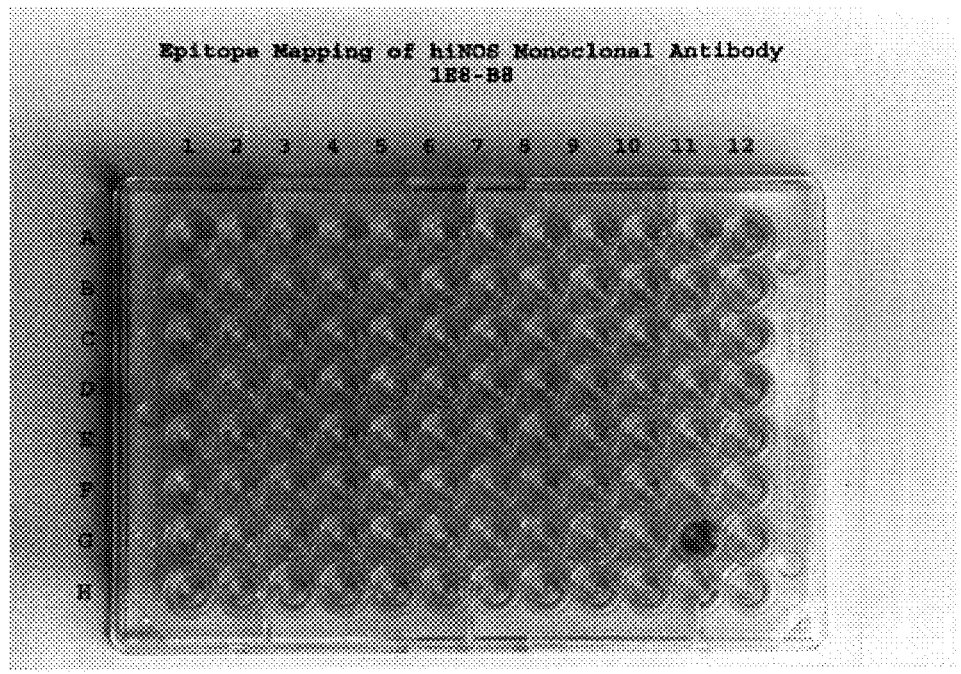
FIGS. 2–6 are photos of positively tested microtiter plates using the monoclonal antibodies of the present invention, as described in Example 3.
Figure 3:
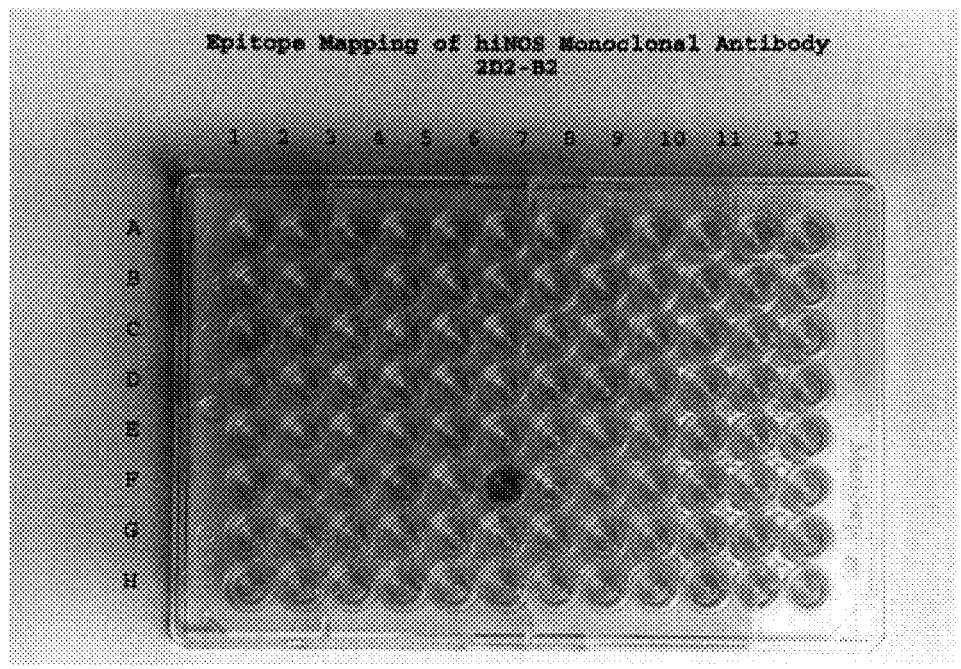
Figure 4:
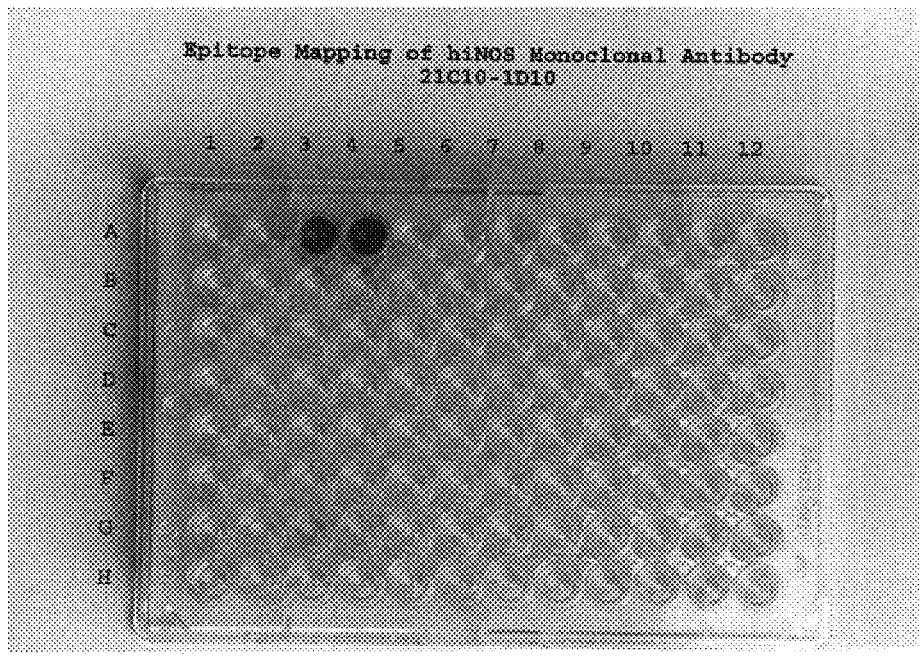
Figure 5:
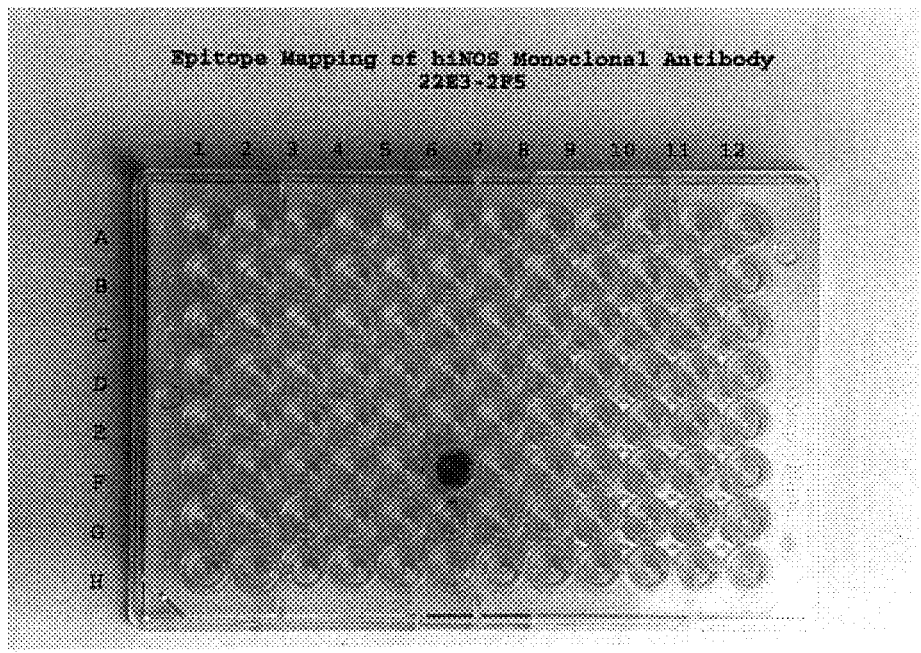
Figure 6:
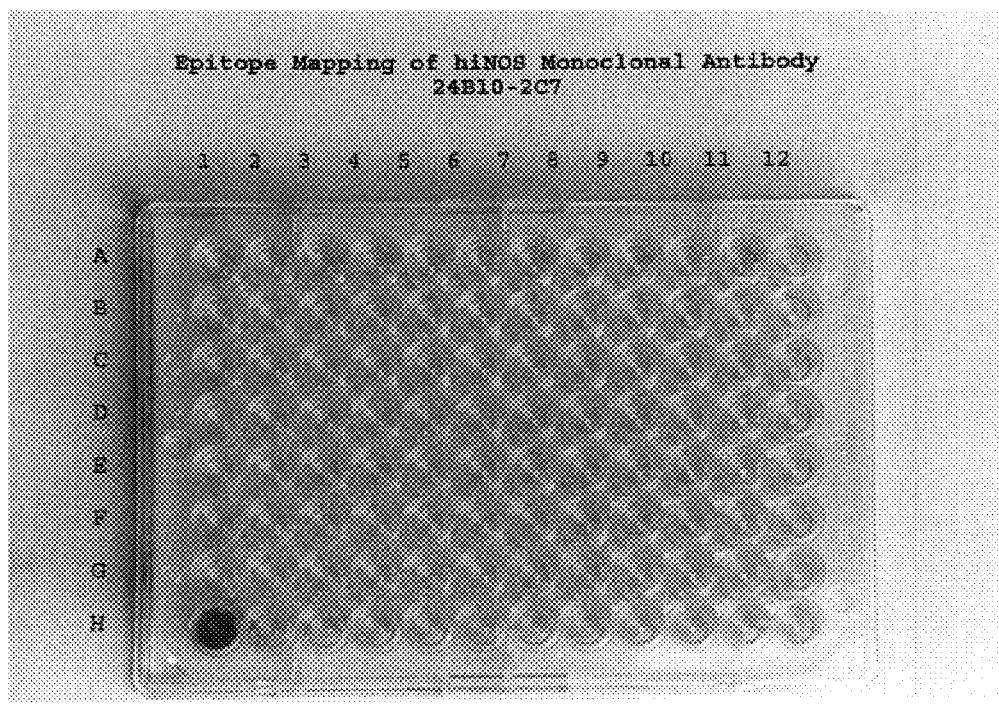

Various aspects of the present invention will evolve from the following detailed disclosure of the preferred embodiments thereof which should be referenced to the prior described drawings.

A panel of mouse monoclonal antibodies specific for the inducible form of human NOS (hiNOS) has been developed. The monoclonal antibodies were characterized by a number of different techniques including enzyme-linked immunosorbent assay (ELISA), western immunoblots, immunoprecipitation of $^{125}$I-hiNOS, and indirect immunofluorescent staining of cells. All the monoclonals were initially detected by ELISA, and all perform well in ELISA based assays. However, in all the other assay formats tested, some of the anti-hiNOS monoclonal antibodies worked well and others did not. Only one monoclonal antibody, 1E8-B8, has been found to perform well in all the assay formats tested. Others of the panel, such as 2A12-A4, 2D2-B2, 5B3-E6, 2H11-D11, 7D8-B3, and 21C10-1D10, perform well in most but not all of the assay formats examined. Thus, it will be necessary to test each of the monoclonal antibodies of the panel for suitability in any specific assay format or for any specific purpose. Such monoclonal antibodies have been used in immunoassays to determine the presence and quantity of hiNOS.

These monoclonal antibodies were elicited using whole hiNOS as immunogen. However, many, if not all, of these monoclonal antibodies could be developed using fragments or peptide analogues of hiNOS to elicit the initial immune response in mice. In addition, a separate panel of polyclonal rabbit anti-peptide antibodies were developed. Such polyclonal antibodies were specific to the three isoforms of NOS (nNOS, iNOS, eNOS). The polyclonal antibodies were raised in rabbits to peptides of defined amino acid sequences, which mimicked either the amino terminal or the carboxyl terminal of each of the isoforms of human NOS. The peptides used in the polyclonal antibody production were synthesized according to known techniques.

In addition, purified human iNOS was employed to immunize mice and to develop a panel of monoclonal antibodies. The monoclonal antibodies could have been developed using protein fragments, fusion peptides and proteins, or peptide analogues of hiNOS to immunize mice and elicit an immune response to regions of hiNOS. Standard techniques were used to produce the hybridomas, clone the cells, and produce the monoclonal antibodies. The hybridomas and clones were screened by ELISA and western immunoblot and used in the production of monoclonal antibodies as culture supernatant and as ascites fluid from mice. The monoclonal antibodies were characterized by standard techniques and were also isotyped. The monoclonal antibodies were then tested for their ability to inhibit the enzymatic activity of hiNOS. In order to determine which region of the protein each monoclonal antibody was recognizing, 96 overlapping peptides, each 18 amino acids long, were synthesized to cover the entire 1153 amino acid length structure of the hiNOS. Each peptide had a six amino acid long overlap with its nearest neighbors, except the carboxyl terminal peptide which had an 11 amino acid overlap with the prior peptide. The peptides were used to sensitize a specific well on microtiter plates, and culture supernatant or ascites fluid from each clone was applied individually to the wells. The presence of bound monoclonal antibody was then determined. Specific regions of the iNOS protein were identified as being bound by the monoclonal antibodies. FIG. 1 represents peptide sequences which represent the specific regions of human iNOS which were determined to bind to some of the monoclonal antibodies of the present invention.

Once the region to which a specific monoclonal antibody was determined to bind, a computer search of the known protein databases was performed to find similar sequences of other proteins. This service is provided by the National Center for Biotechnology Information at the National Institutes of Health. A program named Basic Logistic Alignments Statistical Tool (BLAST) was employed in this search. The use of such tool is described in an article entitled "Basic Local Alignment Search Tool" by Altschul et al., Journal of Molecular Biology, Vol. 215 (1990). The following table represents the results of the computer search:

TABLE I

Sequence Homologies of Peptides to Regions of Proteins

| Peptide | Region | Sequence | P Value |
|---|---|---|---|
| A3 | human iNOS (25–42) | Asn Asn Asn Val Glu 5 | $<2 \times 10^{-6}$ |
| | | Lys Ala Pro Cys Ala 10 | |
| | | Thr Ser Ser Pro Val 15 | |
| | | Thr Gln Asp SEQ ID NO 1 | |
| | mouse iNOS (25–42) | Asn Asn Asn Val Lys 5 | <0.02 |
| | | Lys Thr Pro Cys Ala 15 | |
| | | Val Leu Ser Pro Thr 20 | |
| | | Ile Gln Asp SEQ ID NO 2 | |
| | rat iNOS (25–42) | Asn Asn Asn Val Glu 5 | <0.03 |
| | | Lys Thr Pro Gly Ala 10 | |
| | | Ile Pro Ser Pro Thr 15 | |
| | | Thr Gln Asp SEQ ID NO 3 | |

TABLE I-continued

Sequence Homologies of Peptides to Regions of Proteins

| Peptide | Region | Sequence | P Value |
|---|---|---|---|
| A4 | human iNOS (37–54) | Ser Pro Val Thr Gln 5 | $<2 \times 10^{-6}$ |
| | | Asp Asp Leu Gln Tyr 10 | |
| | | His Asn Leu Ser Lys 15 | |
| | | Gln Gln Asn SEQ ID NO 4 | |
| F6 | human iNOS (781–798) | Pro Ala Leu Val Gln 5 | $<1 \times 10^{-6}$ |
| | | Gly Ile Leu Glu Arg 10 | |
| | | Val Val Asp Gly Pro 15 | |
| | | Thr Pro His SEQ ID NO 5 | |
| | mouse iNOS (776–792) | Xxx Ala Leu Val Gln 5 | $<0.001$ |
| | | Gly Ile Leu Glu Arg 10 | |
| | | Val Val Asp Cys Pro 15 | |
| | | Thr Pro His SEQ ID NO 6 | |
| | rat iNOS (780–794) | Xxx Xxx Leu Val Gln 5 | $<0.1$ |
| | | Gly Ile Leu Glu Arg 10 | |
| | | Val Val Asp Cys Ser 15 | |
| | | Ser Pro Xxx SEQ ID NO 7 | |
| G11 | human iNOS (985–1002) | Gly Ile Val Pro Phe 5 | $<2 \times 10^{-8}$ |
| | | Arg Ser Phe Trp Gln 10 | |
| | | Gln Arg Leu His Asp 15 | |
| | | Ser Gln His SEQ ID NO 8 | |
| | mouse iNOS (978–995) | Gly Ile Ala Pro Phe 5 | $<1 \times 10^{-7}$ |
| | | Arg Ser Phe Trp Gln 10 | |
| | | Gln Arg Leu His Asp 15 | |
| | | Ser Gln His SEQ ID NO 9 | |
| | rat iNOS (982–998) | Gly Ile Ala Pro Phe 5 | $<1 \times 10^{-7}$ |
| | | Arg Ser Phe Trp Gln 10 | |
| | | Gln Arg Leu His Asp 15 | |
| | | Ser Gln His SEQ ID NO 10 | |
| | human nNOS (1256–1273) | Gly Ile Ala Pro Phe 5 | $<1 \times 10^{-4}$ |
| | | Arg Ser Phe Trp Gln 10 | |
| | | Gln Arg Gln Phe Asp 15 | |
| | | Ile Gln His SEQ ID NO 11 | |
| | human eNOS (1017–1031) | Gly Ile Ala Pro Phe 5 | $<0.001$ |
| | | Arg Gly Phe Trp Gln 10 | |
| | | Glu Arg Leu His Asp 15 | |
| | | Xxx Xxx Xxx SEQ ID NO 12 | |
| | bovine eNOS (1019–1033) | Gly Ile Ala Pro Phe 5 | $<0.001$ |
| | | Arg Gly Phe Trp Gln 10 | |
| | | Glu Arg Leu His Asp 15 | |
| | | Xxx Xxx Xxx SEQ ID NO 13 | |
| H1 | human iNOS (1009–1026) | Arg Met Thr Leu Val 5 | $<1 \times 10^{-6}$ |
| | | Phe Gly Cys Arg Arg 10 | |
| | | Pro Asp Glu Asp His 15 | |
| | | Ile Tyr Gln SEQ ID NO 14 | |
| | rat iNOS (1006–1023) | Arg Met Thr Leu Val 5 | $<1 \times 10^{-4}$ |
| | | Phe Gly Cys Arg His 10 | |
| | | Pro Glu Glu Asp His 15 | |
| | | Leu Tyr Gln SEQ ID NO 15 | |

TABLE I-continued

Sequence Homologies of Peptides to Regions of Proteins

| Peptide | Region | Sequence | P Value |
|---|---|---|---|
| | mouse iNOS (1002–1019) | Arg Met Ser Leu Val Phe Gly Cys Arg His Pro Glu Glu Asp His Leu Tyr Gln SEQ ID NO 16 | $<2 \times 10^{-4}$ 5<br><br>10<br><br>15 |

Where "Xxx" represents mismatched amino acids which were not used in the BLAST calculations.

"P Value" represents the probability of dissimilarity. In other words, the smaller the value, the more likely the probability of there being a match. For example, the results of the BLAST calculations for peptide A3 in Table I found complete sequence homology with hiNOS (25–42). This was expected since this is the region of hiNOS that this peptide was built to mimic. The computer search only found sequence homology with two other proteins. One sequence homology concern mouse iNOS (25–42) with a P Value of less than 0.02. The other sequence homology was rat iNOS (25–42) with a P Value of less than 0.03. No sequence homology was found to any other proteins in the databases with a P Value of less than 0.1. The search of the protein database for sequence homology with peptide A4 found homology only with human iNOS (37–54) which is the region mimicked by the peptide. No region of any other protein in the databases was determined to match this sequence with a P Value of less than 0.1 (i.e., the probability that there is a difference is greater than 99.9%). The search for sequence homology to peptide F6 which is hiNOS (781–798) found sequence homology with human iNOS and with mouse and rat iNOS. No homology was found during this search to any other protein with a P Value of less than 0.1. However, the search for sequence homology with peptide G11, which is hiNOS (985–1002), found homology to a number of proteins in Table I. These included mouse and rat iNOS, human nNOS (1256–1273), human eNOS (1017–1031), and bovine eNOS (1019–1033). The computer search for sequence homology to peptide H1, which is hiNOS (1009–1026), found homology only with rat and mouse iNOS. No other sequence homology was found with a P Value less than 0.5. It should be noted that a small amount of homology was found with human eNOS and human nNOS, but the P Values are greater than 0.5.

The sequences from each of the 18-mers to which monoclonal antibodies are found to bind, i.e., peptides A3 (PS-5103), A4 (PS-5104), F6 (PS-5166), G11 (PS-5183), and H1 (PS-5185), Table I, were used to design and make a series of epitope mapping peptides for these regions. A series of four truncation peptides from the amino acid terminal end of the 18-mers, as well as a series of four truncations from the carboxyl terminal of each of the 18-mers were fashioned. Various degrees of truncation were used to determine the minimum lengths of amino acids to which some of binding to the monoclonal antibodies of the present invention could bind. FIG. 7 represents amino acid sequences showing such truncated peptides which were bound by some of the monoclonal antibodies of the present invention.

In addition, a number of peptide homologue were designed and synthesized based on the BLAST search. These peptide homologue were used to characterize the specificity of the monoclonal antibodies to proteins other than hiNOS. For example, such other proteins included hNOS, heNOS, mouse iNOS, and rat iNOS.

An immunoassay was set-up to determine the presence and quantity of hiNOS in samples. Purified goat anti-rabbit IgG was used to sensitize microtiter plates. The plates were blocked with bovine serum albumin (BSA). Rabbit polyclonal anti-peptide antibody was added and allowed to bind as the "catch" antibody in order to bind hiNOS in samples. Various mouse monoclonal antibodies from the panel of Table III were tested for their ability to detect and quantitate hiNOS. Clones 1E8-B8, 21C10-1D10, 2A12-A4, and others of Table III were found to work in this format. It is believed that other formats such as the formation of strips for rapid detection of iNOS may be applicable to the assay of the present invention.

In addition to use in sandwich ELISAs, the panel of monoclonal antibodies of Table III were tested for their ability to detect hiNOS in samples by western immunoblot techniques. In this technique, cells in culture were induced with a cytokine/LPS mix. The latter technique induced the production of iNOS by the cells which was detectable in western immunoblots by the monoclonal antibodies of the present invention.

In addition to use in sandwich ELISAs and western immunoblots, each of the monoclonal antibodies in the panel of Table III was tested for its ability of immunoprecipitate hiNOS. This was tested by radioimmunoassay (RIA) techniques using $^{125}$I-labeled hiNOS. Ten of the 20 different monoclonal antibodies in the panel were determined to immunoprecipitate hiNOS by this method. Of the ten positives found, monoclonal antibodies 2H11-D11, 5B3-E6, and 21C10-1D10 were found to be the best at immunoprecipitating the radiolabeled protein.

The ability of the monoclonal antibodies in Table III to recognize and bind to iNOS in fixed cells was also investigated. Induction of iNOS production was examined in three very different types of cultured cells by indirect immunofluorescent staining of the induced cells using the anti-hiNOS monoclonal antibodies as the primary antibody. The three types of induced cultured cells tested were A-172 (a human glioblastoma cell line), RAW 264.7 (a mouse macrophage cell line), and normal human monocytes isolated from blood. Five monoclonal antibodies, 1E8-B8, 2D2-B2, 5B3-E6, 2A12-A4, and 2H11-D11, were found to perform particularly well in this assay format: other monoclonals from the panel performed less well or did not stain the cells.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

The following examples are presented as being illustrative of the invention, but are not intended to be limiting of the invention or any embodiment thereof, unless specified hereinafter.

EXAMPLE 1

Production of Polyclonal Antibodies

Peptides of defined amino acid sequences were prepared, which mimicked either the amino terminal or the carboxyl terminal of each of the isoforms of human NOS. Each peptide was synthesized by solid phase peptide synthesis utilizing the fmoc protecting strategy. The synthetic peptides were cleaved from the solid support resin, isolated, and purified by standard procedures including preparative HPLC. They were analyzed for purity by analytical HPLC.

1. Each synthetic peptide was conjugated onto a carrier protein, keyhole limpet hemocyanin (KHL), using either the EDAC or sulfo-MBS chemistries to construct the immunogens for the elicitation of antibodies.

2. Each peptide/protein conjugate was used as an immunogen in rabbits. The different immunogens were employed to immunize groups of 2–4 rabbits each. The rabbits were immunized, boosted, and bled following a standard protocol developed for the production of anti-peptide antibodies in rabbits.

3. The antiserum obtained from each bleed of each rabbit was tested by ELISA for the production of antibodies specific for the synthetic peptide analogue. Those antisera found positive for production of antibodies specific for the peptide portion of the immunogen were then assessed for their ability to recognize the whole protein.

Table II represents a summary of such synthetic peptides.

TABLE II

Synthetic Peptides Used as Immunogens

| Batch # & segment | Sequence Location | Amino Acid Sequence |
|---|---|---|
| PS-1656 hnNOS [2–16, Cys$^{17}$] | human nNOS: amino terminal | Glu Asp His Met Phe 5<br>Gly Val Gln Gln Ile 10<br>Gln Pro Asn Val Ile 15<br>Cys<br>SEQ ID NO 17 |
| PS-1653 hnNOS [Cys$^{1410}$-1411-1433] | human nNOS: carboxyl terminal | Cys Arg Leu Arg Ser 5<br>Glu Ser Ile Ala Phe 10<br>Ile Glu Glu Ser Lys 15<br>Lys Asp Thr Asp Glu 20<br>Val Phe Ser Ser<br>SEQ ID NO 18 |
| PS-1673B hiNOS [2–21, Ser$^2$] | human iNOS: amino terminal | Ala Ser Pro Trp Lys 5<br>Phe Leu Phe Lys Thr 10<br>Lys Phe His Gln Tyr 15<br>Ala Met Asn Gly Glu 20<br>SEQ ID NO 19 |
| PS-1643 hiNOS [Cys$^{1136}$-1137-1153] | human iNOS: carboxyl terminal | Cys Lys Lys Asp Arg 5<br>Val Ala Val Gln Pro 10<br>Ser Ser Leu Glu Met 15<br>Ser Ala Leu<br>SEQ ID NO 20 |
| P5-1686 heNOS [Cap-2–12, Cys$^{13}$] | human eNOS: amino terminal with caproic acid attached | Cap-Gly Asn Leu Lys Ser Val Ala Gln Glu 5<br>Pro Gly Cys 10<br>SEQ ID NO 21 |
| PS-1687 heNOS [2–12, Cys$^{13}$] | human eNOS: amino terminal without caproic acid attached | Gly Asn Leu Lys Ser 5<br>Val Ala Gln Glu Pro 10<br>Gly Cys<br>SEQ ID NO 22 |
| PS-1648 heNOS [Cys$^{1181}$-1182-1203] | human eNOS: carboxyl terminal | Cys Glu Arg Gln Leu 5<br>Arg Glu Ala Val Pro 10<br>Trp Ala Phe Asp Pro 15<br>Pro Gly Ser Asp Thr 20<br>Asn Ser Pro<br>SEQ ID NO 23 |

EXAMPLE 2

Production of Monoclonal Antibodies

Purified human iNOS was used to immunize mice and develop a panel of monoclonal antibodies. Standard techniques were used to produce the hybridomas, clone the cells, and produce the monoclonal antibodies. Such techniques are described in a protocol entitled "Production of Monoclonal Antibodies", Current Protocols in Immunology (1991). Briefly, spleens from immunized mice were aseptically removed, splenocytes were isolated and were fused with SP2/0-Ag 14 myeloma cells with polyethylene glycol. Hybridomas were screened by ELISA for production of mouse IgG or IgM antibodies to hiNOS. Positive hybrids were expanded and cloned via limiting dilution. The clones were screened by ELISA and western immunoblot techniques. Positive clones were expanded, frozen down in liquid nitrogen for cryopreservation, and used for the production of monoclonal antibodies as culture supernatant, as well as ascites fluid from Balb/C female mice.

The monoclonal antibodies produced by the various clones were characterized by a number of different techniques. These include ELISA, western immunoblot, immunoprecipitation of $^{125}$I--hiNOS (I.P.), and indirect immunofluorescent staining of cells (I.F.A.). The monoclonal antibodies were also isotyped. Table III represents these results:

TABLE III

Characteristics of hiNOS Monoclonal Antibodies

| Clone | Isotype | ELISA | Western Immuno-Blot | I.P. | I.F.A. |
|---|---|---|---|---|---|
| 1A11-F7 | Mouse IgG1 kappa | + | – | + | ND |
| 1E8-B8 | Mouse IgG1 kappa | + | + | + | + |
| 2A1-F8 | Mouse IgG2a kappa | + | + | + | ND |
| 2A12-A4 | Mouse IgG1 kappa | + | + | – | + |
| 2D2-B2 | Mouse IgG1 kappa | + | – | – | weak |
| 2D10-F12 | Mouse IgG2A kappa | + | – | – | – |
| 2H11-D11 | Mouse IgM kappa | + | – | + | + |
| 4E8-G9 | Mouse IgG2B kappa | + | – | – | ND |
| 5B3-E6 | Mouse IgG1 kappa | + | – | + | weak |
| 5D5-H10 | Mouse IgG1 kappa | + | + | – | ND |
| 6A12-A12 | Mouse IgG2a kappa | + | – | + | ND |
| 6G12-H7 | Mouse IgG1 kappa | + | + | – | ND |
| 7D8-B3 | Mouse IgM | + | – | + | + |
| 21C10-1D10 | Mouse IgG2B Kappa | + | + | + | – |
| 21D4-2A8 | Mouse IgM | + | – | + | + |
| 21H11-2D2 | Mouse IgG | + | – | + | ND |
| 22E3-2F5 | Mouse IgG1 Kappa | + | + | – | – |
| 23G6-2A12 | Mouse IgG1 Kappa | + | + | – | – |
| 24B10-2C7 | Mouse IgG1 Kappa | + | – | – | – |
| 24H9-1F3 | Mouse IgG1 Kappa | + | + | – | – |

Where "ND" indicates "not determined"; "+" is "positive"; "–" is "negative"; and "weak" represents binding at only very high monoclonal antibody concentrations.

EXAMPLE 3

Epitope Mapping of Monoclonal Antibodies

In order to determine which region of the protein each monoclonal antibody of Example 2 was recognizing, 96 overlapping peptides were synthesized to cover the entire 1153 amino acid length structure of hiNOS. All peptides were 18 amino acids long (18-mers) and were synthesized as carboxyl terminal amides. Serine was substituted for all the naturally occurring cysteine residues in the structure, and each peptide had a six amino acid long overlap with its nearest neighbors, except the carboxyl terminal peptide which had an 11 amino acid overlap with the prior peptide. The peptides were used to epitope map the panel of monoclonal antibodies by ELISA techniques. Each peptide was used to sensitize a specific well on a series of microtiter plates. The culture supernatant or ascites from each monoclonal antibody was then applied individually to all the wells of a sensitized plate. The wells were then tested for the presence of bound mouse monoclonal antibody. Representative results that were obtained for this series of experiments are shown in FIGS. 2–6 and are summarized in Table IV, below:

TABLE IV

Epitope Mapping of Monoclonal Antibodies to hiNOS

| Monoclonal Antibody | Binds to | Sequence | Region |
|---|---|---|---|
| 1E8-B8 | G11 = PS-5183 | Gly Ile Val Pro Phe 5 | 985–1002 |
| | | Arg Ser Phe Trp Gln 10 | |
| | | Gln Arg Leu His Asp 15 | |
| | | Ser Gln His SEQ ID NO 24 | |
| 2A12-A4 | G11 = PS-5183 | Gly Ile Val Pro Phe 5 | 985–1002 |
| | | Arg Ser Phe Trp Gln 10 | |
| | | Gln Arg Leu His Asp 15 | |
| | | Ser Gln His SEQ ID NO 25 | |
| 6G12-H7 | A4 = PS-5104 | Ser Pro Val Thr Gln 5 | 37–54 |
| | | Asp Asp Leu Gln Tyr 10 | |
| | | His Asn Leu Ser Lys 15 | |
| | | Gln Gln Asn SEQ ID NO 26 | |
| 2D2-B2 | F6 = PS-5166 | Pro Ala Leu Val Gln 5 | 781–798 |
| | | Gly Ile Leu Glu Arg 10 | |
| | | Val Val Asp Gly Pro 15 | |

TABLE IV-continued

Epitope Mapping of Monoclonal Antibodies to hiNOS

| Monoclonal Antibody | Binds to | Sequence | Region |
|---|---|---|---|
| | | Thr Pro His<br>SEQ ID NO 27 | |
| 5B3-E6 | F6 =<br>PS-5166 | Pro Ala Leu Val Gln 5 | 781–798 |
| | | Gly Ile Leu Glu Arg 10 | |
| | | Val Val Asp Gly Pro 15 | |
| | | Thr Pro His<br>SEQ ID NO 27 | |
| 21C10-1D10 | A3 =<br>PS-5103 & | Asn Asn Asn Val Glu 5 | 25–42 |
| | | Lys Ala Pro Ser Ala 10 | |
| | | Thr Ser Ser Pro Val 15 | |
| | | Thr Gln Asp<br>SEQ ID NO 28 | |
| | A4 =<br>PS-5104 | Ser Pro Val Thr Gln 5 | 37–54 |
| | | Asp Asp Leu Gln Tyr 10 | |
| | | His Asn Leu Ser Lys 15 | |
| | | Gln Gln Asn<br>SEQ ID NO 29 | |
| 22E3-2F5 | F6 =<br>PS-5166 | Pro Ala Leu Val Gln 5 | 781–798 |
| | | Gly Ile Leu Glu Arg 10 | |
| | | Val Val Asp Gly Pro 15 | |
| | | Thr Pro His<br>SEQ ID NO 30 | |
| 24B10-2C7 | H1 =<br>PS-5185 | Arg Met Thr Leu Val 5 | 1009–1026 |
| | | Phe Gly Ser Arg Arg 10 | |
| | | Pro Asp Glu Asp His 15 | |
| | | Ile Tyr Gln<br>SEQ ID NO 31 | |

EXAMPLE 4

Epitope Mapping and Specificity Characterization With Synthetic Peptides

The sequence from each of the 18-mers to which monoclonal antibodies were found to bind (peptides A3, A4, F6, G11 and H1, Table IV) were used to design and make a series of epitope mapping peptides for these regions. Also, homologs to iNOS found by the BLAST search were employed to characterize the specificity of the iNOS monoclonal antibodies. A series of four truncation peptides from the amino terminal end of each of the 18-mers as well as a series of four truncations from the carboxyl terminal of each of the 18-mers were made. Each series deleted three amino acids in turn from either the carboxyl or amino terminal of the 18-mers. This resulted in two series of truncation peptides for each 18-mers which were successively shorter by three amino acids from each end. Table V and FIGS. 7A–7D and FIG. 8 list the truncation peptides and peptide homologs to hiNOS that were built, the latter were from regions of human nNOS, mouse and rat iNOS, and human eNOS, if any sequence homology was found to these regions by the BLAST computer search, hereinbefore discussed:

TABLE V

Truncated and Homolog Epitope Mapping Peptides

| Peptide | AA Segment | Sequence | Monoclonal Binding |
|---|---|---|---|
| PS-5103 | (A3) locus human iNOS (25–42) | Asn Asn Asn Val Glu 5 | 21C10-1D10+ |
| | | Lys Ala Pro Ser Ala 10 | |
| | | Thr Ser Ser Pro Val 15 | |
| | | Thr Gln Asp-amide<br>SEQ ID NO 32 | |
| PS-5241 | mouse iNOS (25–42) | Asn Asn Asn Val Lys 5 | weak |
| | | Lys Thr Pro Ser Ala 10 | |
| | | Val Leu Ser Pro Thr 15 | |
| | | Ile Gln Asp-amide<br>SEQ ID NO 33 | |
| PS-5242 | rat iNOS (25–42) | Asn Asn Asn Val Glu 5 | – |
| | | Lys Thr Pro Gly Ala 10 | |
| | | Ile Pro Ser Pro Thr 15 | |
| | | Thr Gln Asp-amide<br>SEQ ID NO 34 | |
| PS-5243 | human iNOS (28–42) | Val Glu Lys Ala Pro 5 | – |
| | | Ser Ala Thr Ser Ser 10 | |
| | | Pro Val Thr Gln | |
| | | Asp-amide 15<br>SEQ ID NO 35 | |
| PS-5244 | human iNOS (31–42) | Ala Pro Ser Ala Thr 5 | – |

TABLE V-continued

Truncated and Homolog Epitope Mapping Peptides

| Peptide | AA Segment | Sequence | Monoclonal Binding | |
|---|---|---|---|---|
| | | Ser Ser Pro Val Thr 10 | | |
| | | Gln Asp-amide SEQ ID NO 36 | | |
| PS-5245 | human iNOS (34–42) | Ala Thr Ser Ser Pro 5 | – | |
| | | Val Thr Gln Asp-amide SEQ ID NO 37 | | |
| PS-5246 | human iNOS (37–42) | Ser Pro Val Thr Gln 5 | – | |
| | | Asp-amide SEQ ID NO 38 | | |
| PS-5247 | human iNOS (25–39) | Asn Asn Asn Val Glu 5 | – | |
| | | Lys Ala Pro Ser Ala 10 | | |
| | | Thr Ser Ser Pro Val-amide 15 SEQ ID NO 39 | | |
| PS-5248 | human iNOS (25–36) | Asn Asn Asn Val Glu 5 | – | |
| | | Lys Ala Pro Ser Ala 10 | | |
| | | Thr Ser-amide SEQ ID NO 40 | | |
| P5-5249 | human iNOS (25–33) | Asn Asn Asn Val Glu 5 | – | |
| | | Lys Ala Pro Ser-amide SEQ ID NO 41 | | |
| PS-5250 | human iNOS (25–30) | Asn Asn Asn Val Glu 5 | – | |
| | | Lys-amide SEQ ID NO 42 | | |
| PS-5104 | (A4) locus human iNOS (37–54) | Ser Pro Val Thr Gln 5 | 6G12 –H7+ | 21C10- 1D10+ |
| | | Asp Asp Leu Gln Tyr 10 | | |
| | | His Asn Leu Ser Lys 15 | | |
| | | Gln Gln Asn-amide SEQ ID NO 43 | | |
| PS-5261 | human iNOS (40–54) | Thr Gln Asp Asp Leu 5 | + | – |
| | | Gln Tyr His Asn Leu 10 | | |
| | | Ser Lys Gln Gln | | |
| | | Asn-amide 15 SEQ ID NO 44 | | |
| PS-5262 | human iNOS (43–54) | Asp Leu Gln Tyr His 5 | weak | – |
| | | Asn Leu Ser Lys Gln 10 | | |
| | | Gln Asn-amide SEQ ID NO 45 | | |
| PS-5263 | human iNOS (46–54) | Tyr His Asn Leu Ser 5 | – | – |
| | | Lys Gln Gln Asn-Amide SEQ ID NO 46 | | |
| PS-5264 | human iNOS (49–54) | Leu Ser Lys Gln Gln 5 | – | – |
| | | Asn-amide SEQ ID NO 47 | | |
| PS-5265 | human iNOS (37–51) | Ser Pro Val Thr Gln 5 | + | + |
| | | Asp Asp Leu Gln Tyr 10 | | |
| | | His Asn Leu Ser Lys-amide 15 SEQ ID NO 48 | | |
| PS-5266 | human iNOS (37–48) | Ser Pro Val Thr Gln 5 | – | – |
| | | Asp Asp Leu Gln Tyr 10 | | |
| | | His Asn-amide SEQ ID NO 49 | | |
| PS-5267 | human iNOS (37–45) | Ser Pro Val Thr Gln 5 | – | – |
| | | Asp Asp Leu Gln-amide SEQ ID NO 50 | | |
| PS-5268 | human iNOS (37–42) | Ser Pro Val Thr Gln 5 | – | – |
| | | Asp-amide SEQ ID NO 51 | | |
| PS-5166 | (F6) locus human iNOS (781–798) | Pro Ala Leu Val Gln 5 | 2D2-B2+ | |
| | | Gly Ile Leu Glu Arg 10 | | |

TABLE V-continued

Truncated and Homolog Epitope Mapping Peptides

| Peptide | AA Segment | Sequence | Monoclonal Binding |
|---|---|---|---|
| | | Val Val Asp Gly Pro 15 | |
| | | Thr Pro His-amide SEQ ID NO 52 | |
| PS-5221 | human eNOS (806–824) | Pro Gly Leu Val Glu 5 | – |
| | | Ala Leu Leu Ser Arg 10 | |
| | | Val Glu Asp Pro Pro 15 | |
| | | Ala Pro Thr Glu-amide SEQ ID NO 53 | |
| PS-5222 | human INOS (784–798) | Val Gln Gly Ile Leu 5 | + |
| | | Glu Arg Val Val Asp 10 | |
| | | Gly Pro Thr Pro His-amide 15 SEQ ID NO 54 | |
| PS-5223 | human iNOS (787–798) | Ile Leu Glu Arg Val 5 | – |
| | | Val Asp Gly Pro Thr 10 | |
| | | Pro His-amide SEQ ID NO 55 | |
| PS-5224 | human iNOS (790–798) | Arg Val Val Asp Gly 5 | – |
| | | Pro Thr Pro His-amide SEQ ID NO 56 | |
| PS-5225 | human iNOS (793–798) | Asp Gly Pro Thr Pro 5 | – |
| | | His-amide SEQ ID NO 57 | |
| PS-5226 | human iNOS (781–794) | Pro Ala Leu Val Gln 5 | + |
| | | Gly Ile Leu Glu Arg 10 | |
| | | Val Val Asp Gly-amide SEQ ID NO 58 | |
| P5-5227 | human iNOS (781–792) | Pro Ala Leu Val Gln 5 | + |
| | | Gly Ile Leu Glu Arg 10 | |
| | | Val Val-amide SEQ ID NO 59 | |
| PS-5228 | human iNOS (781–789) | Pro Ala Leu Val Gln 5 | weak |
| | | Gly Ile Leu Glu-amide SEQ ID NO 60 | |
| PS-5229 | human iNOS (781–786) | Pro Ala Leu Val Gln 5 | – |
| | | Gly-amide SEQ ID NO 61 | |
| PS-5183 | (G11) locus human iNOS (985–1002) | Gly Ile Val Pro Phe 5 | 1E8- 2A12- B8+ A4+ |
| | | Arg Ser Phe Trp Gln 10 | |
| | | Gln Arg Leu His Asp 15 | |
| | | Ser Gln His-amide SEQ ID NO 62 | |
| PS-5201 | Human nNOS (1256–1273) | Gly Ile Ala Pro Phe 5 | +    + |
| | | Arg Ser Phe Trp Gln 10 | |
| | | Gln Arg Gln Phe Asp 15 | |
| | | Ile Gln His-amide SEQ ID NO 63 | |
| PS-5202 | human eNOS (1017–1031) | Gly Ile Ala Pro Phe 5 | –    – |
| | | Arg Gly Phe Trp Gln 10 | |
| | | Glu Arg Leu His Asp-amide 15 SEQ ID NO 64 | |
| PS-5203 | human iNOS (988–1002) | Pro Phe Arg Ser Phe 5 | weak    + |
| | | Trp Gln Gln Arg Leu 10 | |
| | | His Asp Ser Gln His-amide 15 SEQ ID NO 65 | |
| PS-5204 | human iNOS (991–1002) | Ser Phe Trp Gln Gln 5 | –    – |
| | | Arg Leu His Asp Ser 10 | |
| | | Gln His-amide SEQ ID NO 66 | |

TABLE V-continued

Truncated and Homolog Epitope Mapping Peptides

| Peptide | AA Segment | Sequence | Monoclonal Binding |
|---|---|---|---|
| PS-5205 | human iNOS (994–1002) | Gln Gln Arg Leu His 5<br><br>Asp Ser Gln His-<br><br>amide<br>SEQ ID NO 67 | – |
| PS-5206 | human iNOS (997–1002) | His Asp Ser Gln<br><br>His-amide<br>5<br>SEQ ID NO 68 | – |
| PS-5207 | human iNOS (985–998) | Gly Ile Val Pro Phe 5<br><br>Arg Ser Phe Trp Gln 10<br><br>Gln Arg Leu His<br><br>Asp-amide<br>15<br>SEQ ID NO 69 | – |
| PS-5208 | human iNOS (985–996) | Gly Ile Val Pro Phe 5<br><br>Arg Ser Phe Trp Gln 10<br><br>Gln Arg-amide<br>SEQ ID NO 70 | – |
| PS-5209 | human iNOS (985–993) | Gly Ile Val Pro Phe 5<br><br>Arg Ser Phe Trp-<br><br>amide<br>SEQ ID NO 71 | – |
| PS-5210 | human iNOS (985–990) | Gly Ile Val Pro Phe 5<br><br>Arg-amide<br>SEQ ID NO 72 | – |
| PS-5185 | (H1) locus human iNOS (1009–1026) | Arg Met Thr Leu Val 5<br><br>Phe Gly Ser Arg Arg 10<br><br>Pro Asp Glu Asp His 15<br><br>Ile Tyr Gln-amide<br>SEQ ID NO 73 | 24B10-2C7+ |
| PS-5281 | human eNOS (1041–1057) | Met Thr Leu Val Phe 5<br><br>Gly Ser Arg Ser Ser 10<br><br>Gln Leu Asp His Leu 15<br><br>Tyr Arg-amide<br>SEQ ID NO 74 | – |
| PS-5282 | human nNOS (1281–1297) | Met Val Leu Val Phe 5<br><br>Gly Ser Arg Gln Ser 10<br><br>Lys Ile Asp His Ile 15<br><br>Tyr Arg-amide<br>SEQ ID NO 75 | – |
| PS-5283 | human iNOS (1012–1026) | Leu Val Phe Gly Ser 5<br><br>Arg Arg Pro Asp Glu 10<br><br>Asp His Ile Tyr<br><br>Gln-amide<br>15<br>SEQ ID NO 76 | + |
| PS-5284 | human iNOS (1015–1026) | Gly Ser Arg Arg Pro 5<br><br>Asp Glu Asp His Ile 10<br><br>Tyr Gln-amide<br>SEQ ID NO 77 | + |
| PS-5285 | human iNOS (1018–1026) | Arg Pro Asp Glu Asp 5<br><br>His Ile Tyr Gln-<br><br>amide<br>SEQ ID NO 78 | weak |
| PS-5286 | human iNOS (1021–1026) | Glu Asp His Ile Tyr 5<br><br>Gln-amide<br>SEQ ID NO 79 | – |
| PS-5287 | human iNOS (1009–1023) | Arg Met Thr Leu Val 5<br><br>Phe Gly Ser Arg Arg 10<br><br>Pro Asp Glu Asp<br><br>His-amide<br>15<br>SEQ ID NO 80 | – |
| PS-5288 | human iNOS (1009–1020) | Arg Met Thr Leu Val 5<br><br>Phe Gly Ser Arg Arg 10<br><br>Pro-amide<br>SEQ ID NO 81 | – |

TABLE V-continued

Truncated and Homolog Epitope Mapping Peptides

| Peptide | AA Segment | Sequence | Monoclonal Binding |
|---|---|---|---|
| PS-5289 | human iNOS (1009–1017) | Arg Met Thr Leu Val Phe Gly Ser Arg-amide SEQ ID NO 82 | – 5 |
| PS-5290 | human iNOS (1009–1014) | Arg Met Thr Leu Val Phe-amide SEQ ID NO 83 | – 5 |

Where "+" represents positive binding, "–" represents no binding, and "weak" represents binding at only very high monoclonal antibody concentrations.

The ability of the monoclonal antibodies to bind to the various truncation analogues or to the nNOS and eNOS analogues were tested by ELISA in a similar format to that which was used to screen the original ninety-six 18-mers.

At the A-3 locus, monoclonal antibody 21C10-1D10 would only bind strongly to peptide A-3 (PS-5103) and weakly to the mouse homolog miNOS (25–42), (PS-5241). 21C10-1D10 would not bind to any of the truncated peptides nor to the rat homolog riNOS (25–42), (PS-5242).

At the A4 locus, two monoclonal antibodies were determined to bind during the initial screening (6G12-H7 and 21C10-1D10). These showed differing specificities to the truncated peptides. Monoclonal antibody 6G12-H7 was found to bind strongly to A4 (PS-5104), and two truncated analogues, PS-5261 and PS-5265: it also bound weakly to PS-5262. This shows that the original 18-mers should be able to be shortened to at least a 12-mers with the sequence Thr Gln Asp Asp Leu Gln Tyr His Asn Leu Ser Lys SEQ ID NO 84 and still be able to bind to this peptide analogue of the whole protein. In contrast, monoclonal antibody 21C10-1D10 bound only to the original 18-mer A4 (PS-5104) and to the hiNOS (37–51) peptide sequence (PS-5265), which is truncated three residues on the carboxyl terminus.

At the F6 locus, monoclonal antibody 2D2-B2 was found to bind strongly peptide F6 (PS-5166) and three of its truncated analogues, PS-5222, PS-5226, and PS-5227. It bound PS5228 weakly and to the human eNOS (806–824), PS-5221, not at all. However, from the results obtained with the truncation peptides, the epitope should be contained in the sequence Val Gln Gly Ile Leu Glu Arg Val Val SEQ ID NO 85.

At the G-11 locus, two monoclonal antibodies were found to bind during the initial screening, 1E8-B8 and 2A12-A4. When these two were tested for binding to the truncation series and two homologs, a similar pattern of recognition was found for both monoclonals. Both bound strongly to peptide G-11 (PS-5183), as expected, and both recognized the homolog human nNOS (1256–1273), PS-5201, though the binding was much less than for G-11. Each recognized PS-5203, the first of the amino terminal truncation series peptides, but the binding of 1E8-B8 was much weaker than that observed for 2A12-A4.

Finally, at the H1 locus, monoclonal antibody 24B10-2C7 was found to bind to H1 (PS-5185). This monoclonal did not recognize either the human eNOS or nNOS homologs, PS-5281 and PS-5282, respectively, but it did bind strongly to the first two amino terminal truncation series peptides, PS-5283 and PS-5284. Monoclonal 24B10-2C7 also bound weakly to the next shorter amino terminal truncation peptide, PS-5285. These results indicate that this monoclonal antibody recognized a sequence located in the carboxyl terminal region of peptide H-1 (PS-5185).

EXAMPLE 5

Sandwich ELISA to Determine Quantity of hiNOS in Samples

Figure 9:
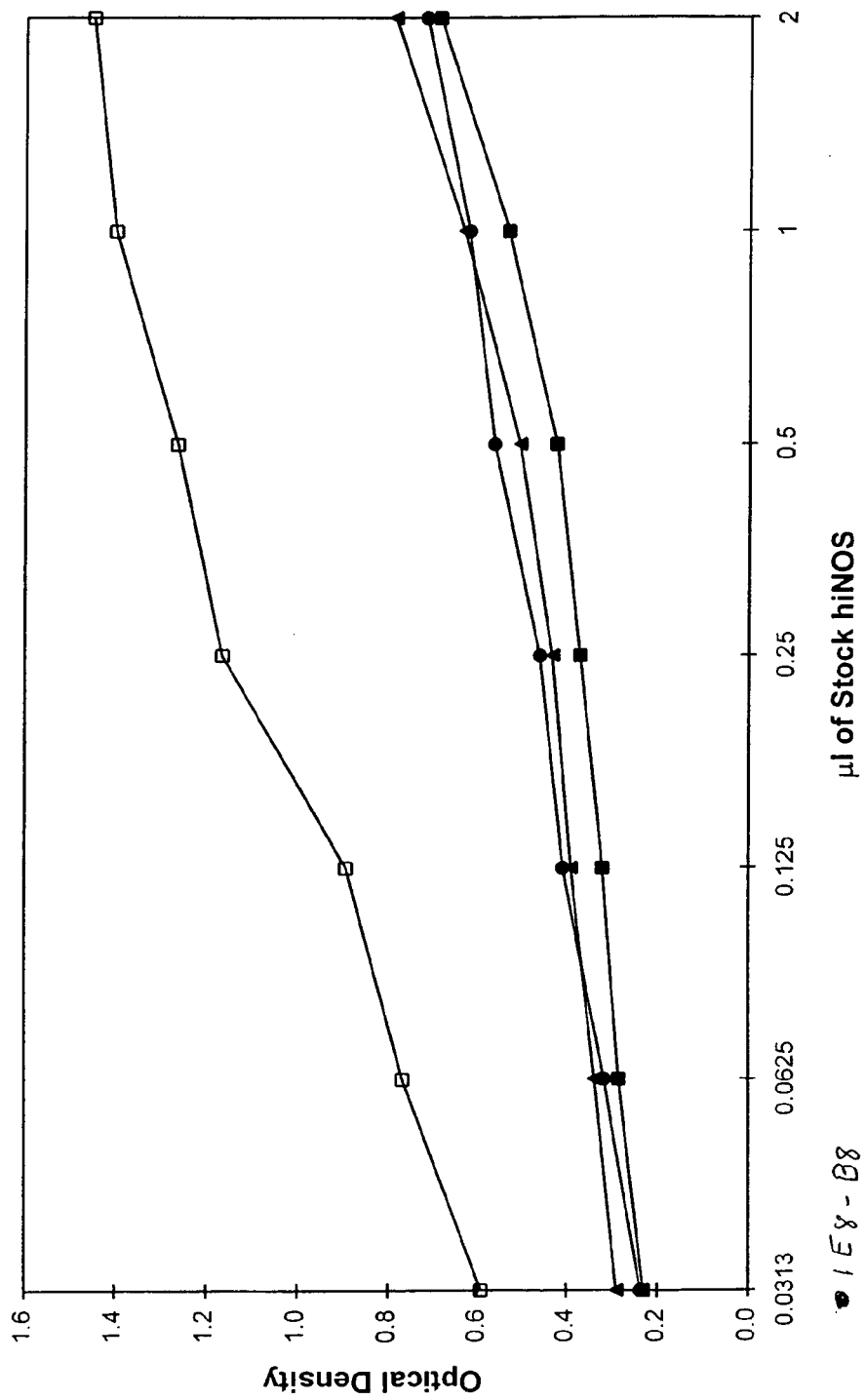
FIG. 9 is a graph representing a sandwich ELISA that measures hiNOS using polyclonal rabbit anti-peptide antibodies and four mouse monoclonal antibodies.
Figure 10:
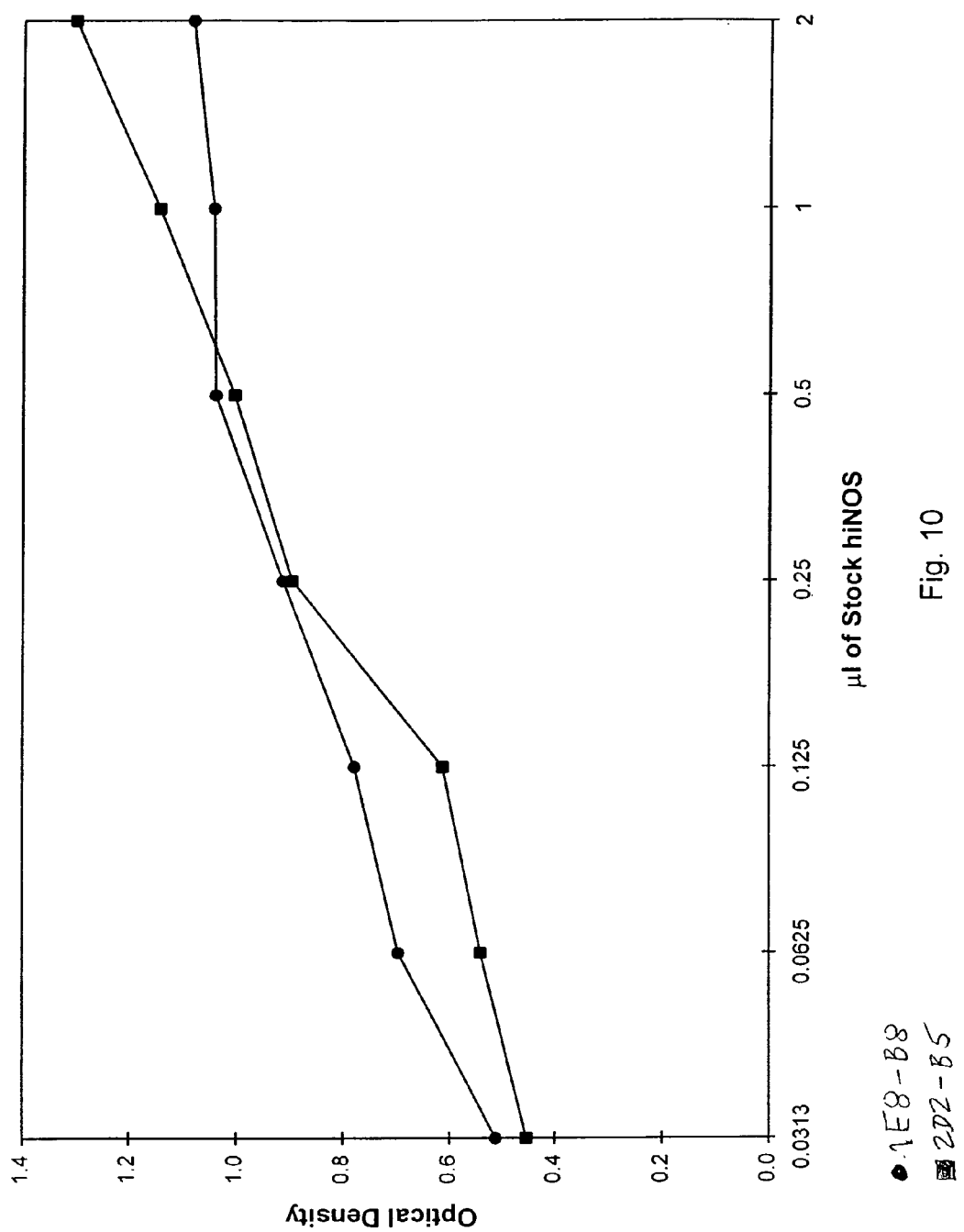
FIG. 10 is a graph representing a sandwich ELISA that measures hiNOS using mouse IgG2b monoclonal antibody 21C10-1D10 and two mouse $IgG_1$ monoclonal antibodies.
Figure 11:
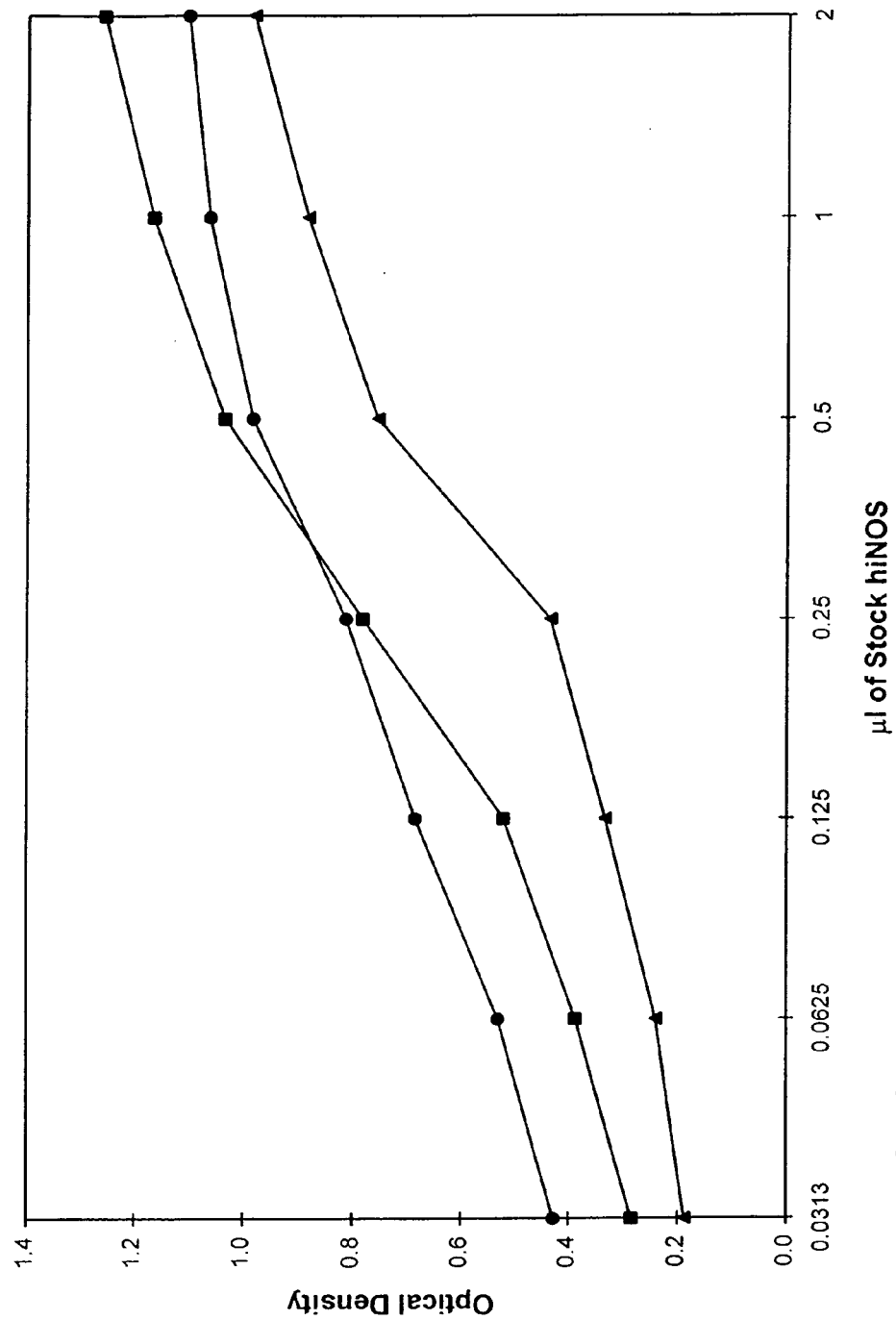
FIG. 11 is a graph representing a sandwich ELISA that measures hiNOS using mouse IgM monoclonal antibody 7D8-B3 and three mouse IgG monoclonal antibodies.

Polyclonal rabbit anti peptide iNOS antisera was used as a "catch" antibody in the initial attempt to develop a sandwich ELISA for hiNOS. In this format affinity purified goat anti-rabbit IgG at 1 µgm per well in 100 µl was used to sensitize microliter plates. Following this the plates were blocked with bovine serum albumin (BSA). Rabbit polyclonal anti-peptide antibody (specific for the carboxyl terminal of hiNOS) was added and allowed to bind. This was used as "catch" antibody to bind hiNOS in samples. Various mouse monoclonal from the panel of Table III were tested for their ability to detect and/or quantitate hiNOS in samples, illustrated in FIG. 9. The results shows that clones 1E8-B8, 21C10-1D10, 2A1-A4, and 7D8-B3 were found to work in this assay format. However, in order to eliminate the necessity of repeatedly producing polyclonal rabbit antipeptide antibody, which needs extensive characterization, a sandwich ELISA was designed using monoclonal antibodies from the panel developed to hiNOS, Table III, as both the "catch" and detection antibodies. In this assay format affinity purified goat anti-mouse $IgG_{2A}$, $IgG_{2B}$, or IgM was used to sensitize the microtiter plates. The "catch" monoclonal antibody was then added; either 2A1-F8, 6A12-A12, 21C10-1D10, or one of IgM class monoclonals. The plate was then blocked with BSA. Samples known to contain hiNOS were then applied to the microtiter plates. Following this, they were then thoroughly washed. The detection monoclonal antibody used was one from a different immunoglobulin class. In the case of monoclonal antibody 21C10-1D10, which is an $IgG_{2b}$, mouse $IgG_1$ monoclonal antibodies were used as detection antibodies, for example 1E8-B8 and 2D2-B2, shown in FIG. 10. In the case of the "catch" monoclonal antibody being an IgM class antibody, any of the mouse IgG clones could be used as detection antibody; this includes 1E8-B8 (IgG1), 2D2-B2 ($IgG_1$), and 21C10-1D10 (IgG2B), per FIG. 11. As is evident, a monoclonal based antibody sandwich ELISA can be produced using the panel of monoclonal antibodies of Table III. The necessity for using a polyclonal "catch" antibody can be eliminated by employing different immunoglobulin class monoclonal antibodies from the panel of mouse monoclonal antibodies developed to hiNOS.

EXAMPLE 6

Western Immunoblots

Figure 12:
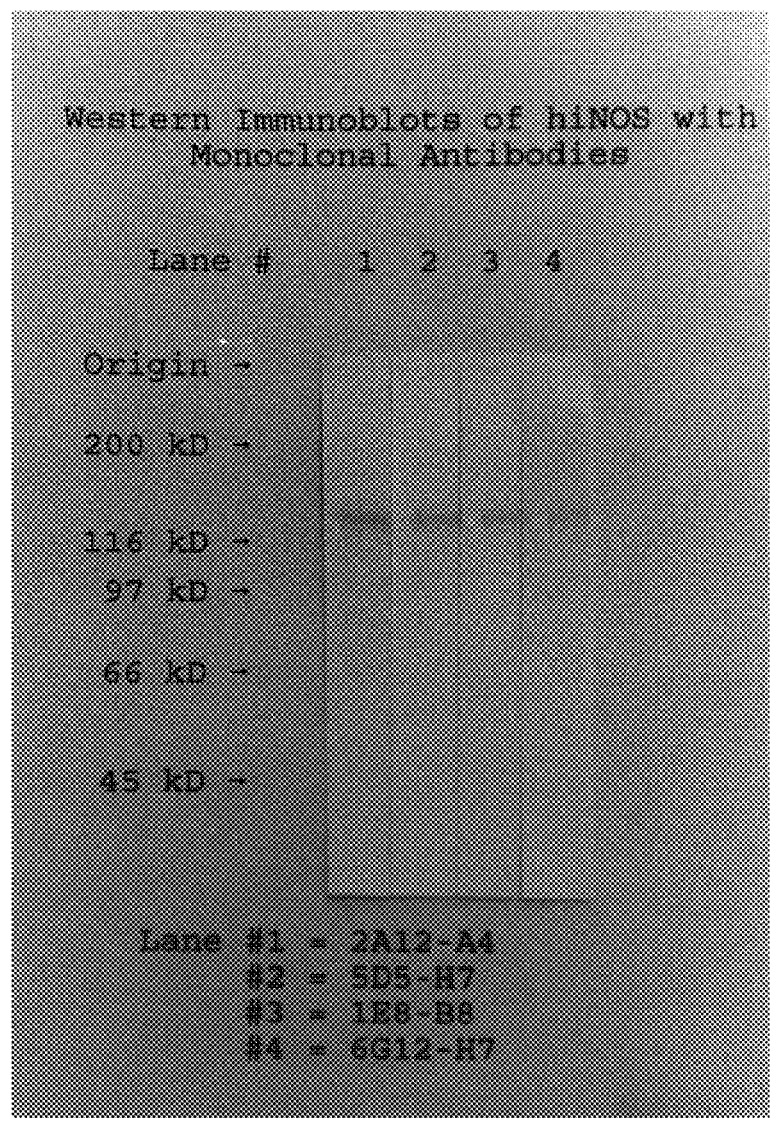
FIG. 12 is a photograph of a western immunoblot of hiNOS using four different primary monoclonal antibodies and HRP-conjugated goat anti-mouse IgG secondary antibody.

In addition to use in sandwich ELISAs, the panel of monoclonal antibodies of Table III was tested for their ability to detect hiNOS in samples by western immunoblot techniques. Samples were electrophoresed on 7.5% SDS-PAGE gels which separates the proteins by molecular weight. The proteins were transferred onto PVDF membranes, and the membranes were blocked with evaporated goats milk diluted 1:4 with PBS/Tween 20 buffer. The primary anti-hiNOS monoclonal antibodies were bound, and then the membranes were developed using HRP-conjugated goat anti-mouse IgG antibody, shown in FIG. 12. The monoclonal antibodies have also been tested in western blots using cell lysates obtained from cells which have been reported to contain iNOS following induction with cytokine/LPS mix. Cell lines A-172 and RAW 264.7 were purchased from American Type Culture Collection of Rockville, Md. (ATCC), were expanded, and cells were harvested before and after induction with a cytokine/LPS mix, FIGS. 13 and 14. Such cytotoxic mix is described in the Geller et al., article, hereinbefore noted, as a cytokine/LPS mixture. The cell pellets were thoroughly washed after harvesting with PBS to remove extraneous proteins. The cells were lysed by two freeze-thaw cycles and sonification. The cell lysates were diluted 1:2 with SDS-PAGE sample buffer and boiled for ten minutes. The samples were electrophoresed on 7.5% gels as described above. The uninduced cells did not contain iNOS whereas, after induction with the cytokine/LPS mix, a band at 130 kd was present. This shows that the cytokine/LPS mix had induced iNOS and that the monoclonal antibodies of Table III can detect iNOS in unknown samples in the western blot format.

Figure 13:
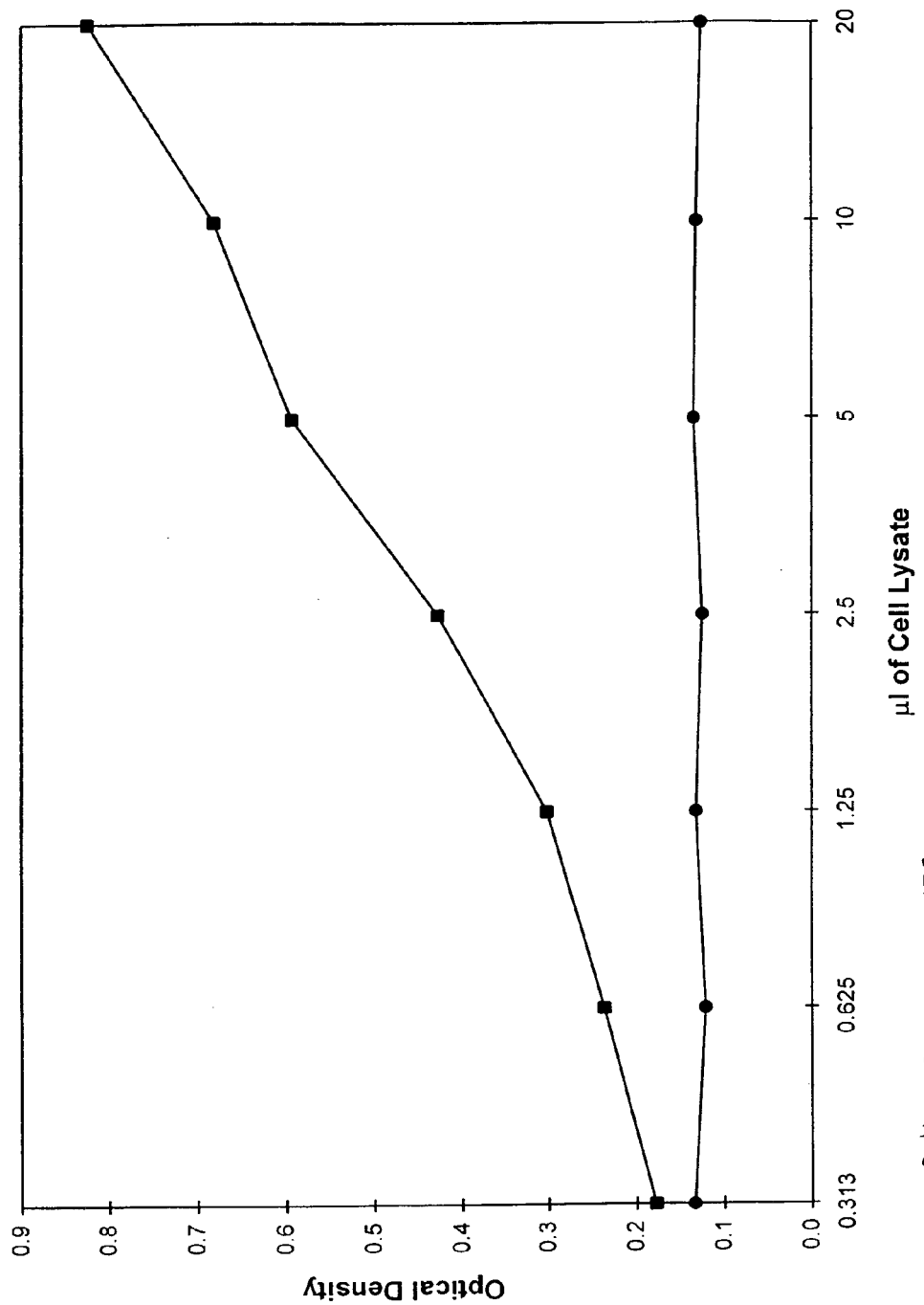
FIG. 13 is a graph representing a sandwich ELISA that measures hiNOS in non-induced and induced A-172 cell lysates using a mouse IgM monoclonal catch antibody, 7D8-B3, and a mouse $IgG_1$ monoclonal detection antibody, 1E8-B8.
Figure 14:
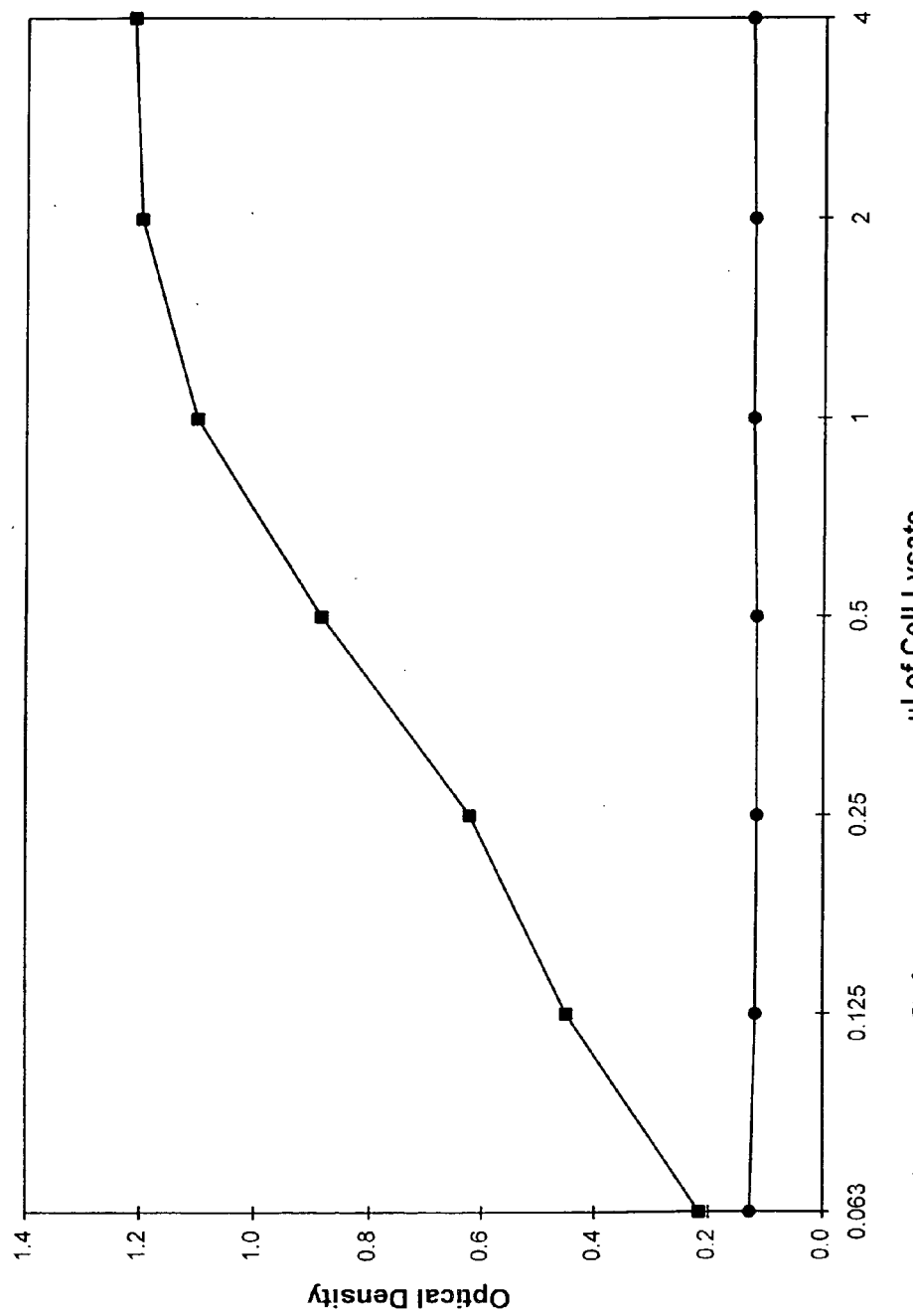
FIG. 14 is a graph representing a sandwich ELISA that measures iNOS in non-induced and induced RAW 264.7 cell lysates using mouse IgM monoclonal catch antibody, 7D8-B3, and mouse $IgG_1$ monoclonal detection antibody, 1E8-B8.

In addition to examining these induced cell lysates by western immunoblots, they were tested by the sandwich ELISA procedure of Example 5 to determine if iNOS could be detected and/or quantitated. The results of such ELISA tests as illustrated in FIGS. 13 and 14 clearly indicated no iNOS was present in the uninduced cells, whereas after induction with the cytokine/LPS mix a substantial amount of iNOS was present.

EXAMPLE 7

Immunofluorescent Staining of Induced Cells

Figure 15:
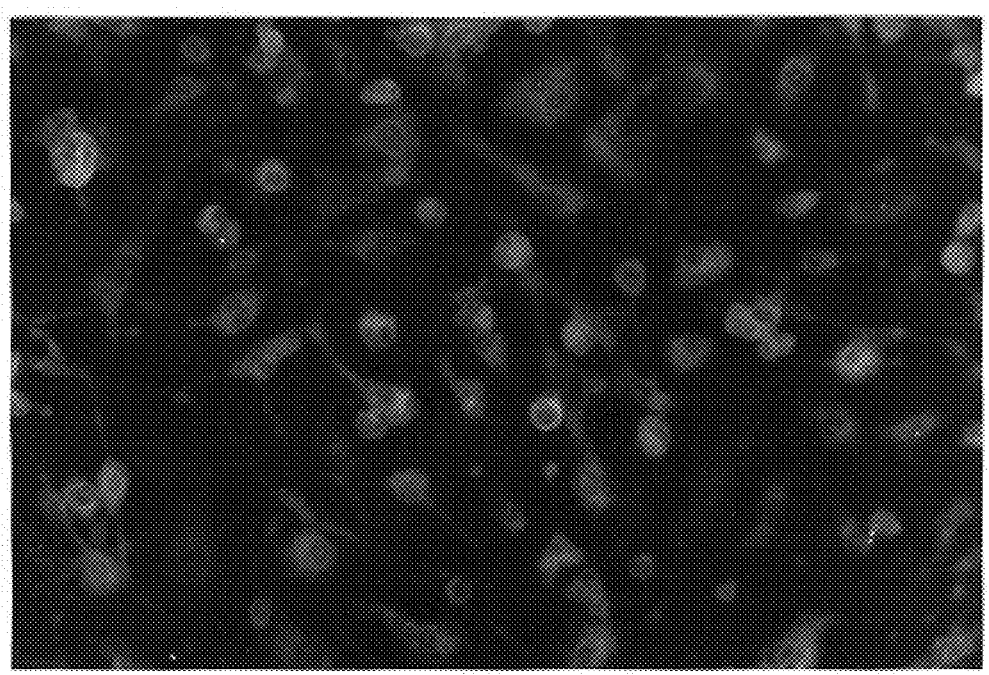
FIG. 15 is a photograph showing the indirect immunofluorescent staining of induced A-172 cells with mouse $IgG_1$ monoclonal antibody 1E8-B8 magnified 1600×.
Figure 16:
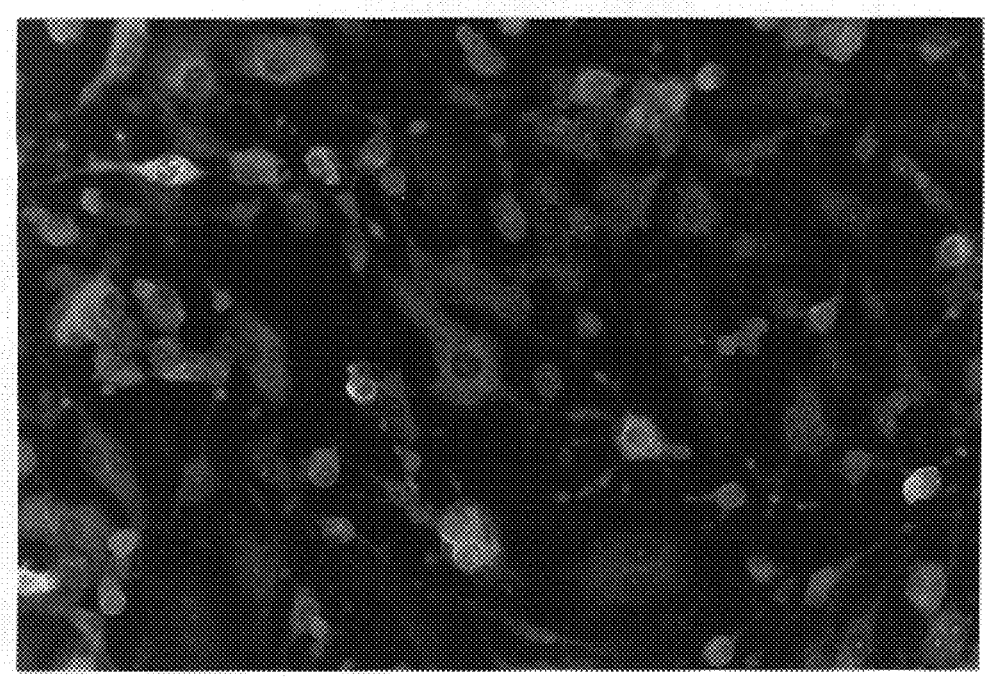
FIG. 16 is a photograph showing the indirect immunofluorescent staining of induced A-172 cells with mouse $IgG_1$ monoclonal antibody 2A12-A4 magnified 1600×.
Figure 17:
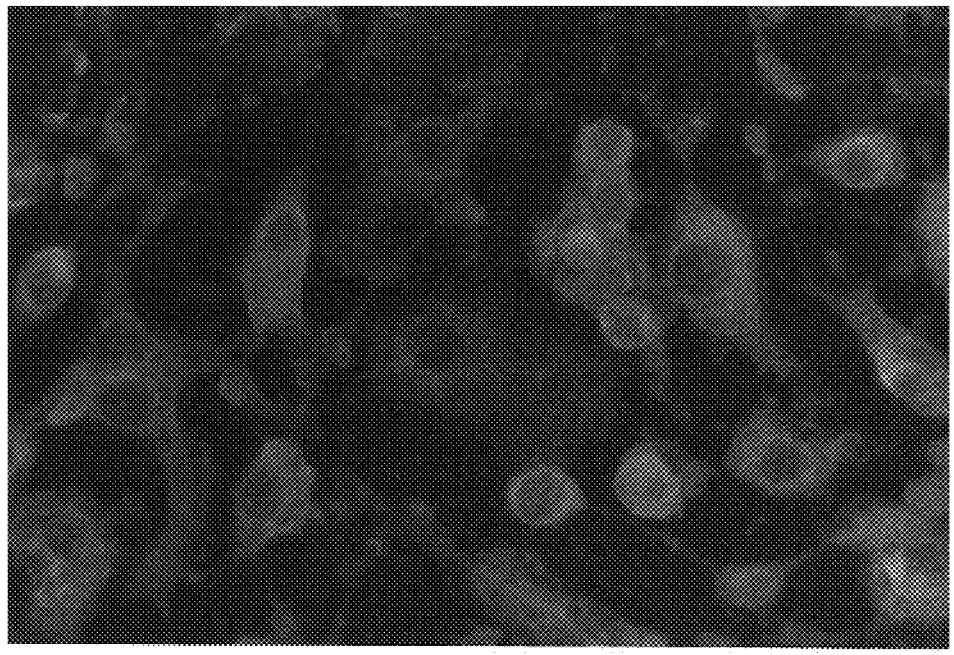
FIG. 17 is a photograph showing the indirect immunofluorescent staining of induced A-172 cells with mouse IgM monoclonal antibody 2H11-D11 magnified 1600×.
Figure 18:
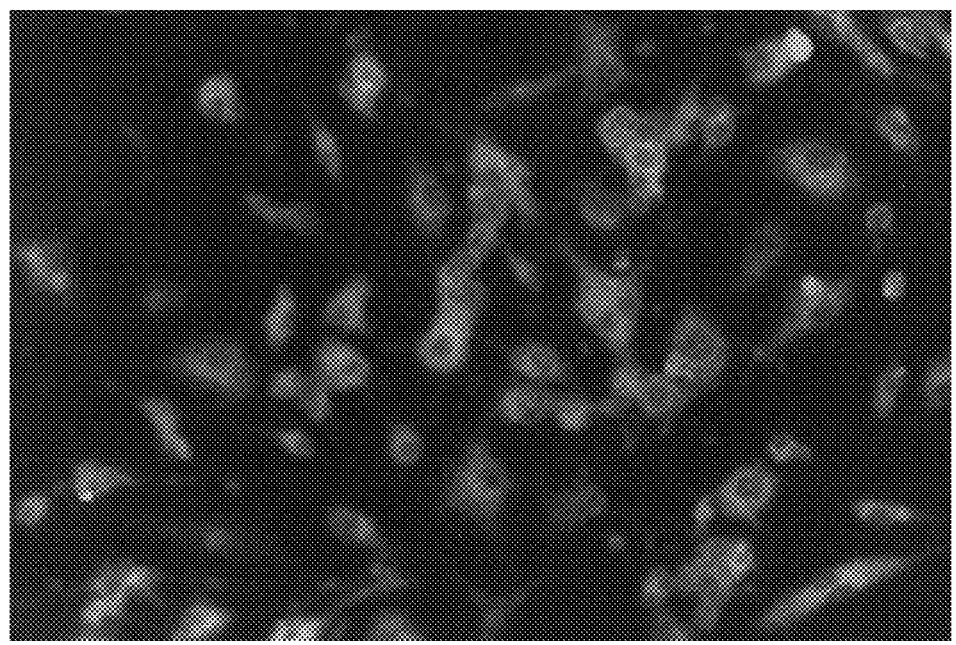
FIG. 18 is a photograph showing the indirect immunofluorescent staining of induced RAW 264.7 cells with mouse $IgG_1$ monoclonal antibody 1E8-B8 magnified 1600×.
Figure 19:
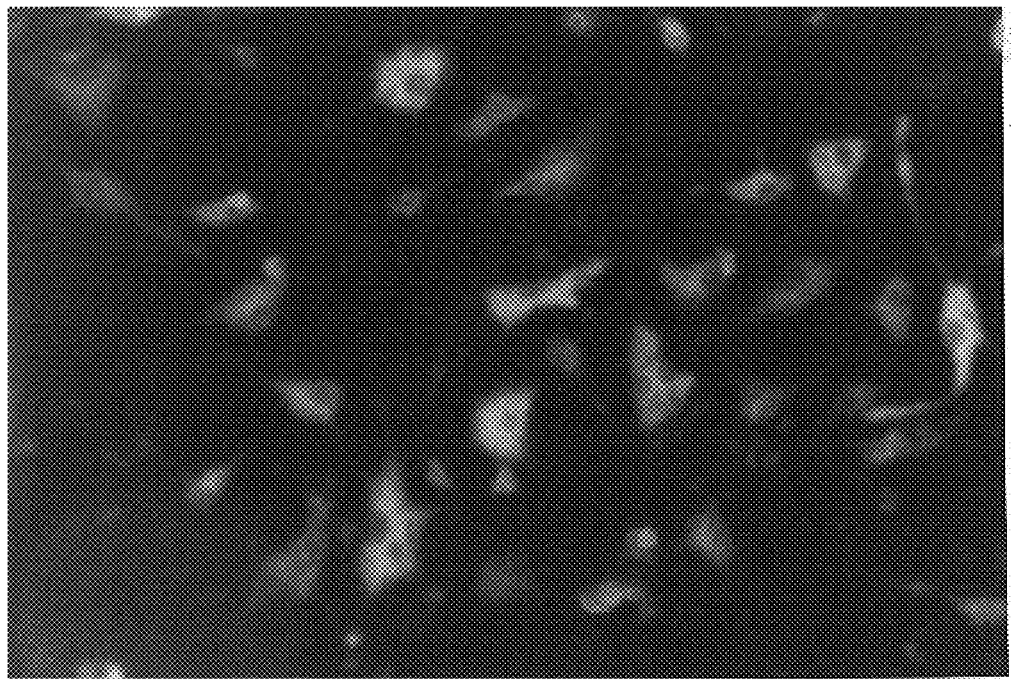
FIG. 19 is a photograph showing the indirect immunofluorescent staining of induced RAW 264.7 cells with mouse $IgG_1$ monoclonal antibody 2A12-A4 magnified 1600×.
Figure 20:
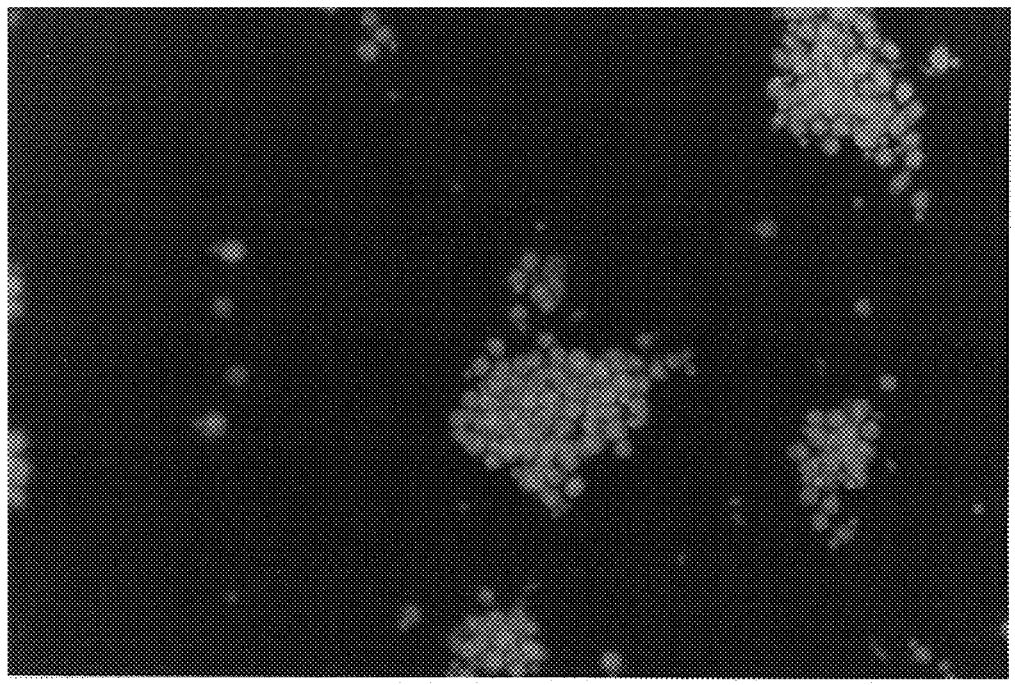
FIG. 20 is a photograph showing the indirect immunofluorescent staining of induced human monocytes with mouse $IgG_1$ monoclonal antibody 1E8-B8 magnified 1600×.
Figure 21:
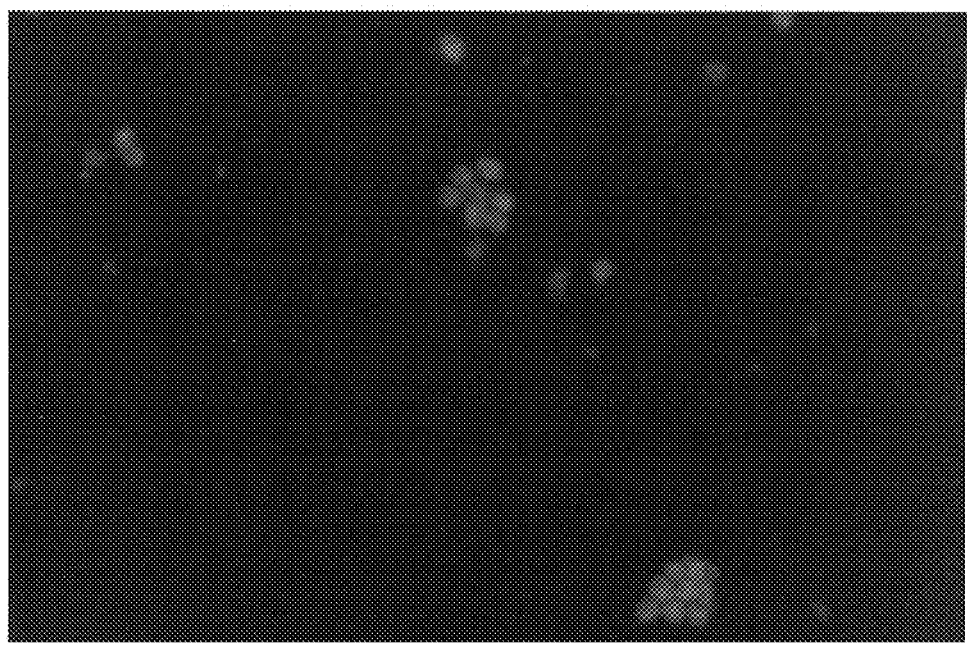
FIG. 21 is a photograph showing the indirect immunofluorescent staining of induced human monocytes with mouse $IgG_1$ monoclonal antibody 2A12-A4 magnified 1600×.
Figure 22:
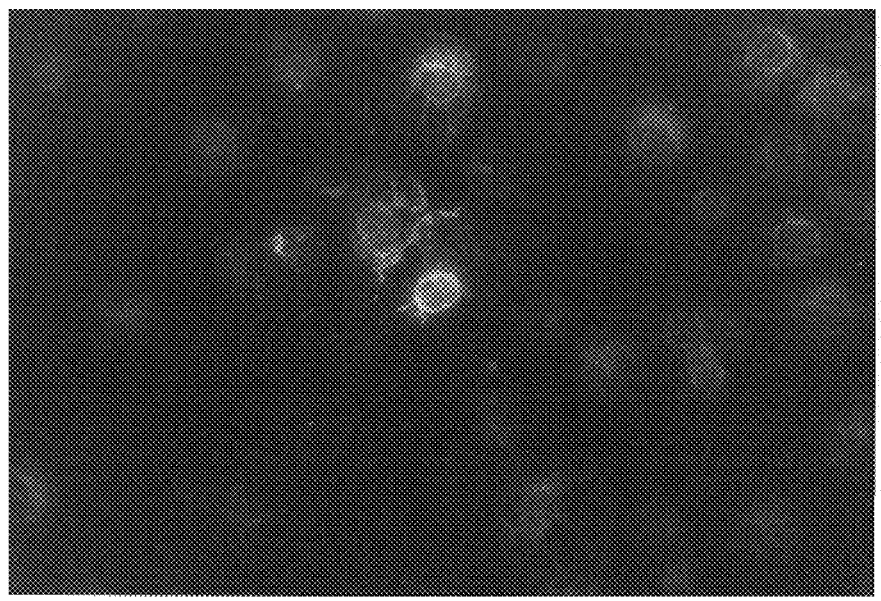
FIG. 22 is a photograph of mouse peritoneal cavity lavage cells 16 hrs. after induction with lipopolysaccharide showing indirect immunofluorescent staining of iNOS with mouse $IgG_1$ kappa monoclonal antibodies 5B3-E6 magnified 800×.
Figure 23:
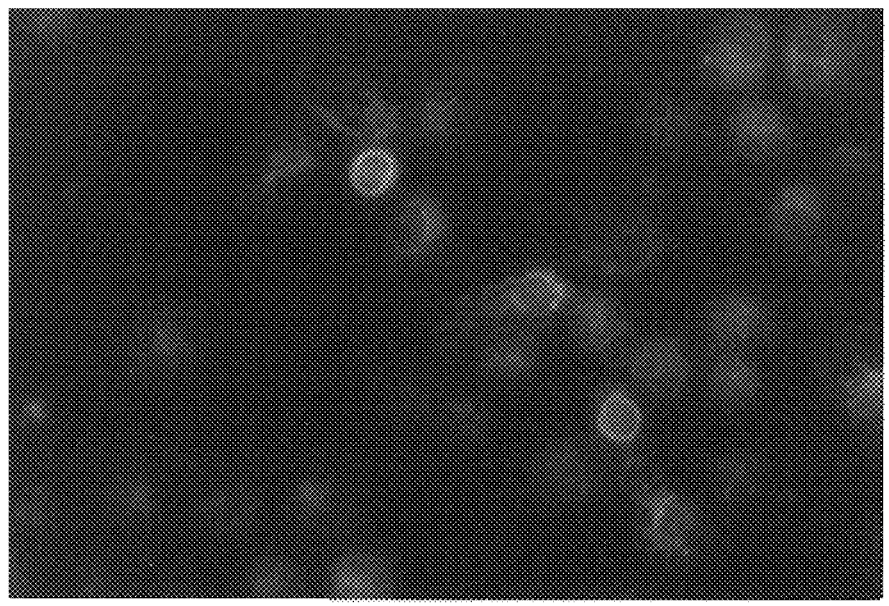
FIG. 23 is a photograph of mouse peritoneal cavity lavage cells 16 hrs. after induction with lipopolysaccharide showing indirect immunofluorescent staining of iNOS with mouse $IgG_1$ kappa monoclonal antibodies 2D2-B2 magnified 800×.
Figure 24:
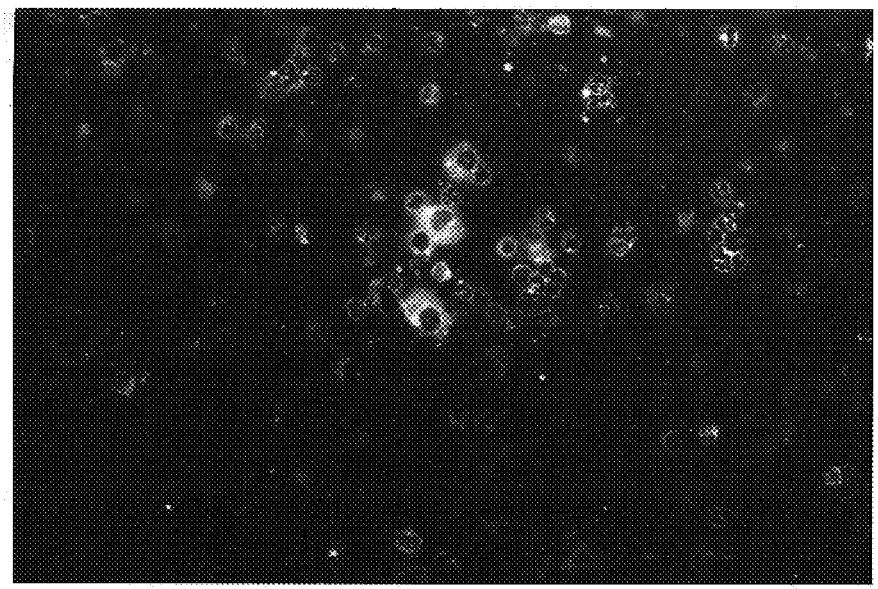
FIG. 24 is a photograph of mouse buffy coat cells 12 hours after induction with lipopolysaccharide showing indirect immunofluorescent staining of iNOS with mouse $IgG_1$ kappa monoclonal antibodies 5B3-E6 magnified 800×.
Figure 25:
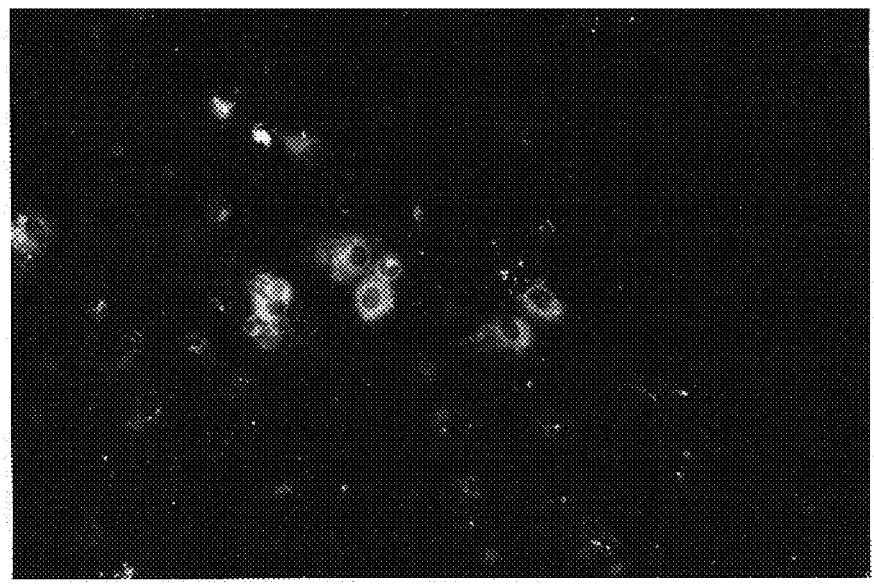
FIG. 25 is a photograph of mouse buffy coat cells 12 hours after induction with lipopolysaccharide showing indirect immunofluorescent staining of iNOS with mouse $IgG_1$ kappa monoclonal antibodies 2D2-B2 magnified 800×.
Figure 26:
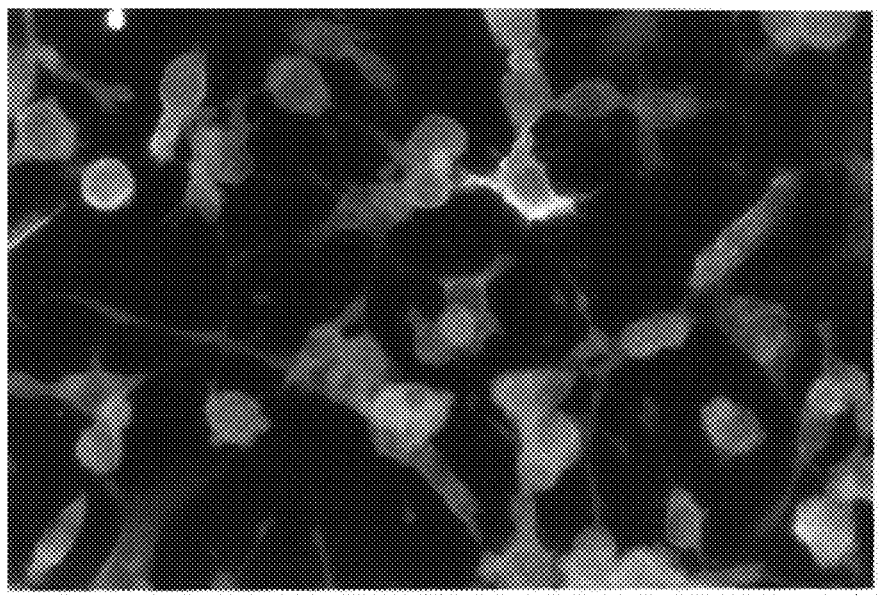
FIG. 26 is a photograph of human A-172 cells 40 hours after induction with CM/LPS showing indirect immunofluorescent staining of hiNOS with mouse $IgG_1$ kappa monoclonal antibodies 5B3-E6 magnified 1600×.
Figure 27:
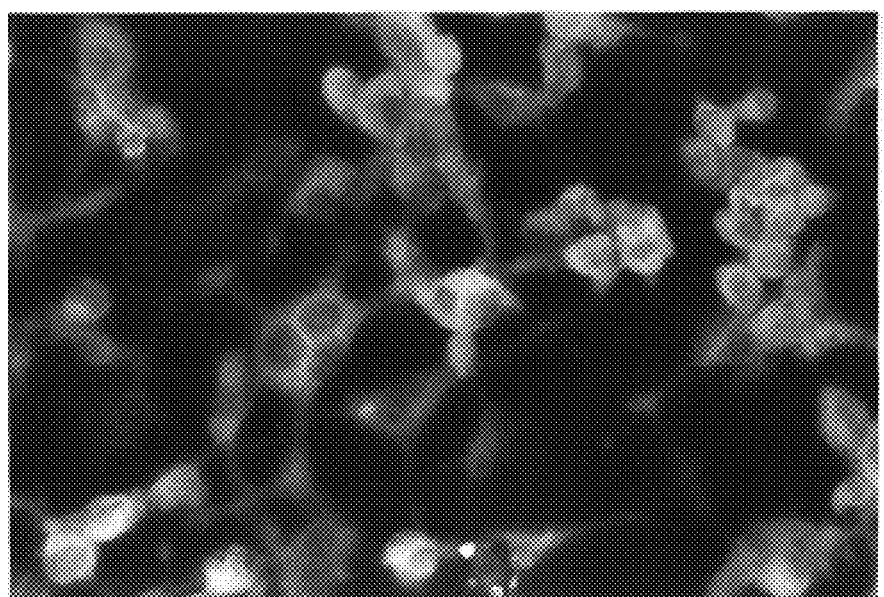
FIG. 27 is a photograph of human A-172 cells 40 hours after induction with CM/LPS showing indirect immunofluorescent staining of hiNOS with mouse $IgG_1$ kappa monoclonal antibodies 2D2-B2 magnified 1600×.
Figure 28:
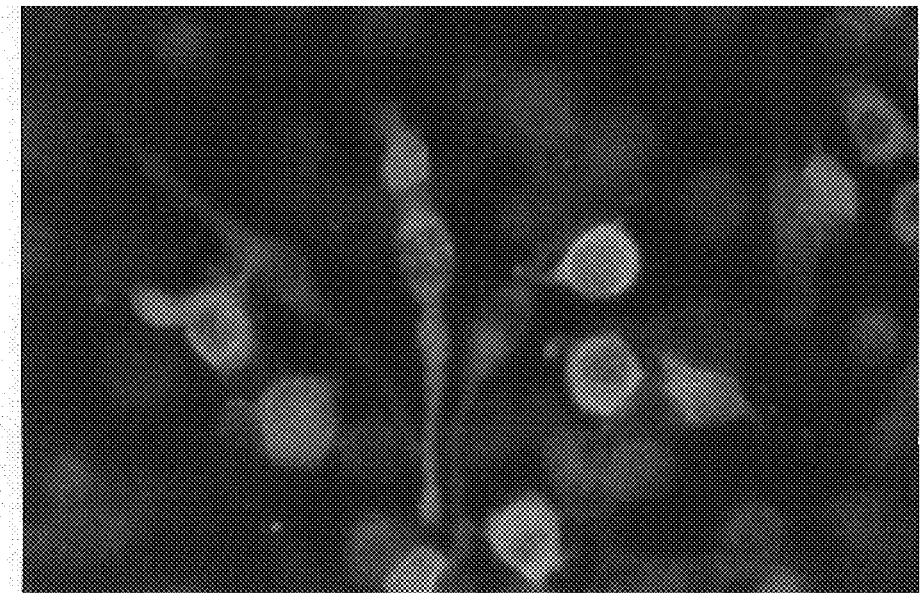
FIG. 28 is a photograph of mouse RAW 264.7 cells 40 hours after induction with CM/LPS showing indirect immunofluorescent staining of iNOS with mouse $IgG_1$ kappa monoclonal antibody 2D2-B2 magnified 1600×.
Figure 29:
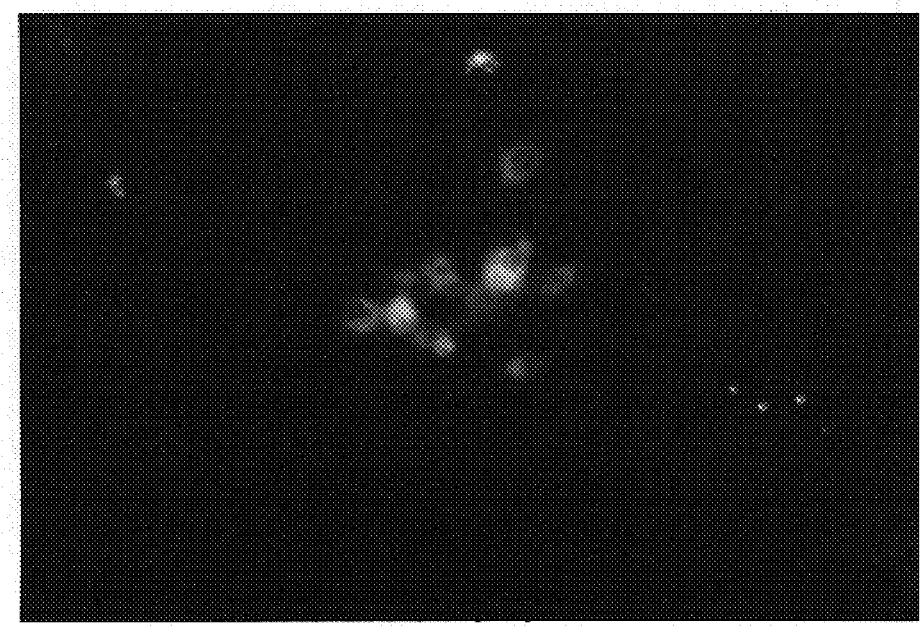
FIG. 29 is a photograph of buffy coat cells obtained from a human septic patient (No. 2) showing indirect immunofluorescent staining of hiNOS with mouse $IgG_1$ monoclonal antibody 2D2-B2 magnified 800×.

The ability of the various monoclonal antibodies to bind to iNOS in cells that have been induced to produce iNOS was examined in three different cell types, A-172 a human glioblastoma cell line, RAW 264.7 a mouse macrophage cell line, and normal human monocytes. The cells were cultured for two (2) days in normal medium and then induced to produce iNOS by treatment for 40 hours with a cytokine/LPS mixture (CM). Following the treatment, the cells were processed in one of two ways, either for lysis or for immunostaining. The cells that were to be lysed were detached from the culture flask, washed five (5) times, and frozen in a small volume of PBS to lyse. These were used for western immunoblots and to test the sandwich ELISA described in Examples 5 and 6 hereinbefore. The cells for immunostaining were washed four (4) times, and fixed in either 70% or 100% acetone. They were reacted for 60 minutes with the primary mouse anti-hiNOS monoclonal antibody, and then with FITC-conjugated goat anti-mouse IgG or IgM. They were observed and photographed by epifluorescence microscopy. FIGS. 15–17 illustrate the indirect immunofluorescent staining pattern observed on induced A-172 cells with three (3) different mouse anti-hiNOS monoclonal antibodies, 1E8-B8, 2A12-A4, and 2H11-D11 of Table IV, respectively. FIGS. 18 and 19 illustrate the indirect immunofluorescent staining observed on the fixed RAW 264.7 cells with anti-hiNOS monoclonal antibodies, 1E8-B8 and 2A12-A4 of Table IV, respectively. This shows that these two monoclones will also recognize and bind to mouse iNOS. This is similar to the results found by western immunoblotting. That is to say, these two (2) monoclonals can cross react with mouse iNOS. FIGS. 20 and 21 show the indirect immunostaining achieved using two (2) mouse anti-hiNOS monoclonal antibodies, 1E8-B8 and 2A12-A4 of Table IV, respectively, on induced normal human monocytes. The monocytes were isolated from normal human blood by density gradient centrifugation using Optiprep obtained from Accurate Chemical and Scientific Corp, Westbury, N.Y., following the manufacturer's direction as delineated in Application Sheet 2.3. These results show that these mouse anti-hiNOS monoclonal antibodies can recognize and bind to hiNOS which has been induced in normal human cells and tissues.

EXAMPLE 8

Test of Monoclonal Antibodies Ability to Inhibit the Enzymatic Activity of hiNOS The enzymatic activity of hiNOS was determined by measuring the amount of nitrite produced in the presence of the substrates and co-factors. We tested 13 different anti-hiNOS monoclonal antibodies for their ability to inhibit the activity of hiNOS. None of the monoclonal antibodies tested was found to inhibit the activity of the enzyme as determined by the Greise calorimetric assay described in an article entitled "Macrophage Deactivity Factor and Transforming Growth Factors—beta1, beta2, and beta3 Inhibit Induction of Macrophage Nitrogen Oxide Synthesis by IFN-gamma1" by Ding et al., Journal of Immunology, Vol. 145 (1990), and in an article entitled "Cloned Human Brain Nitric Oxide Synthase is Highly Expressed in Skeletal Muscle" by Nakane et al., FEBS Letters, Vol. 316 (1993).

EXAMPLE 9

Preparation of Reagents for Assays

The procedure of Example 2 was followed by the de novo preparation of ascites fluid from the cryopreserved cells of Example 1. This procedure was followed approximately 12 months following the initial preparation of Example 2.

The hereinafter results of Table VI were found to enhance the data of Example 2.

TABLE VI

| Clone | Isotype | ELISA | Specificity in Western Imoblots | Specific in IFA |
| --- | --- | --- | --- | --- |
| E8-B8 | Mouse Ig G1 Kappa | + | + (iNOS, eNOS) | + (iNOS, eNOS) |
| 2D2-B2 | Mouse Ig G1 Kappa | + | + (Only iNOS) | + (Only iNOS) |
| 5B3-E6 | Mouse Ig G1 Kappa | + | + (Only iNOS) | + (Only iNOS) |
| 21C10-1D10 | Mouse Ig G2 Kappa | + | + (Weak) (Only iNOS) | + (Only iNOS) |

The competitive binding ELISA in Table VI is based upon the competition for antibody binding between a synthetic peptide which is coated onto microtighter ELISA plates and iNOS in standards or unknowns which are in solution. It may be apparent a number of monoclonal antibodies of the present invention were found to bind to specific linear synthetic peptide analogues of protein. Most of the monoclonal antibodies were not sensitive enough two measure iNOS in physiological samples. However, one monoclonal antibody, 21C10-1D10 was found to be usable for measuring iNOS in physiological samples. By "tweaking" the ELISA with a longer synthetic peptide to coat the plates, and through ABC amplification, a fifty to sixty fold increase in sensitivity was achieved. The assay can be placed in any of a number of formats acceptable by clinical lab technicians. The competitive binding ELISA as depicted in Table VI has a minimum sensitivity of 20 fmole and takes three hours to complete. It is theorized that the addition of pre-incubation will further increase the sensitivity by a factor of two to three and provide an ELISA with a minimum sensitivity in the 6–10 fmole range.

EXAMPLE 10

Immunofluorescent Assay

An indirect immunofluorescent staining of cells was conducted according to the following procedures and in reference to Heimer and Taylor, J. Clin. Path., 27 (1974) page 254 and Johnson, et. al., J. Immunol., Meth. 55 (1982) P. 231. Cells were washed for one minute each with three changes of phosphate buffer saline (PBS) followed by a quick rinse in water. The water was drained well. Cells grown on glass were fixed in 100 percent acetone. Cells grown on plastic were fixed in 80 percent acetone and 20 percent water. Fixing took place for 10 to 15 minutes at room temperature, samples are air dried and stored at 20 degrees centigrade. Monoclonal antibodies were applied as cultured supernatants which were diluted 1:10/1:20/1:40 with PBS. Also, monoclonal antibodies were applied as ascites fluid and were diluted 1:500/1:2,500/1:12,500. The supernatants or ascites fluid were added directly to fixed cells at room temperature and incubated for one hour at 37 degrees centigrade, or two hours at room temperature. Each sample was then washed four times in PBS for one minute each and drained. FITC conjugated goat anti-mouse secondary antibodies were then added with Hyclone at 1:120 dilution in PBS. The samples were incubated 30 minutes at 37 degrees centigrade or 45 minutes at room temperature. Again, they were washed three times in PBS for one minute each and then rinsed in water to remove salts. After draining, a cover slip was mounted using glycerine based mounting medium which contains DABCO to reduce fading. The immunofluorescent staining was observed using an epi-fluorescent microscope equipped with excitation and emission wave length set for FITC.

The immunofluorescent assay utilized the 5B3-E6 and 2D2-B2 monoclonal antibodies. Staining was specifically blocked with the F6 peptide (PS-5166). iNOS was induced in many cell types and was detected by monoclonal antibodies 5B3-E6 and 2D2-B2. The induction process resulted in cells that immunofluoresce intensely. It is also discovered that fixed tissue sections were specifically immuno stained (using DAB rather than fluorescence) with the monoclonal antibodies 2D2-B2 and 5B3-E6 after iNOS induction in rats. This immuno staining could only be blocked with the appropriate peptide (F6=PS-5166). As currently formatted, this assay takes 90 minutes using an indirect immunofluorescent procedure. Using a direct procedure would probably reduce the time to 30 minutes or less.

FIGS. 22–29 represent the indirect immunofluorescent staining of samples using the reagents of Example 9.

The assay was validated using A-172 cell lysates (a human glioblastoma cell line) which do not produce hiNOS, enzyme, except under specific culture conditions. By immunofluorescent staining, Western Blotting, polyclonal antibody based RIA, and monoclonal antibody and peptide based competitive binding ELISA, show that no hiNOS was present in these controls. Also it was determined that hiNOS was induced by a mixture of cytokines and LPS.

EXAMPLE 11

Competitive Binding ELISA

Competitive binding ELISA assays were performed for samples in which plates were sensitized overnight. Washing was achieved four times and the plates blocked for three hours in PBS with two percent normal horse serum (NHS) to produce a block solution. Two times the concentration of the sample was added to each plate with 15 microliters of block solution. Two times the concentration of the 21C10-1D10 ascites in 15 microliter volumes of PBS were added in 2% NHS with 0.1% Tween 20. Samples were incubated at room temperature for 30 minutes. The preincubation period for ABC complex at a concentration of 1:120 in PBS with 0.1% Tween 20 took place for one hour at room temperature. After 30 minutes, the plates were washed four times and again two times with PBS. 100 microliters of Biot-HMIgG was added at 1:480 dilution in PBS and 2% NHS and 0.1% crystalline BSA for 30 minutes at room temperature. The plates were again washed four times. The ABC complex was diluted with and equal volume of PBS and 0.1 percent Tween 20.2% NHS and 0.1 percent crystalline BSA were added to the ABC mixture. 100 microliters per well of the pre-incubated ABC solution were added at room temperature and allowed to rest for 30 minutes. The samples were washed eight times. A color reaction was executed in 10× phosphate citrate buffer at pH 5.0 with 0.5 mg/ml of OPD and 0.08% hydrogen peroxide for 55 minutes at 37° C.

Figure 30:
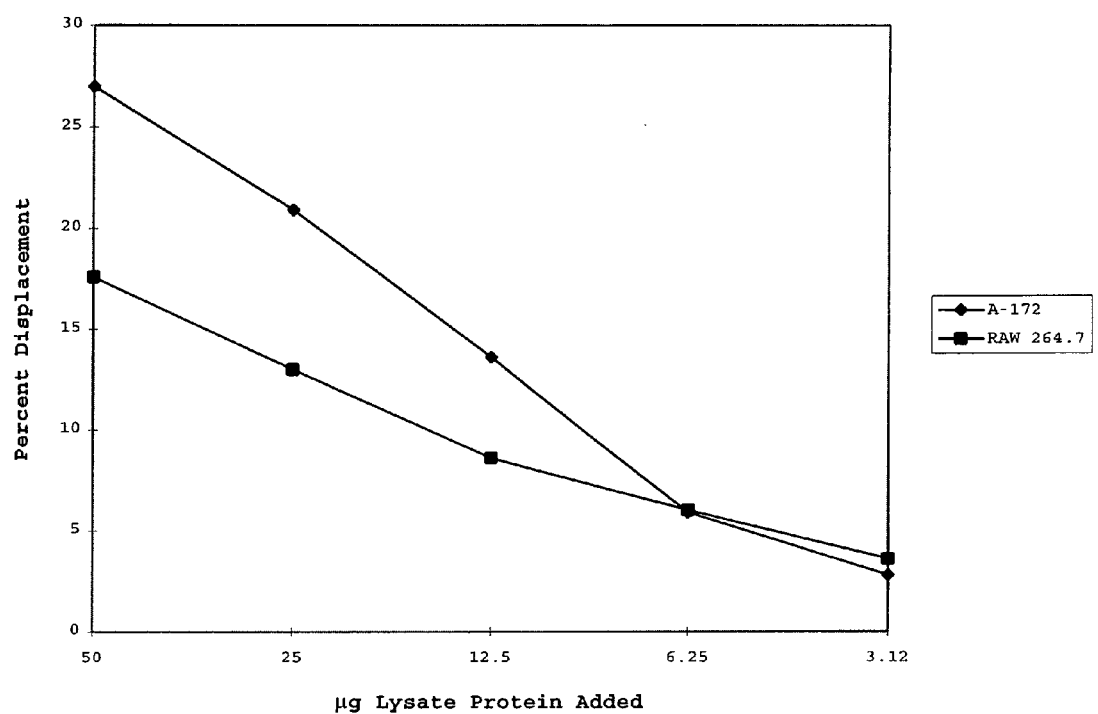
FIG. 30 is a graph representing a competitive binding ELISA that measures the quantity of iNOS using mouse $IgG_1$ monoclonal antibody 21C10-1D10 in cell lysates obtained from A-172 and RAW 264.7 cells 40 hours after induction with CM/LPS.
Figure 31:
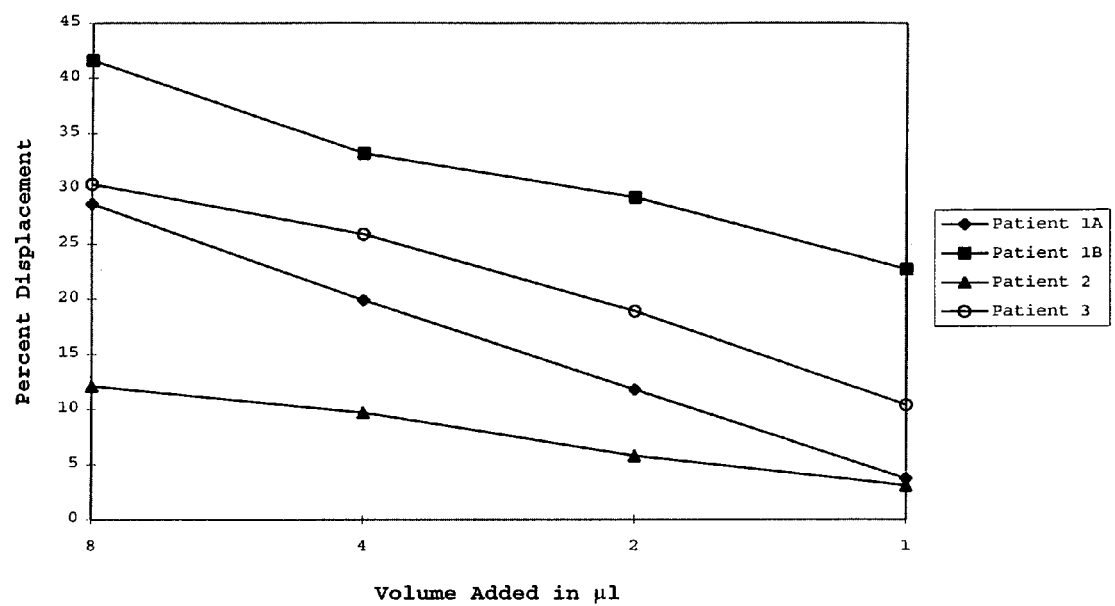
FIG. 31 is a graph representing a competitive binding ELISA that measures the quantity of hiNOS using mouse $IgG_1$ monoclonal antibody 21C10-1D10 in cells lysates obtained from the buffy coat cells of whole blood from three different human septic shock patients.

A number of the monoclonal antibodies of the present invention bound to specific linear synthetic peptide analogues of the protein. After examination of a number of monoclonal antibody and synthetic peptide pairs, one monoclonal antibody, 21C10-1D10 was found to be usable for measuring human iNOS. The ELISA was "tweaked" with a longer synthetic peptide to coat the plates and effect ABC amplification. A fifty to sixty fold increase was achieved in sensitivity. The ELISA was determined to take three hours to complete. It is believed that the addition of a pre-incubation step will further increase the sensitivity by a factor of two to three and will result in an ELISA with a minimum sensitivity in the 6–10 fmole range. FIGS. 30 and 31 represent the ELISA assay of this Example for quantifying iNOS and hiNOS. FIG. 32 shows the increased sensitivity of the assay of this Example using the A3+A4 peptide instead of the A4 peptide.

The assay was validated using A-172 cell lysates (glioblastoma cell line) which do not produce hiNOS, enzyme, except under specific culture conditions. By immunofluorescent staining, Western Blotting, polyclonal antibody based RIA, and monoclonal antibody and peptide based competitive binding ELISA, show that no hiNOS was present in these controls. Also it was determined that hiNOS was induced by a mixture of cytokines and LPS.

EXAMPLE 12

Epitope Mapping of 21C10-1D10 at the A4 Locus

Further epitope mapping of monoclonal antibody 21C10-1D10 was achieved at the amino terminal of the A4 locus of hiNOS Table VII represents these results.

TABLE VII

| Peptide | AA Segment | Sequence | Result |
|---|---|---|---|
| PS-5104 | hiNOS(37–54) | SPVTQDDLQYHNLSKQQN-amide SEQ ID NO 86 | ++++ |
| PS-5211 | hiNOS(41–45) | QDDLQ-amide SEQ ID NO 87 | -- |
| PS-5212 | hiNOS(40–45) | TQDDLQ-amide SEQ ID NO 88 | -- |
| PS-5213 | hiNOS(39–45) | VTQDDLQ-amide SEQ ID NO 89 | ++ |
| PS-5214 | hiNOS(38–45) | PVTQDDLQ-amide SEQ ID NO 90 | +++ |
| PS-5215 | hiNOS(37–45) | SPVTQDDLQ-amide SEQ ID NO 91 | +++ |
| PS-5232 | hiNOS(40–44) | TQDDL-amide SEQ ID NO 92 | -- |
| PS-5233 | hiNOS(39–44) | VTQDDL-amide SEQ ID NO 93 | + |
| PS-5234 | hiNOS(38–44) | PVTQDDL-amide SEQ ID NO 94 | + |
| PS-5235 | hiNOS(37–44) | SPVTQDDL-amide SEQ ID NO 95 | + |
| PS-5236 | hiNOS(36–44) | SSPVTQDDL-amide SEQ ID NO 96 | + |
| PS-5253 | hiNOS(39–43) | VTQDD-amide SEQ ID NO 97 | -- |
| PS-5254 | hiNOS(38–43) | PVTQDD-amide SEQ ID NO 98 | -- |
| PS-5255 | hiNOS(37–43) | SPVTQDD-amide SEQ ID NO 99 | -- |
| PS-5256 | hiNOS(36–43) | SSPVTQDD-amide SEQ ID NO 100 | -- |
| PS-5257 | hiNOS(35–43) | TSSPVTQDD-amide SEQ ID NO 101 | -- |

21C10-1D10 EPITOPE = VTQDDLQ

Figure 33:
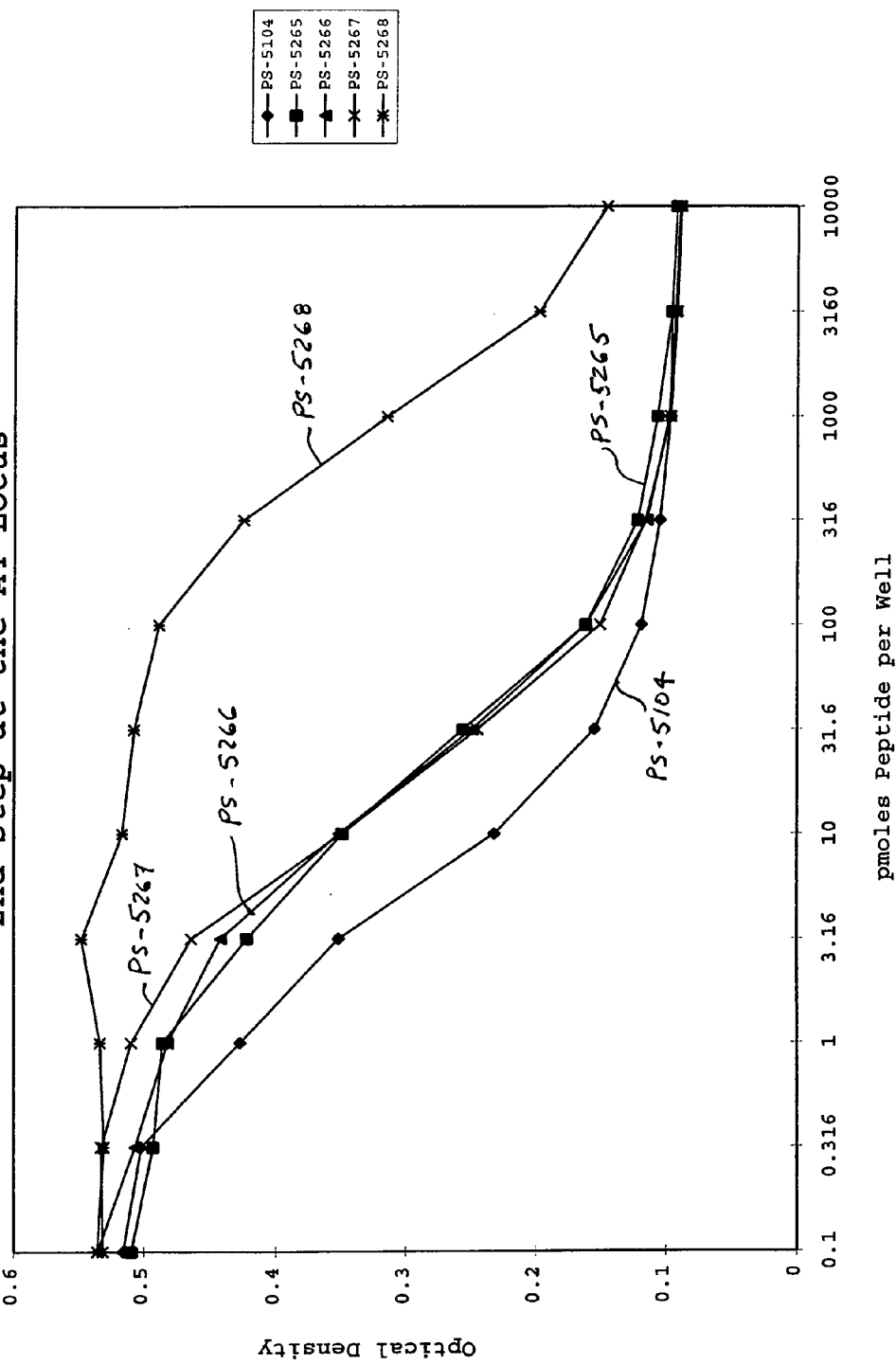
FIG. 33 is a graph representing a competitive binding ELISA using mouse $IgG_1$ monoclonal antibody 21C10-1D10, the A4 peptide (PS-5104), and the carboxyl terminal truncation peptides (PS-5265 to PS-5268) of Table V which locates the antibodies epitope to the amino terminal region of the A4 locus.

FIG. 33 represents the "2nd step" competitive binding ELISA using mouse IgG$_1$ monoclonal antibody 21C10-1D10, the A4 peptide (PS-5104), and the carboxyl terminal truncation peptides (PS-5265 to PS-5268) of Table V of Example 4. Table VIII represents epitope mapping of peptides PS-5261 to PS-5269 which highlighted the PS-5265 to PS-5268 peptides mapped in FIG. 33.

TABLE VIII

| Peptide | AA Segment | Sequence | Result |
|---|---|---|---|
| PS-5104 | hiNOS(37–54) | SPVTQDDLQYHNLSKQQN-amide SEQ ID NO 102 | ++++ |
| PS-5261 | hiNOS(40–54) | TQDDLQYHNLSKQQN-amide SEQ ID NO 103 | -- |
| PS-5262 | hiNOS(43–54) | DLQYHNLSKQQN-amide SEQ ID NO 104 | -- |
| PS-5263 | hiNOS(46–54) | YHNLSKQQN-amide SEQ ID NO 105 | -- |
| PS-5264 | hiNOS(49–54) | LSKQQN-amide SEQ ID NO 106 | -- |
| PS-5265 | hiNOS(37–51) | SPVTQDDLQYHNLSK-amide SEQ ID NO 107 | ++++ |
| PS-5266 | hiNOS(37–48) | SPVTQDDLQYHN-amide SEQ ID NO 108 | ++++ |
| PS-5267 | hiNOS(37–45) | SPVTQDDLQ-amide SEQ ID NO 109 | ++ |
| PS-5268 | hiNOS(37–42) | SPVTQD-amide SEQ ID NO 110 | -- |
| PS-5269 | hiNOS(35–44) | TSSPVTQDDL-amide SEQ ID NO 111 | + |

Figure 34:
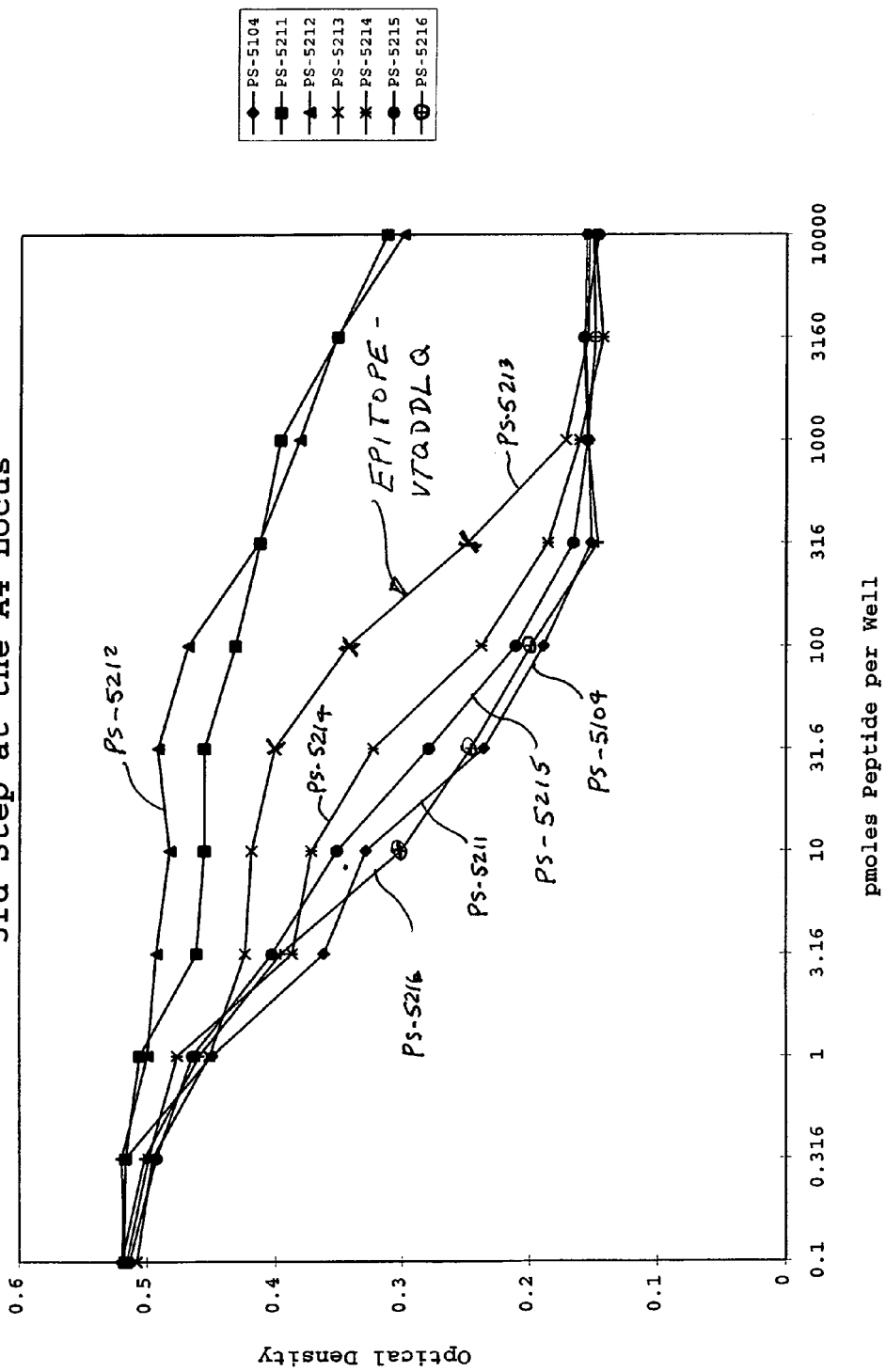
FIG. 34 is a graph depicting the competitive binding ELISA using mouse $IgG_1$ monoclonal antibody 21C10-1D10, the standard A4 peptide (PS-5104), and amino terminal elongation series (PS-5211 to PS-5216) of Table VII which locates the antibodies epitope to PS-5213, VTQD-DLQ (SEQ ID NO: 89).
Figure 35:
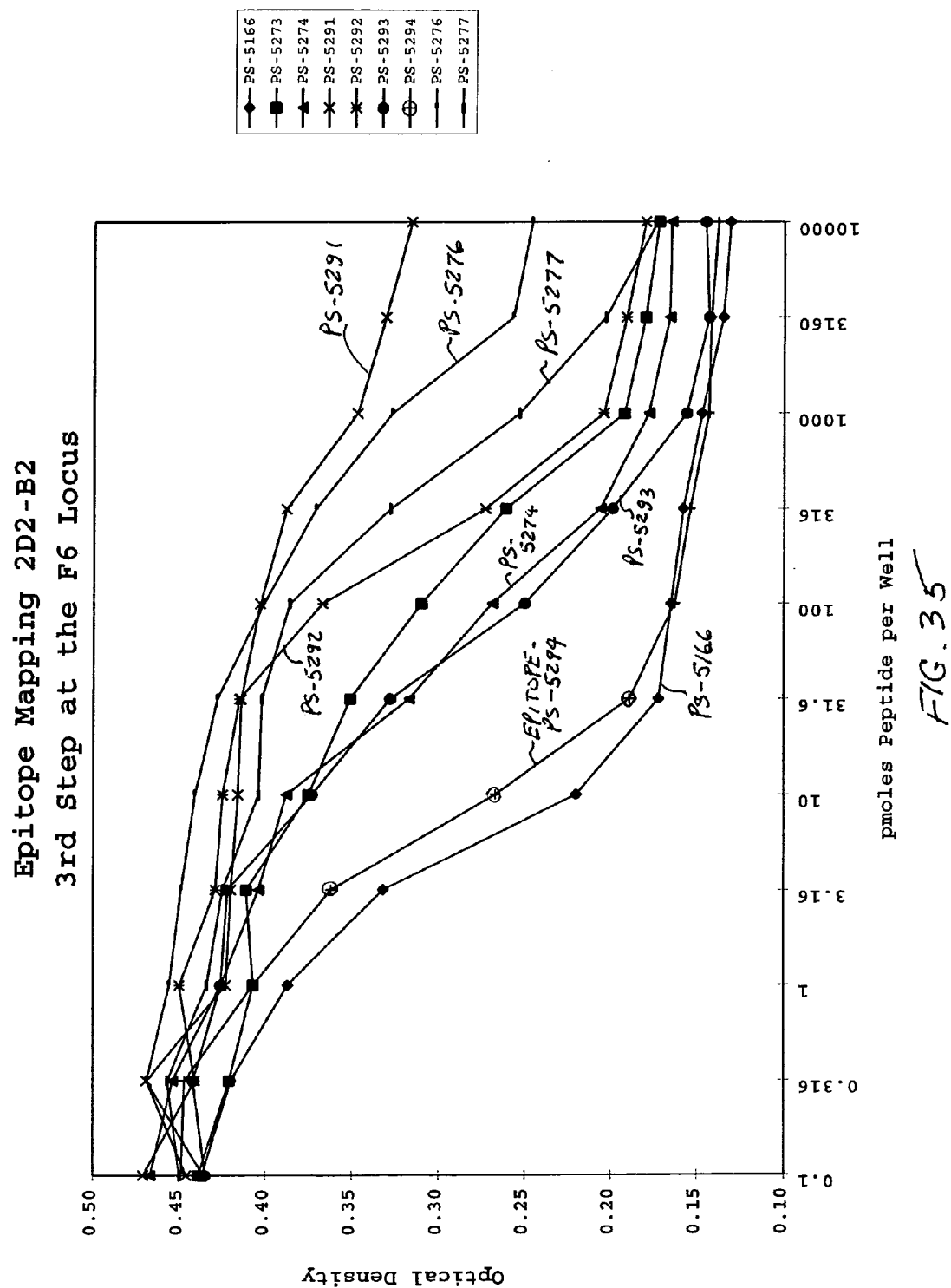
FIG. 35 is a graph depicting the competitive binding ELISA using mouse monoclonal antibody 2D2-B2, the standard F6 peptide (PS-5166), and peptides from the three mid-region elongation series of Table X which locates the antibody's epitope to PS-5294, VQGILERV (SEQ ID NO: 121).

Using the standard A-4 peptide (PS-5104) and amino acid terminal elongation series (PS-5211 to PS-5257) of the Table VII, in combination with mouse IgG$_1$ the antibodies epitope was determined to be PS-5213 VTQDDLQ. This "3rd step" epitope mapping is represented in the graph of FIG. 34.

EXAMPLE 13

Epitope Mapping of 2D2-B2, and 5B3-E6 of F6 Locus

Further epitope mapping of monoclonal antibodies 2D2-B2 and 5B3-E6 were undertaken at the mid region of the F6 locus (3rd step). Table IX represents these results and lists the peptides used, displays the results obtained in the competitive binding ELISA using mouse monoclonal antibodies 2D2-B2 and 5B3-E6 with the series of peptides that map the mid-region of the F6 locus. Table IX also identifies both of these antibodies' epitope as the sequence VQGILERV (hiNOS 784–791).

TABLE IX

| Peptide | AA Segment | Sequence | Result 2D2-B2 | Result 5B3-E6 |
|---|---|---|---|---|
| PS-5166 | hiNOS(781–798) | PALVQGILERVVDGPTPH-amide SEQ ID NO 112 | +++++ | +++++ |
| PS-5271 | hiNOS(788–792) | LERVV-amide SEQ ID NO 113 | -- | -- |
| PS-5272 | hiNOS(787–792) | ILERVV-amide SEQ ID NO 114 | + | + |
| PS-5273 | hiNOS(786–792) | GILERVV-amide SEQ ID NO 115 | +++ | +++ |
| PS-5274 | hiNOS(785–792) | QGILERVV-amide SEQ ID NO 116 | +++ | +++ |
| PS-5275 | hiNOS(784–792) | VQGILERVV-amide SEQ ID NO 117 | +++++ | +++++ |
| PS-5291 | hiNOS(787–791) | ILERV-amide SEQ ID NO 118 | + | + |
| PS-5292 | hiNOS(786–791) | GILERV-amide SEQ ID NO 119 | ++ | ++ |
| PS-5293 | hiNOS(785–791) | QGILERV-amide SEQ ID NO 120 | +++ | +++ |

TABLE IX-continued

| Peptide | AA Segment | Sequence | Result 2D2-B2 | Result 5B3-E6 |
|---|---|---|---|---|
| P5-5294 | hiNOS(784–791) | VQGILERV-amide SEQ ID NO 121 | +++++ | +++++ |
| PS-5295 | hiNOS(783–791) | LVQGILERV-amide SEQ ID NO 122 | +++++ | +++++ |
| PS-5276 | hiNOS(786–790) | GILER-amide SEQ ID NO 123 | + | + |
| PS-5277 | hiNOS(785–790) | QGILER-amide SEQ ID NO 124 | ++ | ++ |
| PS-5278 | hiNOS(784–790) | VQGILER-amide SEQ ID NO 125 | ++ | ++ |
| PS-5279 | hiNOS(783–790) | LVQGILER-amide SEQ ID NO 126 | ++ | ++ |

2D2-B2 EPITOPE = VQGILERV
5B3-E6 EPITOPE = VQGILERV

What is claimed is:

1. An immunoassay method for analysis of a sample, comprising the steps of:
   a. contacting the sample with a monoclonal antibody specifically recognizing human iNOS enzyme without cross-reacting with human nNOS or human eNOS; and
   b. detecting the presence of human iNOS protein in said sample, said monoclonal antibody recognizing human iNOS protein.

2. The method of claim 1 in which said immunoassay is selected from the group comprising: direct, indirect, capture, competitive binding, and displacement.

3. The method of claim 1 in which said step of detecting the presence of human iNOS protein comprises a qualitative analysis.

4. The method of claim 1 in which said step of detecting the presence of human iNOS comprises a quantitative analysis.

5. The method of claim 1 in which said binding assay comprises a clinical diagnostic assay.

6. The method of claim 1 which is of the type selected from the group consisting of: IFA, linear flow, radial flow, Western Blot, ELISA, dip stick, EIA, fluorescent polarization, enzyme capture, and RIA.

* * * * *

```
                            SEQUENCE LISTING (1) GENERAL INFORMATION:

(iii) NUMBER OF SEQUENCES: 126

(2) INFORMATION FOR SEQ ID NO: 1:

(i) SEQUENCE CHARACTERISTICS:
          (A) LENGTH: 18
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (25-42)
          (B) LOCATION:
          (C) IDENTIFICATION METHOD: AMINO ACID ANALYSIS
          (D) OTHER INFORMATION:

(xi) SEQUENCE DESCRIPTION:  SEQ ID NO: 1:

Asn  Asn  Asn  Val  Glu  Lys  Ala  Pro  Cys  Ala  Thr  Ser  Ser
                    5                        10

Pro  Val  Thr  Gln  Asp
     15

(2) INFORMATION FOR SEQ ID NO: 2:

(i) SEQUENCE CHARACTERISTICS:
          (A) LENGTH: 18
          (B) TYPE: AMINO ACID
          (D) TOPOLOGY: LINEAR (ii) MOLECULE TYPE: PEPTIDE (ix) FEATURE:
          (A) NAME/KEY: MOUSE iNOS (25-42)
          (B) LOCATION:
          (C) IDENTIFICATION METHOD: AMINO ACID ANALYSIS
          (D) OTHER INFORMATION:

(xi) SEQUENCE DESCRIPTION:  SEQ ID NO: 2:

Asn  Asn  Asn  Val  Lys  Lys  Thr  Pro  Cys  Ala  Val  Leu  Ser
                    5                        10

Pro  Thr  Ile  Gln  Asp
     15
```

-continued (2) INFORMATION FOR SEQ ID NO: 3:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (25-42)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 3:

Asn Asn Asn Val Glu Lys Thr Pro Gly Ala Ile Pro Ser
            5                  10

Pro Thr Thr Gln Asp
    15

(2) INFORMATION FOR SEQ ID NO: 4:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-54)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 4:

Ser Pro Val Thr Gln Asp Asp Leu Gln Tyr His Asn Leu
            5                  10

Ser Lys Gln Gln Asn
    15

(2) INFORMATION FOR SEQ ID NO: 5:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-798)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 5:

Pro Ala Leu Val Gln Gly Ile Leu Glu Arg Val Val Asp
            5                  10

Gly Pro Thr Pro His
    15

(2) INFORMATION FOR SEQ ID NO: 6:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (776-792)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 6:

Xaa Ala Leu Val Gln Gly Ile Leu Glu Arg Val Val Asp
                  5                      10

Cys Pro Thr Pro His
    15

(2) INFORMATION FOR SEQ ID NO: 7:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (780-794)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 7:

Xaa Xaa Leu Val Gln Gly Ile Leu Glu Arg Val Val Asp
                  5                      10

Cys Ser Ser Pro Xaa
    15

(2) INFORMATION FOR SEQ ID NO: 8:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-1002)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 8:

Gly Ile Val Pro Phe Arg Ser Phe Trp Gln Gln Arg Leu
                  5                      10

His Asp Ser Gln His
    15

(2) INFORMATION FOR SEQ ID NO: 9:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (978-995)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 9:

Gly Ile Ala Pro Phe Arg Ser Phe Trp Gln Gln Arg Leu
                  5                   10

His Asp Ser Gln His
     15

(2) INFORMATION FOR SEQ ID NO: 10:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (982-998)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 10:

Gly Ile Ala Pro Phe Arg Ser Phe Trp Gln Gln Arg Leu
                  5                   10

His Asp Ser Gln His
     15

(2) INFORMATION FOR SEQ ID NO: 11:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN nNOS (1256-1273)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 11:

Gly Ile Ala Pro Phe Arg Ser Phe Trp Gln Gln Arg Gln
                  5                   10

Phe Asp Ile Gln His
     15

(2) INFORMATION FOR SEQ ID NO: 12:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (1017-1031)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 12:

Gly Ile Ala Pro Phe Arg Gly Phe Trp Gln Glu Arg Leu
                  5                   10

His Asp Xaa Xaa Xaa

15

(2) INFORMATION FOR SEQ ID NO: 13:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: BOVINE eNOS (1019-1033)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 13:

Gly Ile Ala Pro Phe Arg Gly Phe Trp Gln Glu Arg Leu
                5                        10

His Asp Xaa Xaa Xaa
   15

(2) INFORMATION FOR SEQ ID NO: 14:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1026)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 14:

Arg Met Thr Leu Val Phe Gly Cys Arg Arg Pro Asp Glu
                5                        10

Asp His Ile Tyr Gln
   15

(2) INFORMATION FOR SEQ ID NO: 15:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (1006-1023)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 15:

Arg Met Thr Leu Val Phe Gly Cys Arg His Pro Glu Glu
                5                        10

Asp His Leu Tyr Gln
   15

(2) INFORMATION FOR SEQ ID NO: 16:

(i) SEQUENCE CHARACTERISTICS:
        (A) LENGTH: 18

```
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (1002-1019)
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 16:

Arg Met Ser Leu Val Phe Gly Cys Arg His Pro Glu Glu
                  5                   10

Asp His Leu Tyr Gln
   15

(2) INFORMATION FOR SEQ ID NO: 17:

(i) SEQUENCE CHARACTERISTICS:
        (A) LENGTH: 16
        (B) TYPE: AMINO ACID
        (D) TOPOLOGY: LINEAR (ii) MOLECULE TYPE: PEPTIDE (ix) FEATURE:
        (A) NAME/KEY: hnNOS [2-16, Cys17]
        (B) LOCATION: HUMAN nNOS: AMINO TERMINAL
        (C) IDENTIFICATION METHOD: AMINO ACID ANALYSIS
        (D) OTHER INFORMATION:

(xi) SEQUENCE DESCRIPTION: SEQ ID NO: 17:

Glu Asp His Met Phe Gly Val Gln Gln Ile Gln Pro Asn
                  5                   10

Val Ile Cys
   15

(2) INFORMATION FOR SEQ ID NO: 18:

(i) SEQUENCE CHARACTERISTICS:
        (A) LENGTH: 24
        (B) TYPE: AMINO ACID
        (D) TOPOLOGY: LINEAR (ii) MOLECULE TYPE: PEPTIDE (ix) FEATURE:
        (A) NAME/KEY: hnNOS [Cys1410-1411-1433]
        (B) LOCATION: HUMAN nNOS: CARBOXYL TERMINAL
        (C) IDENTIFICATION METHOD: AMINO ACID ANALYSIS
        (D) OTHER INFORMATION:

(xi) SEQUENCE DESCRIPTION: SEQ ID NO: 18:

Cys Arg Leu Arg Ser Glu Ser Ile Ala Phe Ile Glu Glu
                  5                   10

Ser Lys Lys Asp Thr Asp Glu Val Phe Ser Ser
   15                   20

(2) INFORMATION FOR SEQ ID NO: 19:

(i) SEQUENCE CHARACTERISTICS:
        (A) LENGTH: 20
        (B) TYPE: AMINO ACID
        (D) TOPOLOGY: LINEAR (ii) MOLECULE TYPE: PEPTIDE (ix) FEATURE:
        (A) NAME/KEY: hiNOS [2-21, Ser2]
```

```
        (B) LOCATION: HUMAN iNOS: AMINO TERMINAL
        (C) IDENTIFICATION METHOD: AMINO ACID ANALYSIS
        (D) OTHER INFORMATION:

(xi) SEQUENCE DESCRIPTION: SEQ ID NO: 19:

Ala Ser Pro Trp Lys Phe Leu Phe Lys Thr Lys Phe His
                  5                  10

Gln Tyr Ala Met Asn Gly Glu
 15                  20

(2) INFORMATION FOR SEQ ID NO: 20:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [Cys1136-1137-1153]
        (B) LOCATION: HUMAN iNOS: CARBOXYL TERMINAL
        (C) IDENTIFICATION METHOD: AMINO ACID ANALYSIS
        (D) OTHER INFORMATION:

(xi) SEQUENCE DESCRIPTION: SEQ ID NO: 20:

Cys Lys Lys Asp Arg Val Ala Val Gln Pro Ser Ser Leu
                  5                  10

Glu Met Ser Ala Leu
 15

(2) INFORMATION FOR SEQ ID NO: 21:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: heNOS [Cap-2-12, Cys13]
        (B) LOCATION: HUMAN eNOS: AMINO TERMINAL WITH CAPROIC ACID
            ATTACHED
        (C) IDENTIFICATION METHOD: AMINO ACID ANALYSIS
        (D) OTHER INFORMATION:

(xi) SEQUENCE DESCRIPTION: SEQ ID NO: 21:

Gly Asn Leu Lys Ser Val Ala Gln Glu Pro Gly Cys
                  5                  10

(2) INFORMATION FOR SEQ ID NO: 22:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: heNOS [2-12, Cys13]
        (B) LOCATION: HUMAN eNOS: AMINO TERMINAL WITHOUT CAPROIC
            ACID ATTACHED
        (C) IDENTIFICATION METHOD: AMINO ACID ANALYSIS
        (D) OTHER INFORMATION:

(xi) SEQUENCE DESCRIPTION: SEQ ID NO: 22:

Gly Asn Leu Lys Ser Val Ala Gln Glu Pro Gly Cys
                  5                  10
```

(2) INFORMATION FOR SEQ ID NO: 23:

(i) SEQUENCE CHARACTERISTICS:
        (A) LENGTH: 23
        (B) TYPE: AMINO ACID
        (D) TOPOLOGY: LINEAR (ii) MOLECULE TYPE: PEPTIDE (ix) FEATURE:
        (A) NAME/KEY: heNOS [Cys1181-1182-1203]
        (B) LOCATION: HUMAN eNOS: CARBOXYL TERMINAL
        (C) IDENTIFICATION METHOD: AMINO ACID ANALYSIS
        (D) OTHER INFORMATION:

(xi) SEQUENCE DESCRIPTION: SEQ ID NO: 23:

Cys Glu Arg Gln Leu Arg Glu Ala Val Pro Trp Ala Phe
                  5                   10
Asp Pro Pro Gly Ser Asp Thr Asn Ser Pro
    15                  20

(2) INFORMATION FOR SEQ ID NO: 24:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [985-1002]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 24:

Gly Ile Val Pro Phe Arg Ser Phe Trp Gln Gln Arg Leu
                  5                   10
His Asp Ser Gln His
    15

(2) INFORMATION FOR SEQ ID NO: 25:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [985-1002]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 25:

Gly Ile Val Pro Phe Arg Ser Phe Trp Gln Gln Arg Leu
                  5                   10
His Asp Ser Gln His
    15

(2) INFORMATION FOR SEQ ID NO: 26:

(i) SEQUENCE CHARACTERISTICS:
        (A) LENGTH: 18
        (B) TYPE: AMINO ACID

```
            (D) TOPOLOGY: LINEAR (ii) MOLECULE TYPE: PEPTIDE (ix) FEATURE:
            (A) NAME/KEY: hiNOS [37-54]
            (B) LOCATION:
            (C) IDENTIFICATION METHOD: AMINO ACID ANALYSIS
            (D) OTHER INFORMATION:

(xi) SEQUENCE DESCRIPTION:  SEQ ID NO: 26:

Ser  Pro  Val  Thr  Gln  Asp  Asp  Leu  Gln  Tyr  His  Asn  Leu
                         5                        10

Ser  Lys  Gln  Gln  Asn
              15

(2) INFORMATION FOR SEQ ID NO: 27:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: hiNOS [781-798]
            (B) LOCATION:
            (C) IDENTIFICATION METHOD: AMINO ACID ANALYSIS
            (D) OTHER INFORMATION:

(xi) SEQUENCE DESCRIPTION:  SEQ ID NO: 27:

Pro  Ala  Leu  Val  Gln  Gly  Ile  Leu  Glu  Arg  Val  Val  Asp
                         5                        10

Gly  Pro  Thr  Pro  His
              15

(2) INFORMATION FOR SEQ ID NO: 28:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: hiNOS [25-42]
            (B) LOCATION:
            (C) IDENTIFICATION METHOD: AMINO ACID ANALYSIS
            (D) OTHER INFORMATION:

(xi) SEQUENCE DESCRIPTION:  SEQ ID NO: 28:

Asn  Asn  Asn  Val  Glu  Lys  Ala  Pro  Ser  Ala  Thr  Ser  Ser
                         5                        10

Pro  Val  Thr  Gln  Asp
              15

(2) INFORMATION FOR SEQ ID NO: 29:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: hiNOS [37-54]
            (B) LOCATION:
```

-continued (C) IDENTIFICATION METHOD: AMINO ACID ANALYSIS
        (D) OTHER INFORMATION:

(xi) SEQUENCE DESCRIPTION: SEQ ID NO: 29:

Ser Pro Val Thr Gln Asp Asp Leu Gln Tyr His Asn Leu
                 5                  10

Ser Lys Gln Gln Asn
    15

(2) INFORMATION FOR SEQ ID NO: 30:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [781-798]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 30:

Pro Ala Leu Val Gln Gly Ile Leu Glu Arg Val Val Asp
                 5                  10

Gly Pro Thr Pro His
    15

(2) INFORMATION FOR SEQ ID NO: 31:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: hiNOS [1009-1026]
        (B) LOCATION:
        (C) IDENTIFICATION METHOD: AMINO ACID ANALYSIS
        (D) OTHER INFORMATION:

(xi) SEQUENCE DESCRIPTION: SEQ ID NO: 31:

Arg Met Thr Leu Val Phe Gly Ser Arg Arg Pro Asp Glu
                 5                  10

Asp His Ile Tyr Gln
    15

(2) INFORMATION FOR SEQ ID NO: 32:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (A3) LOCUS HUMAN iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 32:

Asn Asn Asn Val Glu Lys Ala Pro Ser Ala Thr Ser Ser
                 5                  10

```
Pro Val Thr Gln Asp
    15

(2) INFORMATION FOR SEQ ID NO: 33:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: MOUSE iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 33:

Asn Asn Asn Val Lys Lys Thr Pro Ser Ala Val Leu Ser
                5                   10

Pro Thr Ile Gln Asp
    15

(2) INFORMATION FOR SEQ ID NO: 34:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: RAT iNOS (25-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 34:

Asn Asn Asn Val Glu Lys Thr Pro Gly Ala Ile Pro Ser
                5                   10

Pro Thr Thr Gln Asp
    15

(2) INFORMATION FOR SEQ ID NO: 35:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (28-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 35:

Val Glu Lys Ala Pro Ser Ala Thr Ser Ser Pro Val Thr
                5                   10

Gln Asp
    15

(2) INFORMATION FOR SEQ ID NO: 36:
```

(i) SEQUENCE CHARACTERISTICS:
    (A) LENGTH: 12
    (B) TYPE: AMINO ACID
    (D) TOPOLOGY: LINEAR (ii) MOLECULE TYPE: PEPTIDE (ix) FEATURE:
    (A) NAME/KEY: HUMAN iNOS (31-42)
    (B) LOCATION: CARBOXY TERMINAL WITH AMIDE
    (C) IDENTIFICATION METHOD: AMINO ACID ANALYSIS
    (D) OTHER INFORMATION:

(xi) SEQUENCE DESCRIPTION: SEQ ID NO: 36:

Ala Pro Ser Ala Thr Ser Ser Pro Val Thr Gln Asp
                 5                   10

(2) INFORMATION FOR SEQ ID NO: 37:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (34-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 37:

Ala Thr Ser Ser Pro Val Thr Gln Asp
                 5

(2) INFORMATION FOR SEQ ID NO: 38:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-42)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 38:

Ser Pro Val Thr Gln Asp
                 5

(2) INFORMATION FOR SEQ ID NO: 39:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (25-39)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 39:

Asn Asn Asn Val Glu Lys Ala Pro Ser Ala Thr Ser Ser

```
                         5                  10
Pro Val
    15

(2) INFORMATION FOR SEQ ID NO: 40:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
         (A) NAME/KEY: HUMAN iNOS (25-36)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 40:

Asn Asn Asn Val Glu Lys Ala Pro Ser Ala Thr Ser
                 5                  10

(2) INFORMATION FOR SEQ ID NO: 41:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
         (A) NAME/KEY: HUMAN iNOS (25-33)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 41:

Asn Asn Asn Val Glu Lys Ala Pro Ser
                 5

(2) INFORMATION FOR SEQ ID NO: 42:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
         (A) NAME/KEY: HUMAN iNOS (25-30)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 42:

Asn Asn Asn Val Glu Lys
                 5

(2) INFORMATION FOR SEQ ID NO: 43:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
```

(A) NAME/KEY: (A4) LOCUS HUMAN iNOS (37-54)
    (B) LOCATION: CARBOXY TERMINAL WITH AMIDE
    (C) IDENTIFICATION METHOD: AMINO ACID ANALYSIS
    (D) OTHER INFORMATION:

(xi) SEQUENCE DESCRIPTION: SEQ ID NO: 43:

Ser Pro Val Thr Gln Asp Asp Leu Gln Tyr His Asn Leu
                    5                   10

Ser Lys Gln Gln Asn
    15

(2) INFORMATION FOR SEQ ID NO: 44:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (40-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 44:

Thr Gln Asp Asp Leu Gln Tyr His Asn Leu Ser Lys Gln
                5                   10

Gln Asn
    15

(2) INFORMATION FOR SEQ ID NO: 45:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (43-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 45:

Asp Leu Gln Tyr His Asn Leu Ser Lys Gln Gln Asn
                5                   10

(2) INFORMATION FOR SEQ ID NO: 46:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (46-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 46:

Tyr His Asn Leu Ser Lys Gln Gln Asn
                5

(2) INFORMATION FOR SEQ ID NO: 47:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (49-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 47:

Leu  Ser  Lys  Gln  Gln  Asn
                    5

(2) INFORMATION FOR SEQ ID NO: 48:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-51)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 48:

Ser  Pro  Val  Thr  Gln  Asp  Asp  Leu  Gln  Tyr  His  Asn  Leu
                    5                             10

Ser  Lys
     15

(2) INFORMATION FOR SEQ ID NO: 49:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-48)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 49:

Ser  Pro  Val  Thr  Gln  Asp  Asp  Leu  Gln  Tyr  His  Asn
                    5                             10

(2) INFORMATION FOR SEQ ID NO: 50:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-45)
        (B) LOCATION: CARBOXY TERMINAL WITH AMIDE

```
            (C) IDENTIFICATION METHOD: AMINO ACID ANALYSIS
            (D) OTHER INFORMATION:

(xi) SEQUENCE DESCRIPTION: SEQ ID NO: 50:

Ser  Pro  Val  Thr  Gln  Asp  Asp  Leu  Gln
                     5

(2) INFORMATION FOR SEQ ID NO: 51:

(i) SEQUENCE CHARACTERISTICS:
            (A) LENGTH: 6
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (37-42)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 51:

Ser  Pro  Val  Thr  Gln  Asp
                     5

(2) INFORMATION FOR SEQ ID NO: 52:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: (F6) LOCUS HUMAN iNOS (781-798)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 52:

Pro  Ala  Leu  Val  Gln  Gly  Ile  Leu  Glu  Arg  Val  Val  Asp
                     5                              10

Gly  Pro  Thr  Pro  His
     15

(2) INFORMATION FOR SEQ ID NO: 53:

(i) SEQUENCE CHARACTERISTICS:
            (A) LENGTH: 19
            (B) TYPE: AMINO ACID
            (D) TOPOLOGY: LINEAR (ii) MOLECULE TYPE: PEPTIDE (ix) FEATURE:
            (A) NAME/KEY: HUMAN eNOS (806-824)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 53:

Pro  Gly  Leu  Val  Glu  Ala  Leu  Leu  Ser  Arg  Val  Glu  Asp
                     5                              10

Pro  Pro  Ala  Pro  Thr  Glu
     15

(2) INFORMATION FOR SEQ ID NO: 54:
```

```
    (i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (784-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 54:

Val  Gln  Gly  Ile  Leu  Glu  Arg  Val  Val  Asp  Gly  Pro  Thr
                    5                        10

Pro  His
     15

(2) INFORMATION FOR SEQ ID NO: 55:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (787-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 55:

Ile  Leu  Glu  Arg  Val  Val  Asp  Gly  Pro  Thr  Pro  His
                    5                        10

(2) INFORMATION FOR SEQ ID NO: 56:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (790-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION:  SEQ ID NO: 56:

Arg  Val  Val  Asp  Gly  Pro  Thr  Pro  His
                    5

(2) INFORMATION FOR SEQ ID NO: 57:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (793-798)
        (B) LOCATION: CARBOXY TERMINAL WITH AMIDE
        (C) IDENTIFICATION METHOD: AMINO ACID ANALYSIS
        (D) OTHER INFORMATION:
```

(xi) SEQUENCE DESCRIPTION: SEQ ID NO: 57:

Asp Gly Pro Thr Pro His
                    5

(2) INFORMATION FOR SEQ ID NO: 58:

(i) SEQUENCE CHARACTERISTICS:
        (A) LENGTH: 14
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-794)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 58:

Pro Ala Leu Val Gln Gly Ile Leu Glu Arg Val Val Asp
                    5                       10
Gly (2) INFORMATION FOR SEQ ID NO: 59:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 59:

Pro Ala Leu Val Gln Gly Ile Leu Glu Arg Val Val
                    5                       10

(2) INFORMATION FOR SEQ ID NO: 60:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-789)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 60:

Pro Ala Leu Val Gln Gly Ile Leu Glu
                    5

(2) INFORMATION FOR SEQ ID NO: 61:

(i) SEQUENCE CHARACTERISTICS:
        (A) LENGTH: 6
        (B) TYPE: AMINO ACID
        (D) TOPOLOGY: LINEAR

```
       (ii) MOLECULE TYPE: PEPTIDE (ix) FEATURE:
            (A) NAME/KEY: HUMAN iNOS (781-786)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 61:

Pro  Ala  Leu  Val  Gln  Gly
                     5

(2) INFORMATION FOR SEQ ID NO: 62:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: (G11) LOCUS HUMAN iNOS (985-1002)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 62:

Gly  Ile  Val  Pro  Phe  Arg  Ser  Phe  Trp  Gln  Gln  Arg  Leu
                     5                              10

His  Asp  Ser  Gln  His
          15

(2) INFORMATION FOR SEQ ID NO: 63:

(i) SEQUENCE CHARACTERISTICS:
            (A) LENGTH: 18
            (B) TYPE: AMINO ACID
            (D) TOPOLOGY: LINEAR (ii) MOLECULE TYPE: PEPTIDE (ix) FEATURE:
            (A) NAME/KEY: HUMAN nNOS (1256-1273)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 63:

Gly  Ile  Ala  Pro  Phe  Arg  Ser  Phe  Trp  Gln  Gln  Arg  Gln
                     5                              10

Phe  Asp  Ile  Gln  His
          15

(2) INFORMATION FOR SEQ ID NO: 64:

(i) SEQUENCE CHARACTERISTICS:
            (A) LENGTH: 15
            (B) TYPE: AMINO ACID
            (D) TOPOLOGY: LINEAR (ii) MOLECULE TYPE: PEPTIDE (ix) FEATURE:
            (A) NAME/KEY: HUMAN eNOS (1017-1031)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 64:
```

```
Gly Ile Ala Pro Phe Arg Gly Phe Trp Gln Glu Arg Leu
                5                   10
His Asp
    15

(2) INFORMATION FOR SEQ ID NO: 65:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (988-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 65:

Pro Phe Arg Ser Phe Trp Gln Gln Arg Leu His Asp Ser
                5                   10
Gln His
    15

(2) INFORMATION FOR SEQ ID NO: 66:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (991-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 66:

Ser Phe Trp Gln Gln Arg Leu His Asp Ser Gln His
                5                   10

(2) INFORMATION FOR SEQ ID NO: 67:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (994-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 67:

Gln Gln Arg Leu His Asp Ser Gln His
                5

(2) INFORMATION FOR SEQ ID NO: 68:

(i) SEQUENCE CHARACTERISTICS:
        (A) LENGTH: 5
        (B) TYPE: AMINO ACID
        (D) TOPOLOGY: LINEAR
```

```
    (ii) MOLECULE TYPE: PEPTIDE (ix) FEATURE:
        (A) NAME/KEY: HUMAN iNOS (997-1002)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 68:

His Asp Ser Gln His
                5

(2) INFORMATION FOR SEQ ID NO: 69:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-998)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 69:

Gly Ile Val Pro Phe Arg Ser Phe Trp Gln Gln Arg Leu
                5                        10

His Asp
    15

(2) INFORMATION FOR SEQ ID NO: 70:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-996)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 70:

Gly Ile Val Pro Phe Arg Ser Phe Trp Gln Gln Arg
                5                        10

(2) INFORMATION FOR SEQ ID NO: 71:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-993)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 71:

Gly Ile Val Pro Phe Arg Ser Phe Trp
                5
```

(2) INFORMATION FOR SEQ ID NO: 72:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (985-990)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 72:

Gly Ile Val Pro Phe Arg
               5

(2) INFORMATION FOR SEQ ID NO: 73:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: (H1) LOCUS HUMAN iNOS (1009-1026)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 73:

Arg Met Thr Leu Val Phe Gly Ser Arg Arg Pro Asp Glu
                      5                        10

Asp His Ile Tyr Gln
            15

(2) INFORMATION FOR SEQ ID NO: 74:

(i) SEQUENCE CHARACTERISTICS:
        (A) LENGTH: 17
        (B) TYPE: AMINO ACID
        (D) TOPOLOGY: LINEAR (ii) MOLECULE TYPE: PEPTIDE (ix) FEATURE:
        (A) NAME/KEY: HUMAN eNOS (1041-1057)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 74:

Met Thr Leu Val Phe Gly Ser Arg Ser Ser Gln Leu Asp
                  5                        10

His Leu Tyr Arg
           15

(2) INFORMATION FOR SEQ ID NO: 75:

(i) SEQUENCE CHARACTERISTICS:
        (A) LENGTH: 17
        (B) TYPE: AMINO ACID
        (D) TOPOLOGY: LINEAR (ii) MOLECULE TYPE: PEPTIDE (ix) FEATURE:
            (A) NAME/KEY: HUMAN nNOS (1281-1297)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 75:

Met Val Leu Val Phe Gly Ser Arg Gln Ser Lys Ile Asp
                  5                  10

His Ile Tyr Arg
    15

(2) INFORMATION FOR SEQ ID NO: 76:

(i) SEQUENCE CHARACTERISTICS:
            (A) LENGTH: 15
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1012-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 76:

Leu Val Phe Gly Ser Arg Arg Pro Asp Glu Asp His Ile
                  5                  10

Tyr Gln
    15

(2) INFORMATION FOR SEQ ID NO: 77:

(i) SEQUENCE CHARACTERISTICS:
            (A) LENGTH: 12
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1015-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 77:

Gly Ser Arg Arg Pro Asp Glu Asp His Ile Tyr Gln
                  5                  10

(2) INFORMATION FOR SEQ ID NO: 78:

(i) SEQUENCE CHARACTERISTICS:
            (A) LENGTH: 9
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1018-1026)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 78:

Arg Pro Asp Glu Asp His Ile Tyr Gln

5

(2) INFORMATION FOR SEQ ID NO: 79:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1021-1026)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 79:

Glu Asp His Ile Tyr Gln
                5

(2) INFORMATION FOR SEQ ID NO: 80:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1023)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 80:

Arg Met Thr Leu Val Phe Gly Ser Arg Arg Pro Asp Glu
                5                   10
Asp His
   15

(2) INFORMATION FOR SEQ ID NO: 81:

(i) SEQUENCE CHARACTERISTICS:
        (A) LENGTH: 11
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (1009-1020)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 81:

Arg Met Thr Leu Val Phe Gly Ser Arg Arg Pro
                5                   10

(2) INFORMATION FOR SEQ ID NO: 82:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:

```
            (A) NAME/KEY: HUMAN iNOS (1009-1017)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 82:

Arg Met Thr Leu Val Phe Gly Ser Arg
                 5

(2) INFORMATION FOR SEQ ID NO: 83:

(i) SEQUENCE CHARACTERISTICS:
            (A) LENGTH: 6
            (B) TYPE: AMINO ACID
            (D) TOPOLOGY: LINEAR (ii) MOLECULE TYPE: PEPTIDE (ix) FEATURE:
            (A) NAME/KEY: HUMAN iNOS (1009-1014)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 83:

Arg Met Thr Leu Val Phe
                 5

(2) INFORMATION FOR SEQ ID NO: 84:

(i) SEQUENCE CHARACTERISTICS:
            (A) LENGTH: 12
            (B) TYPE: AMINO ACID
            (D) TOPOLOGY: LINEAR (ii) MOLECULE TYPE: PEPTIDE (ix) FEATURE:
            (A) NAME/KEY: TRUNCATED HUMAN iNOS (40-54)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 84:

Thr Gln Asp Asp Leu Gln Tyr His Asn Leu Ser Lys
                 5                   10

(2) INFORMATION FOR SEQ ID NO: 85:

(i) SEQUENCE CHARACTERISTICS:
            (A) LENGTH: 9
            (B) TYPE: AMINO ACID
            (D) TOPOLOGY: LINEAR (ii) MOLECULE TYPE: PEPTIDE (ix) FEATURE:
            (A) NAME/KEY: TRUNCATED HUMAN iNOS (784-798)
            (B) LOCATION: CARBOXY TERMINAL WITH AMIDE
            (C) IDENTIFICATION METHOD: AMINO ACID ANALYSIS
            (D) OTHER INFORMATION:

(xi) SEQUENCE DESCRIPTION: SEQ ID NO: 85:

Val Gln Gly Ile Leu Glu Arg Val Val
                 5

(2) INFORMATION FOR SEQ ID NO: 86:

(i) SEQUENCE CHARACTERISTICS:
            (A) LENGTH: 18
            (B) TYPE: AMINO ACID
```

(D) TOPOLOGY: LINEAR (ii) MOLECULE TYPE: PEPTIDE (ix) FEATURE:
        (A) NAME/KEY: HUMAN iNOS (37-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 86:

Ser Pro Val Thr Gln Asp Asp Leu Gln Tyr His Asn Leu
                  5                   10
Ser Lys Gln Gln Asn
 15

(2) INFORMATION FOR SEQ ID NO: 87:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (41-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 87:

Gln Asp Asp Leu Gln
               5

(2) INFORMATION FOR SEQ ID NO: 88:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (40-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 88:

Thr Gln Asp Asp Leu Gln
                   5

(2) INFORMATION FOR SEQ ID NO: 89:

(i) SEQUENCE CHARACTERISTICS:
        (A) LENGTH: 7
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (39-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 89:

Val Thr Gln Asp Asp Leu Gln

5

(2) INFORMATION FOR SEQ ID NO: 90:

(i) SEQUENCE CHARACTERISTICS:
        (A) LENGTH: 8
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (38-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 90:

Pro Val Thr Gln Asp Asp Leu Gln
                 5

(2) INFORMATION FOR SEQ ID NO: 91:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-45)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 91:

Ser Pro Val Thr Gln Asp Asp Leu Gln
                     5

(2) INFORMATION FOR SEQ ID NO: 92:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (40-44)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 92:

Thr Gln Asp Asp Leu
                 5

(2) INFORMATION FOR SEQ ID NO: 93:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (39-44)
        (B) LOCATION: CARBOXY TERMINAL WITH AMIDE
        (C) IDENTIFICATION METHOD: AMINO ACID ANALYSIS (D) OTHER INFORMATION:

(xi) SEQUENCE DESCRIPTION: SEQ ID NO: 93:

Val  Thr  Gln  Asp  Asp  Leu
                    5

(2) INFORMATION FOR SEQ ID NO: 94:

(i) SEQUENCE CHARACTERISTICS:
        (A) LENGTH: 7
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (38-44)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 94:

Pro  Val  Thr  Gln  Asp  Asp  Leu
                    5

(2) INFORMATION FOR SEQ ID NO: 95:

(i) SEQUENCE CHARACTERISTICS:
        (A) LENGTH: 8
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-44)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 95:

Ser  Pro  Val  Thr  Gln  Asp  Asp  Leu
                    5

(2) INFORMATION FOR SEQ ID NO: 96:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (36-44)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 96:

Ser  Ser  Pro  Val  Thr  Gln  Asp  Asp  Leu
                    5

(2) INFORMATION FOR SEQ ID NO: 97:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE

```
    (ix) FEATURE:
          (A) NAME/KEY: HUMAN iNOS (39-43)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 97:

Val  Thr  Gln  Asp  Asp
                     5

(2) INFORMATION FOR SEQ ID NO: 98:

(i) SEQUENCE CHARACTERISTICS:
          (A) LENGTH: 6
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (38-43)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 98:

Pro  Val  Thr  Gln  Asp  Asp
                          5

(2) INFORMATION FOR SEQ ID NO: 99:

(i) SEQUENCE CHARACTERISTICS:
          (A) LENGTH: 7
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (37-43)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 99:

Ser  Pro  Val  Thr  Gln  Asp  Asp
                               5

(2) INFORMATION FOR SEQ ID NO: 100:

(i) SEQUENCE CHARACTERISTICS:
          (A) LENGTH: 8
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (36-43)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 100:

Ser  Ser  Pro  Val  Thr  Gln  Asp  Asp
                               5

(2) INFORMATION FOR SEQ ID NO: 101:

(i) SEQUENCE CHARACTERISTICS:
```

(A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (35-43)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 101:

Thr Ser Ser Pro Val Thr Gln Asp Asp
                5

(2) INFORMATION FOR SEQ ID NO: 102:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (37-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 102:

Ser Pro Val Thr Gln Asp Asp Leu Gln Tyr His Asn Leu
                5                           10

Ser Lys Gln Gln Asn
 15

(2) INFORMATION FOR SEQ ID NO: 103:

(i) SEQUENCE CHARACTERISTICS:
        (A) LENGTH: 15
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (40-54)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 103:

Thr Gln Asp Asp Leu Gln Tyr His Asn Leu Ser Lys Gln
                5                           10

Gln Asn
 15

(2) INFORMATION FOR SEQ ID NO: 104:

(i) SEQUENCE CHARACTERISTICS:
        (A) LENGTH: 12
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (43-54)
        (B) LOCATION: CARBOXY TERMINAL WITH AMIDE
        (C) IDENTIFICATION METHOD: AMINO ACID ANALYSIS (D) OTHER INFORMATION:

(xi) SEQUENCE DESCRIPTION: SEQ ID NO: 104:

Asp Leu Gln Tyr His Asn Leu Ser Lys Gln Gln Asn
                  5                  10

(2) INFORMATION FOR SEQ ID NO: 105:

(i) SEQUENCE CHARACTERISTICS:
          (A) LENGTH: 9
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (46-54)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 105:

Tyr His Asn Leu Ser Lys Gln Gln Asn
                  5

(2) INFORMATION FOR SEQ ID NO: 106:

(i) SEQUENCE CHARACTERISTICS:
          (A) LENGTH: 6
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (49-54)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 106:

Leu Ser Lys Gln Gln Asn
                  5

(2) INFORMATION FOR SEQ ID NO: 107:

(i) SEQUENCE CHARACTERISTICS:
          (A) LENGTH: 15
          (B) TYPE: AMINO ACID
          (D) TOPOLOGY: LINEAR (ii) MOLECULE TYPE: PEPTIDE (ix) FEATURE:
          (A) NAME/KEY: HUMAN iNOS (37-51)
          (B) LOCATION: CARBOXY TERMINAL WITH AMIDE
          (C) IDENTIFICATION METHOD: AMINO ACID ANALYSIS
          (D) OTHER INFORMATION:

(xi) SEQUENCE DESCRIPTION: SEQ ID NO: 107:

Ser Pro Val Thr Gln Asp Asp Leu Gln Tyr His Asn Leu
                  5                  10

Ser Lys
    15

(2) INFORMATION FOR SEQ ID NO: 108:

(i) SEQUENCE CHARACTERISTICS:
          (A) LENGTH: 12
          (B) TYPE: AMINO ACID

```
        (D) TOPOLOGY: LINEAR (ii) MOLECULE TYPE: PEPTIDE (ix) FEATURE:
         (A) NAME/KEY: HUMAN iNOS (37-48)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 108:

Ser  Pro  Val  Thr  Gln  Asp  Asp  Leu  Gln  Tyr  His  Asn
                     5                        10

(2) INFORMATION FOR SEQ ID NO: 109:

(i) SEQUENCE CHARACTERISTICS:
         (A) LENGTH: 9
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (37-45)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 109:

Ser  Pro  Val  Thr  Gln  Asp  Asp  Leu  Gln
                     5

(2) INFORMATION FOR SEQ ID NO: 110:

(i) SEQUENCE CHARACTERISTICS:
         (A) LENGTH: 6
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (37-42)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 110:

Ser  Pro  Val  Thr  Gln  Asp
                     5

(2) INFORMATION FOR SEQ ID NO: 111:

(i) SEQUENCE CHARACTERISTICS:
         (A) LENGTH: 10
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (35-44)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 111:

Thr  Ser  Ser  Pro  Val  Thr  Gln  Asp  Asp  Leu
                     5                        10
```

(2) INFORMATION FOR SEQ ID NO: 112:

(i) SEQUENCE CHARACTERISTICS:
        (A) LENGTH: 18
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (781-798)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 112:

Pro Ala Leu Val Gln Gly Ile Leu Glu Arg Val Val Asp
               5                                10

Gly Pro Thr Pro His
    15

(2) INFORMATION FOR SEQ ID NO: 113:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (788-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 113:

Leu Glu Arg Val Val
              5

(2) INFORMATION FOR SEQ ID NO: 114:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (787-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 114:

Ile Leu Glu Arg Val Val
                   5

(2) INFORMATION FOR SEQ ID NO: 115:

(i) SEQUENCE CHARACTERISTICS:
        (A) LENGTH: 7
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (786-792)
        (B) LOCATION: CARBOXY TERMINAL WITH AMIDE
        (C) IDENTIFICATION METHOD: AMINO ACID ANALYSIS

```
            (D) OTHER INFORMATION:

(xi) SEQUENCE DESCRIPTION: SEQ ID NO: 115:

Gly Ile Leu Glu Arg Val Val
              5

(2) INFORMATION FOR SEQ ID NO: 116:

(i) SEQUENCE CHARACTERISTICS:
        (A) LENGTH: 8
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (785-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 116:

Gln Gly Ile Leu Glu Arg Val Val
              5

(2) INFORMATION FOR SEQ ID NO: 117:

(i) SEQUENCE CHARACTERISTICS:
        (A) LENGTH: 9
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (784-792)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 117:

Val Gln Gly Ile Leu Glu Arg Val Val
              5

(2) INFORMATION FOR SEQ ID NO: 118:

(i) SEQUENCE CHARACTERISTICS:
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (787-791)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 118:

Ile Leu Glu Arg Val
              5

(2) INFORMATION FOR SEQ ID NO: 119:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE
```

```
    (ix) FEATURE:
         (A) NAME/KEY: HUMAN iNOS (786-791)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 119:

Gly Ile Leu Glu Arg Val
                  5

(2) INFORMATION FOR SEQ ID NO: 120:

(i) SEQUENCE CHARACTERISTICS:
         (A) LENGTH: 7
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (785-791)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 120:

Gln Gly Ile Leu Glu Arg Val
                  5

(2) INFORMATION FOR SEQ ID NO: 121:

(i) SEQUENCE CHARACTERISTICS:
         (A) LENGTH: 8
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (784-791)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 121:

Val Gln Gly Ile Leu Glu Arg Val
                  5

(2) INFORMATION FOR SEQ ID NO: 122:

(i) SEQUENCE CHARACTERISTICS:
         (A) LENGTH: 9
         (B) TYPE: AMINO ACID
         (D) TOPOLOGY: LINEAR (ii) MOLECULE TYPE: PEPTIDE (ix) FEATURE:
         (A) NAME/KEY: HUMAN iNOS (783-791)
         (B) LOCATION: CARBOXY TERMINAL WITH AMIDE
         (C) IDENTIFICATION METHOD: AMINO ACID ANALYSIS
         (D) OTHER INFORMATION:

(xi) SEQUENCE DESCRIPTION: SEQ ID NO: 122:

Leu Val Gln Gly Ile Leu Glu Arg Val
                  5

(2) INFORMATION FOR SEQ ID NO: 123:

(i) SEQUENCE CHARACTERISTICS:
```

```
        (A) LENGTH: 5
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (786-790)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 123:

Gly Ile Leu Glu Arg
              5

(2) INFORMATION FOR SEQ ID NO: 124:

(i) SEQUENCE CHARACTERISTICS:
        (A) LENGTH: 6
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (785-790)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 124:

Gln Gly Ile Leu Glu Arg
              5

(2) INFORMATION FOR SEQ ID NO: 125:

(i) SEQUENCE CHARACTERISTICS:
        (A) LENGTH: 7
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (784-790)
        (B) LOCATION: CARBOXY TERMINAL WITH AMIDE
        (C) IDENTIFICATION METHOD: AMINO ACID ANALYSIS
        (D) OTHER INFORMATION:

(xi) SEQUENCE DESCRIPTION: SEQ ID NO: 125:

Val Gln Gly Ile Leu Glu Arg
              5

(2) INFORMATION FOR SEQ ID NO: 126:

(i) SEQUENCE CHARACTERISTICS:
        (A) LENGTH: 8
        (B) TYPE: AMINO ACID
        (D) TOPOLOGY: LINEAR (ii) MOLECULE TYPE: PEPTIDE (ix) FEATURE:
        (A) NAME/KEY: HUMAN iNOS (783-790)
        (B) LOCATION: CARBOXY TERMINAL WITH AMIDE
```

-continued

```
    (C) IDENTIFICATION METHOD: AMINO ACID ANALYSIS
    (D) OTHER INFORMATION:

(xi) SEQUENCE DESCRIPTION:  SEQ ID NO: 126:

Leu  Val  Gln  Gly  Ile  Leu  Glu  Arg
                     5
```